United States Patent
Alimi et al.

(10) Patent No.: US 8,323,252 B2
(45) Date of Patent: Dec. 4, 2012

(54) METHOD OF TREATING SKIN ULCERS USING OXIDATIVE REDUCTIVE POTENTIAL WATER SOLUTION

(75) Inventors: Hojabr Alimi, Santa Rosa, CA (US); Andres Gutierrez, Petaluma, CA (US)

(73) Assignee: Oculus Innovative Sciences, Inc., Petaluma, CA (US)

(*) Notice: Subject to any disclaimer, the term of this patent is extended or adjusted under 35 U.S.C. 154(b) by 580 days.

(21) Appl. No.: 11/388,912

(22) Filed: Mar. 23, 2006

(65) Prior Publication Data

US 2006/0235350 A1     Oct. 19, 2006

Related U.S. Application Data

(60) Provisional application No. 60/760,635, filed on Jan. 20, 2006, provisional application No. 60/760,567, filed on Jan. 20, 2006, provisional application No. 60/760,645, filed on Jan. 20, 2006, provisional application No. 60/760,557, filed on Jan. 20, 2006, provisional application No. 60/730,743, filed on Oct. 27, 2005, provisional application No. 60/667,101, filed on Mar. 31, 2005, provisional application No. 60/664,361, filed on Mar. 23, 2005, provisional application No. 60/676,883, filed on May 2, 2005.

(51) Int. Cl.
- *A61M 35/00* (2006.01)
- *A61K 33/00* (2006.01)
- *A01N 59/00* (2006.01)

(52) U.S. Cl. ............... 604/289; 604/293; 424/661

(58) Field of Classification Search ........ 604/19, 604/29, 289, 290; 424/665
See application file for complete search history.

(56) References Cited

U.S. PATENT DOCUMENTS

| | | |
|---|---|---|
| 3,066,095 A | 11/1962 | Hronas |
| 3,975,246 A | 8/1976 | Eibl et al. |
| 3,975,247 A * | 8/1976 | Stralser ............ 205/701 |
| 4,048,032 A | 9/1977 | Eibl |
| 4,121,991 A | 10/1978 | Miller et al. |
| 4,236,992 A | 12/1980 | Themy |
| 4,242,446 A | 12/1980 | Madappally et al. |
| 4,296,103 A | 10/1981 | Laso |
| 4,615,937 A | 10/1986 | Bouchette |
| 4,666,621 A | 5/1987 | Clark et al. |
| 4,670,252 A | 6/1987 | Sampathkumar |
| 4,767,511 A | 8/1988 | Aragon |
| 4,781,974 A | 11/1988 | Bouchette et al. |
| 4,979,938 A | 12/1990 | Stephen et al. |
| 5,063,922 A | 11/1991 | Hakkinen |
| 5,079,010 A | 1/1992 | Natterer et al. |

(Continued)

FOREIGN PATENT DOCUMENTS

CN   1 231 994 A   10/1999

(Continued)

OTHER PUBLICATIONS

Annex to Form PCT/ISA/206, Communication Relating to the Results of the Partial International Search for PCT/US2006/016856 (Date of Mailing: Dec. 27, 2006).

(Continued)

*Primary Examiner* — Susan Su
(74) *Attorney, Agent, or Firm* — Leydig, Voit & Mayer, Ltd.

(57) ABSTRACT

Provided is a method of treating skin ulcers and related complications in patients by administering an oxidative reduction potential (ORP) water solution that is stable for at least twenty-four hours.

23 Claims, 23 Drawing Sheets

U.S. PATENT DOCUMENTS

| Patent No. | | Date | Inventor(s) | Ref |
|---|---|---|---|---|
| 5,084,011 | A | 1/1992 | Grady | |
| 5,165,910 | A * | 11/1992 | Oikawa et al. | 423/477 |
| 5,244,768 | A | 9/1993 | Inaba | |
| 5,271,943 | A | 12/1993 | Bogart et al. | |
| 5,287,847 | A | 2/1994 | Piper et al. | |
| 5,312,281 | A | 5/1994 | Takahashi et al. | |
| 5,334,383 | A | 8/1994 | Morrow | |
| 5,376,242 | A | 12/1994 | Hayakawa | |
| 5,388,571 | A | 2/1995 | Roberts et al. | |
| 5,427,667 | A * | 6/1995 | Bakhir et al. | 204/260 |
| 5,445,722 | A | 8/1995 | Yamaguti et al. | |
| 5,449,442 | A * | 9/1995 | Yamada et al. | 205/701 |
| 5,474,662 | A | 12/1995 | Miyamae | |
| 5,507,932 | A | 4/1996 | Robinson | |
| 5,510,009 | A | 4/1996 | Arai et al. | |
| 5,543,030 | A | 8/1996 | Shiramizu et al. | |
| 5,560,816 | A | 10/1996 | Robinson | |
| 5,578,022 | A | 11/1996 | Scherson et al. | |
| 5,593,554 | A | 1/1997 | Yamanaka et al. | |
| 5,599,438 | A | 2/1997 | Shiramizu et al. | |
| 5,615,764 | A | 4/1997 | Satoh | |
| 5,616,221 | A | 4/1997 | Aoki et al. | |
| 5,620,587 | A | 4/1997 | Nakamura | |
| 5,622,725 | A | 4/1997 | Kross | |
| 5,622,848 | A | 4/1997 | Morrow | |
| 5,624,535 | A | 4/1997 | Tsuchikawa et al. | |
| 5,628,848 | A | 5/1997 | Friese et al. | |
| 5,635,040 | A | 6/1997 | Bakhir et al. | |
| 5,635,053 | A | 6/1997 | Aoki et al. | |
| 5,662,625 | A | 9/1997 | Westwood | |
| 5,674,365 | A | 10/1997 | Sano | |
| 5,674,537 | A | 10/1997 | Morrow | |
| 5,720,869 | A | 2/1998 | Yamanaka et al. | |
| 5,728,274 | A | 3/1998 | Kamitani et al. | |
| 5,728,287 | A | 3/1998 | Hough et al. | |
| 5,731,008 | A | 3/1998 | Morrow | |
| 5,736,027 | A | 4/1998 | Nakamura | |
| 5,759,478 | A | 6/1998 | Kajiwara et al. | |
| 5,762,779 | A | 6/1998 | Shiramizu et al. | |
| 5,783,052 | A | 7/1998 | Bakhir et al. | |
| 5,792,090 | A | 8/1998 | Ladin | |
| 5,798,028 | A | 8/1998 | Tsuchikawa et al. | |
| 5,833,831 | A | 11/1998 | Kitajima et al. | |
| 5,843,291 | A | 12/1998 | Eki et al. | |
| 5,858,201 | A | 1/1999 | Otsuka et al. | |
| 5,858,202 | A | 1/1999 | Nakamura | |
| 5,871,623 | A | 2/1999 | Dakhir et al. | |
| 5,888,357 | A | 3/1999 | Mitsumori et al. | |
| 5,897,757 | A | 4/1999 | Sano | |
| 5,900,257 | A | 5/1999 | Breton et al. | |
| 5,902,619 | A | 5/1999 | Rubow | |
| 5,906,810 | A | 5/1999 | Turner | |
| 5,908,707 | A | 6/1999 | Cabell et al. | |
| 5,928,488 | A | 7/1999 | Newman | |
| 5,928,491 | A | 7/1999 | Yu et al. | |
| 5,932,171 | A | 8/1999 | Malchesky | |
| 5,938,915 | A | 8/1999 | Morisawa | |
| 5,938,916 | A | 8/1999 | Bryson et al. | |
| 5,944,978 | A | 8/1999 | Okazaki | |
| 5,948,220 | A | 9/1999 | Kamitani et al. | |
| 5,951,859 | A | 9/1999 | Mirua et al. | |
| 5,963,435 | A | 10/1999 | Biernson | |
| 5,964,089 | A | 10/1999 | Murphy et al. | |
| 5,965,009 | A | 10/1999 | Shimamune et al. | |
| 5,985,110 | A | 11/1999 | Bakhir et al. | |
| 5,993,639 | A | 11/1999 | Miyashita et al. | |
| 5,997,717 | A | 12/1999 | Miyashita et al. | |
| 6,007,686 | A | 12/1999 | Welch et al. | |
| 6,007,693 | A | 12/1999 | Silveri | |
| 6,007,696 | A | 12/1999 | Takayasu et al. | |
| 6,033,539 | A | 3/2000 | Gablenko | |
| 6,056,866 | A | 5/2000 | Maeda et al. | |
| 6,059,941 | A | 5/2000 | Bryson et al. | |
| 6,093,292 | A | 7/2000 | Akiyama | |
| 6,106,691 | A | 8/2000 | Nakamura et al. | |
| 6,117,285 | A | 9/2000 | Welch et al. | |
| 6,121,317 | A | 9/2000 | Wu et al. | |
| 6,126,796 | A | 10/2000 | Shimamune et al. | |
| 6,126,810 | A | 10/2000 | Fricker et al. | |
| 6,139,876 | A | 10/2000 | Kolta | |
| 6,143,163 | A | 11/2000 | Sawamoto et al. | |
| 6,149,780 | A | 11/2000 | Miyake | |
| 6,171,551 | B1 | 1/2001 | Malchesky et al. | |
| 6,174,419 | B1 | 1/2001 | Akiyama | |
| 6,187,154 | B1 | 2/2001 | Yamaguchi et al. | |
| 6,200,434 | B1 | 3/2001 | Shinjo et al. | |
| 6,210,748 | B1 | 4/2001 | Nagahara et al. | |
| 6,228,251 | B1 | 5/2001 | Okazaki | |
| 6,231,747 | B1 | 5/2001 | Fukuzuka et al. | |
| 6,231,878 | B1 | 5/2001 | Komatsu et al. | |
| 6,245,210 | B1 * | 6/2001 | Nakamura et al. | 205/464 |
| 6,251,259 | B1 | 6/2001 | Satoh et al. | |
| 6,258,225 | B1 | 7/2001 | Yamaoka | |
| 6,277,266 | B1 | 8/2001 | Yamaoka | |
| 6,280,594 | B1 | 8/2001 | Yamaoka | |
| 6,294,073 | B1 | 9/2001 | Shirota et al. | |
| 6,296,744 | B1 | 10/2001 | Djeiranishvili et al. | |
| 6,333,054 | B1 | 12/2001 | Rogozinski | |
| 6,340,663 | B1 | 1/2002 | Deleo et al. | |
| 6,342,150 | B1 | 1/2002 | Sale et al. | |
| 6,350,376 | B1 | 2/2002 | Imaoka et al. | |
| 6,358,395 | B1 | 3/2002 | Schorzman et al. | |
| 6,361,665 | B1 | 3/2002 | Vorack | |
| 6,368,592 | B1 | 4/2002 | Colton et al. | |
| 6,375,809 | B1 | 4/2002 | Kato et al. | |
| 6,384,363 | B1 | 5/2002 | Hayakawa et al. | |
| 6,391,169 | B1 | 5/2002 | Hara et al. | |
| 6,426,066 | B1 | 7/2002 | Najafi et al. | |
| 6,436,445 | B1 * | 8/2002 | Hei et al. | 424/667 |
| 6,444,255 | B2 | 9/2002 | Nagahara et al. | |
| 6,462,250 | B1 | 10/2002 | Kuriyama et al. | |
| 6,464,845 | B2 | 10/2002 | Shirota et al. | |
| 6,475,371 | B1 | 11/2002 | Shirahata et al. | |
| 6,506,416 | B1 | 1/2003 | Okauchi et al. | |
| 6,527,940 | B1 | 3/2003 | Shimamune et al. | |
| 6,544,502 | B2 | 4/2003 | Heesch | |
| 6,551,492 | B2 | 4/2003 | Hanaoka | |
| 6,565,736 | B2 | 5/2003 | Park et al. | |
| 6,585,867 | B1 | 7/2003 | Asano | |
| 6,585,868 | B1 | 7/2003 | Chihara | |
| 6,598,602 | B1 | 7/2003 | Sjoholm | |
| 6,620,315 | B2 | 9/2003 | Martin | |
| 6,623,615 | B1 | 9/2003 | Morisawa et al. | |
| 6,623,695 | B2 | 9/2003 | Malchesky et al. | |
| 6,624,135 | B2 | 9/2003 | Takano | |
| 6,632,347 | B1 | 10/2003 | Buckley et al. | |
| 6,638,364 | B2 | 10/2003 | Harkins et al. | |
| 6,638,413 | B1 | 10/2003 | Weinberg et al. | |
| 6,663,306 | B2 | 12/2003 | Policicchio et al. | |
| 6,716,335 | B2 | 4/2004 | Takesako et al. | |
| 6,723,226 | B1 | 4/2004 | Takayasu et al. | |
| 6,733,435 | B2 * | 5/2004 | Canedo | 600/9 |
| 6,743,351 | B1 | 6/2004 | Arai et al. | |
| 6,752,757 | B2 | 6/2004 | Muir et al. | |
| 6,767,342 | B1 * | 7/2004 | Cantwell | 604/304 |
| 6,793,846 | B2 * | 9/2004 | Yoshikawa et al. | 252/187.25 |
| 6,815,551 | B2 | 11/2004 | Albiez et al. | |
| 6,823,609 | B2 | 11/2004 | Moretti | |
| 6,827,849 | B2 | 12/2004 | Kurokawa et al. | |
| 6,833,206 | B2 | 12/2004 | Erdle et al. | |
| 6,833,207 | B2 | 12/2004 | Joos et al. | |
| 6,838,210 | B2 | 1/2005 | Sawa | |
| 6,843,448 | B2 | 1/2005 | Parmley | |
| 6,844,026 | B2 | 1/2005 | Anthony et al. | |
| 6,852,205 | B1 | 2/2005 | Toyoshima et al. | |
| 6,855,233 | B2 | 2/2005 | Sawada | |
| 6,855,490 | B2 | 2/2005 | Sompuram et al. | |
| 6,856,916 | B2 | 2/2005 | Shyu | |
| 6,866,756 | B2 | 3/2005 | Klien | |
| 6,867,048 | B2 | 3/2005 | Kovacs | |
| 6,874,675 | B2 | 4/2005 | Kida et al. | |
| 6,887,601 | B2 | 5/2005 | Moulthrop et al. | |
| 6,921,743 | B2 | 7/2005 | Scheder et al. | |
| 6,923,893 | B2 | 8/2005 | Sano | |
| 7,276,255 | B2 | 10/2007 | Selkon | |
| 7,393,522 | B2 * | 7/2008 | Najafi et al. | 424/78.04 |
| 7,749,370 | B2 * | 7/2010 | Sumita | 205/701 |

| | | |
|---|---|---|
| 2001/0012544 A1 | 8/2001 | Nagahara et al. |
| 2001/0022273 A1 | 9/2001 | Popov et al. |
| 2002/0023847 A1 | 2/2002 | Natsume |
| 2002/0027070 A1 | 3/2002 | Oyokota et al. |
| 2002/0027084 A1 | 3/2002 | Park et al. |
| 2002/0032141 A1 | 3/2002 | Harkins |
| 2002/0036134 A1 | 3/2002 | Shirota et al. |
| 2002/0227079 | 3/2002 | Hanaoka |
| 2002/0074237 A1 | 6/2002 | Takesako et al. |
| 2002/0082196 A1* | 6/2002 | Zaveri ............................... 514/2 |
| 2002/0112314 A1 | 8/2002 | Harkins |
| 2002/0134691 A1 | 9/2002 | Satoh et al. |
| 2002/0135220 A1 | 9/2002 | Yamaguchi et al. |
| 2002/0160053 A1 | 10/2002 | Yahagi et al. |
| 2002/0165220 A1 | 11/2002 | Heesch |
| 2002/0165431 A1 | 11/2002 | Muir et al. |
| 2002/0168418 A1 | 11/2002 | Lorenz et al. |
| 2002/0175085 A1 | 11/2002 | Harkins et al. |
| 2002/0176885 A1 | 11/2002 | Najafi et al. |
| 2002/0179884 A1 | 12/2002 | Hoshino et al. |
| 2002/0182262 A1* | 12/2002 | Selkon ........................... 424/600 |
| 2003/0015418 A1 | 1/2003 | Tseng et al. |
| 2003/0019764 A1 | 1/2003 | Baldwin et al. |
| 2003/0024828 A1 | 2/2003 | Kondo et al. |
| 2003/0045502 A1 | 3/2003 | Kataoka et al. |
| 2003/0049163 A1 | 3/2003 | Malchesky et al. |
| 2003/0056805 A1 | 3/2003 | Sumita |
| 2003/0062068 A1 | 4/2003 | Ko et al. |
| 2003/0064427 A1 | 4/2003 | Felkner et al. |
| 2003/0087427 A1 | 5/2003 | Colton et al. |
| 2003/0089618 A1 | 5/2003 | Satoh et al. |
| 2003/0098283 A1 | 5/2003 | Katayose et al. |
| 2003/0138498 A1* | 7/2003 | Yoshikawa et al. ........... 424/661 |
| 2003/0141200 A1 | 7/2003 | Harada |
| 2003/0155549 A1* | 8/2003 | Yoshikawa et al. ...... 252/187.32 |
| 2003/0185704 A1 | 10/2003 | Bernard et al. |
| 2003/0212005 A1* | 11/2003 | Petito et al. ..................... 514/21 |
| 2003/0219361 A1 | 11/2003 | Lee et al. |
| 2003/0230826 A1 | 12/2003 | Kawaguchi et al. |
| 2004/0004007 A1 | 1/2004 | Orolin et al. |
| 2004/0011665 A1* | 1/2004 | Koizumi et al. .............. 205/626 |
| 2004/0029761 A1 | 2/2004 | Wakamatsu et al. |
| 2004/0037737 A1 | 2/2004 | Marais et al. |
| 2004/0055896 A1 | 3/2004 | Anderson et al. |
| 2004/0060815 A1 | 4/2004 | Buckley et al. |
| 2004/0079791 A1 | 4/2004 | Kida et al. |
| 2004/0081705 A1 | 4/2004 | Gotou |
| 2004/0084325 A1 | 5/2004 | Weinberg et al. |
| 2004/0084326 A1 | 5/2004 | Weinberg et al. |
| 2004/0094406 A1 | 5/2004 | Sawada |
| 2004/0131695 A1 | 7/2004 | Hinze |
| 2004/0137078 A1* | 7/2004 | Najafi et al. .................. 424/661 |
| 2004/0154993 A1 | 8/2004 | Yanagihara et al. |
| 2004/0168909 A1 | 9/2004 | Larson |
| 2004/0168933 A1 | 9/2004 | Inoue |
| 2004/0171701 A1 | 9/2004 | Shaw |
| 2004/0172985 A1 | 9/2004 | Mamiya et al. |
| 2004/0177655 A1 | 9/2004 | Kodera et al. |
| 2004/0185311 A1 | 9/2004 | Muthuswamy et al. |
| 2004/0185313 A1 | 9/2004 | Halter et al. |
| 2004/0188248 A1 | 9/2004 | Sawa |
| 2004/0208940 A1* | 10/2004 | Selkon ........................... 424/661 |
| 2004/0231977 A1* | 11/2004 | Roselle et al. ................ 204/242 |
| 2004/0244537 A1 | 12/2004 | Runyon |
| 2004/0250323 A1 | 12/2004 | Arai et al. |
| 2004/0254744 A1 | 12/2004 | Shyu |
| 2004/0256317 A1 | 12/2004 | Yamada et al. |
| 2004/0265394 A1 | 12/2004 | Morris et al. |
| 2005/0000117 A1 | 1/2005 | Polegato |
| 2005/0054973 A1 | 3/2005 | Constantz et al. |
| 2005/0058013 A1 | 3/2005 | Warf et al. |
| 2005/0062289 A1 | 3/2005 | Cho et al. |
| 2005/0064259 A1 | 3/2005 | Coors |
| 2005/0067300 A1 | 3/2005 | Tremblay et al. |
| 2005/0074421 A1 | 4/2005 | Tanaka |
| 2005/0075257 A1 | 4/2005 | Scheper et al. |
| 2005/0101838 A1 | 5/2005 | Camillocci et al. |
| 2005/0109610 A1 | 5/2005 | Inamoto et al. |
| 2005/0121334 A1* | 6/2005 | Sumita ........................... 205/628 |
| 2005/0126927 A1 | 6/2005 | Lindauer et al. |
| 2005/0126928 A1 | 6/2005 | Hung et al. |
| 2005/0129996 A1 | 6/2005 | Moulthrop et al. |
| 2005/0139465 A1 | 6/2005 | Kasuya et al. |
| 2005/0139808 A1 | 6/2005 | Alimi |
| 2005/0142157 A1 | 6/2005 | Alimi |
| 2005/0153858 A1 | 7/2005 | Anthony et al. |
| 2005/0155863 A1 | 7/2005 | Kovacs et al. |
| 2005/0161950 A1 | 7/2005 | Borden et al. |
| 2005/0178349 A1 | 8/2005 | Tse |
| 2005/0178920 A1 | 8/2005 | Wilson |
| 2005/0183949 A1 | 8/2005 | Daly et al. |
| 2005/0183964 A1 | 8/2005 | Roberts et al. |
| 2005/0189234 A1 | 9/2005 | Gibson et al. |
| 2005/0189237 A1 | 9/2005 | Sano |
| 2005/0198963 A1 | 9/2005 | Wai et al. |
| 2005/0209518 A1 | 9/2005 | Sage et al. |
| 2006/0086622 A1* | 4/2006 | Prior ............................. 205/641 |
| 2006/0169575 A1* | 8/2006 | Sumita .......................... 204/164 |
| 2006/0263240 A1* | 11/2006 | Hopkins ......................... 422/28 |
| 2006/0275498 A1* | 12/2006 | Bagley .......................... 424/600 |
| 2007/0148256 A1* | 6/2007 | Yanagihara et al. .......... 424/600 |
| 2008/0160612 A1* | 7/2008 | Selkon ........................... 435/375 |
| 2008/0279963 A1* | 11/2008 | Najafi et al. .................. 424/661 |

FOREIGN PATENT DOCUMENTS

| | | |
|---|---|---|
| EP | 0 368 812 A1 | 5/1990 |
| EP | 0 601 891 A1 | 6/1994 |
| EP | 0 636 581 A1 | 7/1994 |
| EP | 0 740 329 A1 | 10/1996 |
| EP | 0 889 007 A1 | 4/1997 |
| EP | 0 826 636 A1 | 3/1998 |
| EP | 0 841 305 A2 | 5/1998 |
| EP | 0 949 205 A1 | 10/1999 |
| EP | 1 038 993 A | 9/2000 |
| EP | 1 064 845 A1 | 1/2001 |
| EP | 1 065 265 A1 | 1/2001 |
| EP | 1 074 515 A2 | 2/2001 |
| EP | 1 103 264 A2 | 5/2001 |
| EP | 1 162 176 A1 | 12/2001 |
| EP | 1 162 179 A1 | 12/2001 |
| EP | 1 293 481 A2 | 3/2003 |
| EP | 1 314 699 A1 | 5/2003 |
| EP | 1 386 887 A1 | 2/2004 |
| GB | 1 422 795 | 1/1976 |
| GB | 1 422 795 A1 | 1/1976 |
| GB | 2253860 A | 9/1992 |
| GB | 2352728 A | 2/2001 |
| JP | 01-194993 A1 | 8/1989 |
| JP | 01-218682 A1 | 8/1989 |
| JP | 02-149395 A1 | 6/1990 |
| JP | 05-339769 A | 12/1993 |
| JP | 06-182345 | 7/1994 |
| JP | 05-228474 | 9/1994 |
| JP | 05-228475 | 9/1994 |
| JP | 06-254567 | 9/1994 |
| JP | 06-312183 | 11/1994 |
| JP | 06-335685 | 12/1994 |
| JP | 07-000966 A | 1/1995 |
| JP | 07-031981 | 2/1995 |
| JP | 07-075784 A | 3/1995 |
| JP | 07-155760 | 6/1995 |
| JP | 07-214063 | 8/1995 |
| JP | 07-238640 | 12/1995 |
| JP | 07-323289 | 12/1995 |
| JP | 08-001160 A | 1/1996 |
| JP | 08-052476 | 2/1996 |
| JP | 08-061788 | 3/1996 |
| JP | 08-164192 | 6/1996 |
| JP | 08-326124 | 12/1996 |
| JP | 09-025236 | 1/1997 |
| JP | 09-157173 A2 | 6/1997 |
| JP | 09-290269 | 11/1997 |
| JP | 10-080686 | 3/1998 |
| JP | 10-113664 | 5/1998 |
| JP | 10-128331 A2 | 5/1998 |
| JP | 11-151493 A2 | 6/1999 |
| JP | 10-192860 | 3/2000 |
| JP | 2001/079548 | 3/2001 |

| | | | |
|---|---|---|---|
| JP | 2000/084559 | | 4/2001 |
| JP | 2001-096275 | A | 4/2001 |
| JP | 2001/113276 | | 6/2001 |
| JP | 2001-191076 | A2 | 7/2001 |
| JP | 2001286868 | A * | 10/2001 |
| JP | 03-236315 | B2 | 12/2001 |
| JP | 03-247134 | B2 | 1/2002 |
| JP | 2002-059164 | A | 2/2002 |
| JP | 03-299250 | B2 | 7/2002 |
| JP | 03-338435 | B2 | 10/2002 |
| JP | 03-396853 | B2 | 4/2003 |
| JP | 2003/236543 | A1 | 8/2003 |
| JP | 03-458341 | B2 | 10/2003 |
| JP | 2004/049946 | A1 | 2/2004 |
| JP | 2004/216349 | A1 | 8/2004 |
| JP | 2004/223306 | A1 | 8/2004 |
| JP | 2004/223309 | A1 | 8/2004 |
| JP | 2004/223310 | A1 | 8/2004 |
| JP | 2004/232413 | A1 | 8/2004 |
| JP | 2005/013520 | A2 | 1/2005 |
| JP | 2005/058848 | A2 | 3/2005 |
| SU | 1296156 | A | 3/1987 |
| WO | WO 95/01137 | A1 | 1/1995 |
| WO | WO 96/02271 | A1 | 2/1996 |
| WO | WO 96/14835 | A1 | 5/1996 |
| WO | WO 96/16555 | A1 | 6/1996 |
| WO | WO 97/40814 | A1 | 11/1997 |
| WO | WO 97/46489 | A1 | 12/1997 |
| WO | WO 97/49638 | A | 12/1997 |
| WO | WO 98/03713 | A1 | 1/1998 |
| WO | WO 98/17588 | A1 | 4/1998 |
| WO | WO 98/27013 | | 6/1998 |
| WO | WO 98/42625 | A1 | 10/1998 |
| WO | WO 98/58880 | A1 | 12/1998 |
| WO | WO 99/00588 | A2 | 1/1999 |
| WO | WO 99/28238 | A1 | 6/1999 |
| WO | WO 0033757 | A1 | 6/2000 |
| WO | WO 00/076475 | A1 | 12/2000 |
| WO | WO 01/13926 | | 3/2001 |
| WO | WO 01/54704 | A1 | 8/2001 |
| WO | WO 01/056616 | A2 | 8/2001 |
| WO | WO 01/56616 | A2 | 8/2001 |
| WO | WO 02/04032 | A2 | 1/2002 |
| WO | WO 03/000957 | A1 | 6/2002 |
| WO | WO 03/024491 | A2 | 3/2003 |
| WO | WO 03/042111 | A2 | 5/2003 |
| WO | WO 03/048421 | A1 | 6/2003 |
| WO | WO 03/076568 | A2 | 9/2003 |
| WO | WO 03/103522 | A1 | 12/2003 |
| WO | WO 2004/076721 | A1 | 9/2004 |
| WO | WO 2004/078654 | A2 | 9/2004 |
| WO | WO 2004/079051 | A1 | 9/2004 |
| WO | WO 2004/081222 | A2 | 9/2004 |
| WO | WO 2004/082690 | A1 | 9/2004 |
| WO | WO 2004/092571 | A1 | 10/2004 |
| WO | WO 2005/003848 | A1 | 1/2005 |
| WO | WO 2005/011417 | A2 | 2/2005 |
| WO | WO 2005/020896 | A2 | 3/2005 |
| WO | WO 2005/030651 | A1 | 4/2005 |
| WO | WO 2005/061394 | A1 | 7/2005 |
| WO | WO 2005/065383 | A2 | 7/2005 |
| WO | WO 2005/265383 | A2 | 7/2005 |
| WO | WO 2005/075581 | A1 | 8/2005 |
| WO | WO 2005/080639 | A1 | 9/2005 |
| WO | WO 2005/082176 | A1 | 9/2005 |
| WO | WO 2006/014578 | A2 | 2/2006 |
| WO | WO 2006/102680 | A2 | 9/2006 |
| WO | WO 2006/102680 | A3 | 9/2006 |
| WO | WO 2006/102681 | A2 | 9/2006 |
| WO | WO 2006/119300 | A2 | 11/2006 |

OTHER PUBLICATIONS

Dimri, et al., "A biomarker that identifies senescent human cell in culture and in aging skin in vivo," *Proc. Natl. Acad. Sci. USA*, 92, 9363-9667 (1995).

International Search Report for PCT/US2006/011252 (Nov. 10, 2006).

Written Opinion for PCT/US2006/011252 (Nov. 10, 2006).

International Preliminary Report on Patentability for PCT/US2006/016856, dated Nov. 6, 2007.

International Search Report for PCT/US2006/016856, dated Mar. 21, 2007.

International Search Report for PCT/US2007/060854, dated Sep. 4, 2007.

Written Opinion for PCT/US2007/060854, dated Sep. 4, 2007.

International Search Report for PCT/US2007/060856, dated Aug. 31, 2007.

Written Opinion for PCT/US2007/060856, dated Aug. 31, 2007.

International Search Report for PCT/US2007/060860, dated Sep. 4, 2007.

Written Opinion for PCT/US2007/060860, dated Sep. 4, 2007.

Kubota, et al., "Effectiveness of acidic oxidative potential water in peritoneal lavage for perforated appendicitis," *Asian Journal of Surgery*, Department of Surgery, University of Hong Kong, Hong Kong., 22(3), pp. 282-284 (Jul. 1999).

International Search Report for PCT/US2006/011251 (Sep. 14, 2006).

Written Opinion for PCT/US2006/011251 (Sep. 14, 2006).

European Search Report for EP 1 103 264.

European Search Report for EP 1 293 481.

International Search Report for PCT/US02/38861.

International Search Report in PCT/US2004/043961 (Nov. 25, 2005).

Office Action for U.S. Appl. No. 10/146,140 dated Mar. 3, 2006.

Supplementary European Search Report for EP 02 79 0029.

A communication from the International Searching Authority including the report of the partial international search for PCT/US2004/043961 (Oct. 4, 2005).

Arrigo, et al., "Cytotoxic effects induced by oxidative stress in culture mammalian cells and protection provided by Hsp27 expression," (2005) (source unknown).

Ayliffe, "Working Party Report: Decontamination of minimally invasive surgical endoscopes and accessories," Journal of Hospital Infection, 45, 263-277 (2000).

Badia, et al., "Saline Wound Irrigation Reduces the Postoperative Infection Rate in Guinea Pigs." Journal of Surgical Research, 63, 457-459 (1996).

Bari, et al., "Chemical and irradiation treatments for killing *Escherichia coli* O157:H7 on alfalfa, radish, and mung bean seeds," *J Food Prot.*, 66(5), 767-74 (2003).

Bari, et al., "Effectiveness of electrolyzed acidic water in killing *Escherichia coli* O157:H7, *Salmonella enteritidis*, and Listeria monocytogenes on the surfaces of tomatoes," *J Food Prot.*, 66(4), 542-8 (2003).

Beckman, et al., "The free radical theory of aging matures," Physiol. Rev. 78, 547-581 (1998).

Boulton, *The Diabetic Foot*. "Diabetes: Clinical Management." Chapter 26, 293-306.

Carlson, "Redox media as a factor in destroying germs," *Schriftenreihe des Vereins fuer Wasser-, Boden- und Lufthygiene*, 31, 21-39 (1970).

Carton, et al., "Hypotonicity induces membrane protrusions and actin remodeling via activation of small GTPases Rac and Cdc42 in Rat-1 fibroblast," *Am. J. Physiol. Cell. Physiol.*, 285, C935-C944 (2003).

Chernomorskii, "Diagram of the electrochemical stability of water", *Zhurnal Fizicheskoi Khimii*, 51(4), 924-925 (1977).

Chisholm, "Wound Evaluation and Cleansing." Soft Tissue Emergencies, 10(4), 665-672 (1992).

De Grey, "Reactive oxygen species production in the mitochondrial matrix: implications for the mechanism of mitochondrial mutation accumulation," *Rejuvenation Res.*, 8(1), 13-17 (2005).

Dire, et al., "A Comparison of Wound Irrigation Solutions Used in the Emergency Department," Ann Emerg Med., 19(6), 704-8 (1998).

Dressler, "Standards and Histogram Interpretation in DNA Flow Cytometry," *Methods in Cell Biology*, 41, 241-262 (1994).

Dyson, et al., "Comparison of the Effects of Moist and Dry Conditions on Dermal Repair," Journal for Investigative Dermatology, 91(5), 434-439 (1988).

Erwin-Toth, et al., "Wound Care Selecting the Right Dressing," Am J Nurs., 95(2), 46-51 (1995).

Fabrizio, et al., "Comparison of electrolyzed oxidizing water with various antimicrobial interventions to reduce Salmonella species on poultry," *Poult. Sci.*, 81(10), 1598-605 (2002).

Field, et al., "Overview of Wound Healing in a Moist Environment," Am J Surg., 167(1A), 2S-6S (1994).

Flint, et al., "Virus cultivation, detection and genetics," Chapter 2, *Principles of Virology, Molecular Biology, Pathogenesis and Control*, ASM Press 2000; 32.

Fraise, "Choosing disinfectants," *J Hosp infect*, 43, 255-264 (1999).

Fraga, et al., "Ascorbic acid protects against endogenous oxidative DNA damage in human sperm," *Proc. Natl. Acad. Sci USA*, 88, 11003-11006 (1991).

Frippiat, et al., "Subcytotoxic $H_2O_2$ stress triggers a release of transforming growth factor-beta, which induces biomarkers of cellular senescence of human diploie fibroblast, " *J. Biol. Chem. 276*, 2531-2537 (2001).

Fomin, et al., "Participation of water [hydroxyl ions] in oxidation-reduction processes," *Sostoyanie Rol Vody Biol. Ob'ektakh, Simp., Tiflis*, 120-131 (1967).

Gao, et al., "Observation on the effect of disinfection to HBs Ag by electrolyzed oxidizing water," *Zhonghua Liu Xing Bing Xue Za Zhi*, 22, 40-42 (2001).

Goberdham, et al., "A biomarker that identifies senescent human cell in culture and in aging skin in vivo," *Proc. Natl. Acad. Sci. USA*, 92, 9663-9667 (1995).

Guitierrez, et al., "Produccion de agents biologicos par alas terapias genicas y celulares en humanos," *Diagnostico molecular en medicina*, 265-291 (2003).

Harada, "Behavior of hydrogen peroxide in electrolyzed anode water," *Biosci. Biotechnol Biochem.*, 66(9), 1783-91 (2002).

Hatto, et al., "The physiological property and function of the electrolyzed-ionized calcium Aquamax on water molecular clusters fractionization," *Artif. Organs*, 21(1), 439 (1997).

Hayashi, et al., "Successful treatment of mediastinitis after cardiovascular surgery using electrolyzed strong acid water aqueous solution," *Artif Organs*, 21, 39-42 (1997).

Higgins, et al., "Wound dressings and Topical Agents." *The Diabetic Foot*, 12(1), 31-40, (1995).

Hinman, et al., "Effect of Air Exposure and Occlusion on Experimental Human Skin Wounds," *Nature*, 200, 377-379 (1963).

Hollander, et al., "Laceration Management," *Annals of Emergency Medicine*, 34(3), 356-367 (1999).

Horiba, et al., "Bactericidal effect of electrolyzed neutral water on bacteria isolated from infected root canals," *Oral Surg Oral Med Oral Pathol Oral Radiol Endod*, 87, 83-87 (1999).

Horita, et al., "Healing of Fournier's gangrene of the scrotum in a haemodialysis patient after conservative therapy alone," *Nephrology Dialysis Transplantation*, 15 (3), 419-421 (2000).

Inoue, et al., "Trial of electrolyzed strong acid aqueous solution lavage in the treatment of peritonitis and intraperitoneal abscess," *Artif Organs*, 21, 28-31 (1997).

Ivanova, et al., "Mechanism of the extracellular antioxidant defend," *Experimental pathology and parasitology*, 4, 49-59 (2000).

Iwasawa, et al., "Bactericidal effect of acidic electrolyzed water—comparison of chemical acidic sodium hydrochloride (NaOCl) solution," *Kansenshogaku Zasshi*,; 70(9), 915-22 (1996).

Iwasawa, et al., "The influence of pH on bactericidal effects of strong acidic electrolyzed water," *Bokin Bobai*, 30(10), 635-643, (2002).

Jeter, et al., "Wound Dressings of the Nineties: Indications and Contraindications," *Wound Healing*, 8(4), 799-816 (1991).

Kaufman, "Preventing Diabetic Foot Ulcers," *Derm. Nurs.*, 6(5), 313-320 (1994).

Kiura, et al., "Bactericidal activity of electrolyzed acid water from solution containing sodium chloride at low concentration, in comparison with that at high concentration," *J Microbiol Methods*, 49(3), 285-93 (2002).

Kim, et al., "Efficacy of electrolyzed oxidizing water in inactivating Salmonella on alfalfa seeds and sprouts," *J Food Prot.*, 66(2), 208-14 (2003).

Kim, et al., "Roles of oxidation-reduction potential in electrolyzed oxidizing and chemically modified water for the inactivation of food-related pathogens," *J Food Prot*, 63, 19-24 (2000).

Kimbrough, et al., "Electrochemical removal of bromide and reduction of THM formation potential in drinking water," *Water Res.*, 36(19), 4902-6 (2002).

Kitaoka, "On the electrolytic separation factor of tritium," *Radioisotopes*, 30(5), 247-52 (1981).

Koseki, et al., "Effect of nitrogen gas packaging on the quality and microbial growth of fresh-cut vegetables under low temperatures," *J Food Prot.*, 65(2), 326-32 (2002).

Koseki, et al., "Effect of mild heat pre-treatment with alkaline electrolyzed water on the efficacy of acidic electrolyzed water against *Escherichia coli* O157:H7 and Salmonella on lettuce," *Food Microbiology*, 21(5), 559-566 (2004).

Koseki, et al., "Decontaminative effect of frozen acidic electrolyzed water on lettuce," *J Food Prot.*, 65(2), 411-4 (2002).

Koseki, et al., "Decontamination of lettuce using acidic electrolyzed water," *J Food Prot.*, 64(5), 652-8 (2001).

Koseki, et al., "Prediction of microbial growth in fresh-cut vegetables treated with acidic electrolyzed water during storage under various temperature conditions," *J Food Prot.*, 64(12), 1935-42 (2001).

Laing, "Diabetic Foot Ulcers," *Am J Surg*, 167, 31S-26S (1994).

Len, et al., "Ultraviolet spectrophotometric characterization and bactericidal properties of electrolyzed oxidizing water as influenced by amperage and pH," *J Food Prot*, 63, 1534-1537 (2000).

Len, et al., "Effects of storage conditions and pH on chlorine loss in electrolyzed oxidizing (EO) water," *J Agric Food Chem*, 50, 209-212 (2002).

Li, et al., "Preliminary study of microbiocide effect and its mechanism of electrolyzed oxidizing water," *Zhonghua Liu Xing Bing Xue.Za Zhi*, 7, 95-98 (1996).

Loshon, et al., "Analysis of the killing of spores of *Bacillus subtilis* by a new disinfectant, Sterilox," Journal of Applied Microbiology, 91, 1051-1058 (2001).

Madden, et al., "Application of Principles of Fluid Dynamics to Surgical Wound Irrigation," source unknown.

Mangram, et al., "Guideline for prevention of surgical site infection," *Infection Control and Hospital Epidemiology*, 1999, 20(4), 247-278 (1999).

Marnett, "Oxyradicals and DNA damage," Carcinogenesis, 21, 361-370 (2000).

Martinez, "Sterilant for Human Wounds is Changing Patients' Lives" Infection Control Today, (2004).

Middleton, et al., "Comparison of a solution of super-oxidized water (Sterilox) with glutaraldehyde for the disinfection of bronchoscopes, contaminated in vitro with *Mycobacterium tuberculosis* and *Mycobacterium avium-intracellulare* in sputum," *Journal of Hospital Infection*, 45, 278-282 (2000).

Michida, et al., "Biomimetic oxidation of diphenyl sulfide with electrochemical P-450 model system in CH2C12 treated with alkaline solution," *Yakugaku Zasshi*, 119(10), 780-5 (1999).

Minimal Access Therapy Decontamination Working Group, "Decontamination of minimally invasive surgical endoscopes and accessories," *J Hosp. Infect*, 45, 263-277 (2000).

Miranda-Altamirano et al., Treatment of 2nd and 3rd Degree Burns in 48 Pediatric Patients Without Routine Antibiotics Routine Using New "Super-oxidized Water Technology" Abstract for Meeting of the Texas Surgical Society, Apr. 1-3, 2005.

Miyamoto, et al., "Effectiveness of acidic oxidative potential water in preventing bacterial infection in islet transplantation," *Cell Transplant*, 8, 405-411 (1999).

Model, et al., "Effectiveness of electrolyzed oxidized water irrigation in a burn-wound infection," *J Trauma Injury, Infection, and Critical Care*, 49, 511-514 (2000).

Morita, et al., "Disinfection potential of electrolyzed solution containing sodium chloride at low concentrations," *J Virol Methods*, 85, 163-174 (2000).

Moscati, et al., "Comparison of Normal Saline with Tap Water for Wound Irrigation," American Journal of Emergency Medicine, 16(4), 379-385 (1998).

Moyer, et al., "Modulation of human fibroblast Gap junction intercellular communication by Hyaluronan," *J. Cell. Biol.* 196, 165-170 (2003).

Naderi, et al., "Oxidative stress-induced apoptosis in dividing fibroblast involves activation of p38 MAP kinase and over expression of Bax: Resistance of quiescent cells to oxidative stress," *Apoptosis*, 8, 91-100 (2003).

Nagamatsu, et al., "Application of electrolyzed acid water to sterilization of denture base part 1. Examination of sterilization effects on resin plate," *Dent. Mater J*, 20(2), 148-55, (2001).

Nagamatsu, et al., "Durability of bactericidal activity in electrolyzed neutral water by storage," *Dent Mater J*, 21, 93-104 (2002).

Nakae, et al., "Effectiveness of electrolyzed oxidized water irrigation in a burn-wound infection model," *J Trauma*, Sep.; 49(3): 511-4 (2000).

Nakagawa, et al., "Effect of rinsing hydrocolloid impressions using acidic electrolyzed water on surface roughness and surface hardness of stone models," *J Oral Sci.*, 44(3-4), 141-6 (2002).

Nakagawara, et al., "Spectroscopic characterization and the pH dependence of bactericidal activity of the aqueous chlorine solution," *Analytical Sciences*, 14(4), 691-698 (1998).

Nelson, "Newer technologies for endoscope disinfection: electrolyzed acid water and disposable-component endoscope systems," *Gasatrointest Endosc Clin N Am*, 10, 319-328 (2000).

Ogino, et al., "Treatment for abdominal aortic graft infection: irrigation with electrolyzed strong aqueous acid, in-situ grafting, and omentoplasty," *Thorac Cardiovasc Surg*, 48(1), 43-44 (2000).

Ohno, et al., "Mediastinal Irrigation with Superoxidized Water After Open-Heart Surgery: The Safety and Pitfalls of Cardiovascular Surgical Application," Surgery Today, 30, 1055-1056 (2000).

Okubo, et al., "Cytotoxicity and microbicidal activity of electrolyzed strong acid water and acidic hypochlorite solution under isotonic conditions," *Kansenshogaku Zasshi*, 73(10), 1025-31 (1999).

O'Neill, "Physiological significance of volume-regulatory transporters," *Am. J. Physiol.* 276, C995-C1001 (1999).

Oomori, et al., "The efficiency of disinfection of acidic electrolyzed water in the presence of organic materials," *Anal Sci*, 16, 265-369 (2000).

Ottender, et al., "Correlation of DNA adduct levels with tumor incidence: carcinogenic potency of DNA adducts," *Mutat. Res.*, 424, 237-247 (1999).

Park, et al., "Antimicrobial effect of electrolyzed water for inactivating *Campylobacter jejuni* during poultry washing," *International Journal of Food Microbiology*, 72(1-2), 77-83 (2002).

Park, "Effectiveness of electrolyzed water as a sanitizer for treating different surfaces," *J Food Prot.*, 65(8), 1276-80 (2002).

Park, et al., "Effects of chlorine and pH on efficacy of electrolyzed water for inactivating *Escherichia coli* O157:H7 and Listeria monocytogenes," *International Journal of Food Microbiology*, 91(1), 13-18 (2004).

Piaggesi, et al., "Sodium carboxyl-methyl-cellulose dressings in the management of deep ulcerations of diabetic foot," Diabet Med., 18(4), 320-4 (2001).

Powis, et al., "Redox signaling and the control of cell growth and death," *Pharmacol Ther.*, 68, 149-173 (1995).

Rodeheaver, et al., "Identification of the Wound Infection-Potentiating Factors in Soil," American Journal of Surgery, 128(1), 8-14, (1974).

Ruddy, et al., "Decontamination in Practice: Endoscopic decontamination: an audit and practical review," Journal of Hospital Infection, 50, 261-268 (2002).

Russell, "The effect of electrolyzed oxidative water applied using electrostatic spraying on pathogenic and indicator bacteria on the surface of eggs," *Poult. Sci.*, 82(1), 158-62 (2003).

Rutala ,et al., "New Disinfection and Sterilization Methods," *Centers for Disease Control and Prevention (CDC)*: Emerging Infectious Diseases, 7 (2), 348-353 (2001).

Sakai, "Development of ionic electrolyzed water and its utilities. The preparation of ionic electrolyzed water and its application to disinfection," *Kurin Tekunoroji* (1996), 6(3), 53-57 (1996).

Sakashita, et al., "Antimicrobial effects and efficacy on habitually hand-washing of strong acidic electrolyzed water—a comparative study of alcoholic antiseptics and soap and tap water", *Kansenshogaku Zasshi* 76, 373-377 (2002).

Sanders, "Diabetes Mellitus: Prevention of Amputation," *J Am Pod Med Assoc*, 84(7), 322-328 (1994).

Sawada, "Complete electrolysis using a microflow cell with an oil/water interface." *Anal Chem.*, 74(5), 1177-81 (2002).

Sekiya, et al., "Treatment of Infectious Skin Defects or Ulcers with Electrolyzed Strong Acid Aqueous Solution," *Artificial Organs*, 21 (1), 32-38 (1997).

Selkon,et al., "Evaluation of the antimicrobial activity of a new super-oxidized water, Sterilox®, for the disinfection of endoscopes," *Journal of Hospital Infection*, 41, 59-70 (1999).

Severino, et al., "Is β-galactosidase staining a marker of senescence in vitro and in vivo?" *Exp. Cell. Res.*, 257, 162-171 (2000).

Sharma, et al., "Treatment of *Escherichia coli* O157:H7 inoculated alfalfa seeds and sprouts with electrolyzed oxidizing water," *International Journal of Food Microbiology*, 86(3), 231-237 (2003).

Shen, et al., "Interactions of selenium compounds with other antioxidants in DNA damage and apoptosis in Human normal keratinocytes," *Cancer Epidemiol Biomarkders Prev.*, 10, 385-390 (2001).

Shetty, et al., "Evaluation of microbicidal activity of a new disinfectant: Sterilox® 2500 against *Clostridium difficile* spores, *Helicobacter pylori*, cancomycin resistant Enterococcus species, *Candida albicans* and several Mycobacterium species," *Journal of Hospital Infection*, 41, 101-105 (1999).

Shimmura, et al., "Acidic Electrolyzed Water in the Disinfection of the Ocular Surface," *Experimental Eye Research*, 70(1), 1-6 (2000).

Shirahata, et al., "Electrolyzed-reduced water scavenges active oxygen species and protects DNA from oxidative damage," *Biochem. Biophys. Res. Commun.*, 234(1), 269-74 (1997).

Singer, et al., "Evaluation and Management of Traumatic Lacerations," New England Journal of Medicine, 1142-1148 (1997).

Smirnov, et al., "Electron exchangers and electron- and ion-exchangers and their use in a water treatment system," *Khim. Aktiv. Polim. Ikh Primen*, 259-262 (1969).

Solovyeva, et al., "Cleaning effectiveness of root canal irrigation with electrochemically activated anolyte and catholyte solutions: a pilot study," *International Endodontic Journal*, 33, 494-504 (2000).

Soto, et al., "Bacterial sulfate production by biodesulfurization of aromatic hydrocarbons, determined by ion chromatography," *J Chromatogr A*, 824(1), 45-52 (1998).

Stein, "SV-40-transformed human fibroblasts: evidence for cellular aging in pre-crises cells," *J Cell, Physiol*, 125, 36-44 (1985).

Stevenson, et al., "Cleansing the Traumatic Wound by High Pressure Syringe Irrigation." *JACEP*, 5(1), 17-21 (1976).

Sumita, "Characteristics and use of acidified water from redox water generator," *Shokuhin Kogyo*, 40(10), 29-36 (1997).

Suzuki, "Novel products generated from 2'-deoxyguanosine by hypochlorous acid or a myeloperoxidase -$H_2O_2$-Cl-system: identification of diimino-imidazole and amino-imidazolone nucleosides," *Nucleic Acids Res.*, 30, 2555-2564 (2002).

Tanaka, et al., "The use of electrolyzed solutions for the cleaning and disinfecting of dialyzers" *Artif. Organs*, 24(12), 921-8 (2000).

Tanaka, et al., "Molecular basis of antiapoptotic effect of immunophilin ligands on hydrogen peroxide-induced apoptosis in human glioma cells," *Neurochem Res.*, 29(8), 1529-36 (2004).

Tanaka, et al., "Antimicrobial activity of superoxidized water" *Journal of Hospital Infection*, 34, 43-49 (1996).

Takeshita ,et al., "Influence of free residual chlorine concentration and pH on bactericidal effects of electrolyzed water," *Bokin Bobai*, 29(2), 69-72 (2001).

Takeyoshi, et al., "Primary eye irritation and 5-day cumulative skin irriation studies of super oxidized water in rabbits," *Oyo Yakuri*, 48(3), 173-177 (1994).

Tateno, et al., "MT-4 plaque formation can distinguish cytopathic substypes of the human immunodeficiency virus (HIV)," *Virology*, 167, 299-301 (1988).

Upright, et al., "Evaluation of Mesalt dressings and continuous wet saline dressings in ulcerating metastatic skin lesions," *Cancer Nursing*, 17(2), 149-155 (1994).

Valko, et al., "Role of oxygen radicals in DNA damage and cancer incidence," *Mol Cell Biochem*, 266, 37-56 (2004).

Van Britsom, et al., "A rapid method for the detection of uranium in surface water," Sci. Total Environ., 173-174, 83-9 (1995).

Venkitanarayanan, et al., "Efficacy of Electrolyzed Oxidizing Water for Inactivating *Escherichia coli* O157:H7, *Salmonella enteritidis*, and *Listeria monocytogenes*," *Applied and Environmental Microbiology*, 65 (9), 4276-4279 (1999).

Veves, et al., "A randomized, controlled trial of Promogran (a collagen/oxidized regenerated cellulose dressing) vs standard treatment in the management of diabetic foot ulcers," *Arch Surg.*, 137(7), 822-7 (2002).

Winter, "Formation of the Scab and the Rate of Epithelization of Superficial Wounds in the Skin of the Young Domestic Pig," *Nature*, 193, 293-294 (1962).

Xakellis, et al., "Hydrocolloid versus saline-gauze dressings in treating pressure ulcers: a cost-effectiveness analysis," *Arch Phys Med Rehabil.*, 73(5), 463-9 (1992).

Yahagi, et al., "Effect of Electrolyzed Water on Wound Healing," *Artificial Organs*, 24 (12), 984-987 (2000).

Yang, et al., "The effect of pH on inactivation of pathogenic bacteria on fresh-cut lettuce by dipping treatment with electrolyzed water," *Journal of Food Science*, 68(3), 1013-1017 (2003).

Yoshimoto, et al., "Virucidal effect of super oxidized water" *Kagaku Ryoho no Ryoiki*, 12(7), 1337-1342 (1996).

Young, et al., "Mechanisms of killing of *Bacillus subtilis* spores by hypochlorite and chlorine dioxide," *J Appl Microbiol*, 95, 54-67 (2003).

Zinkevich, et al., "The effect of super-oxidized water on *Escherichia coli*," *Journal of Hospital Infection*, 46, 153-156 (2000).

Zhang, et al., "Antioxidant superoxide dismutase attenuates increased endothelial permeability induced by platelet activating factor," *Soc Gynecol Investig.* 10, 5-10 (2003).

\* cited by examiner

Salt Drain

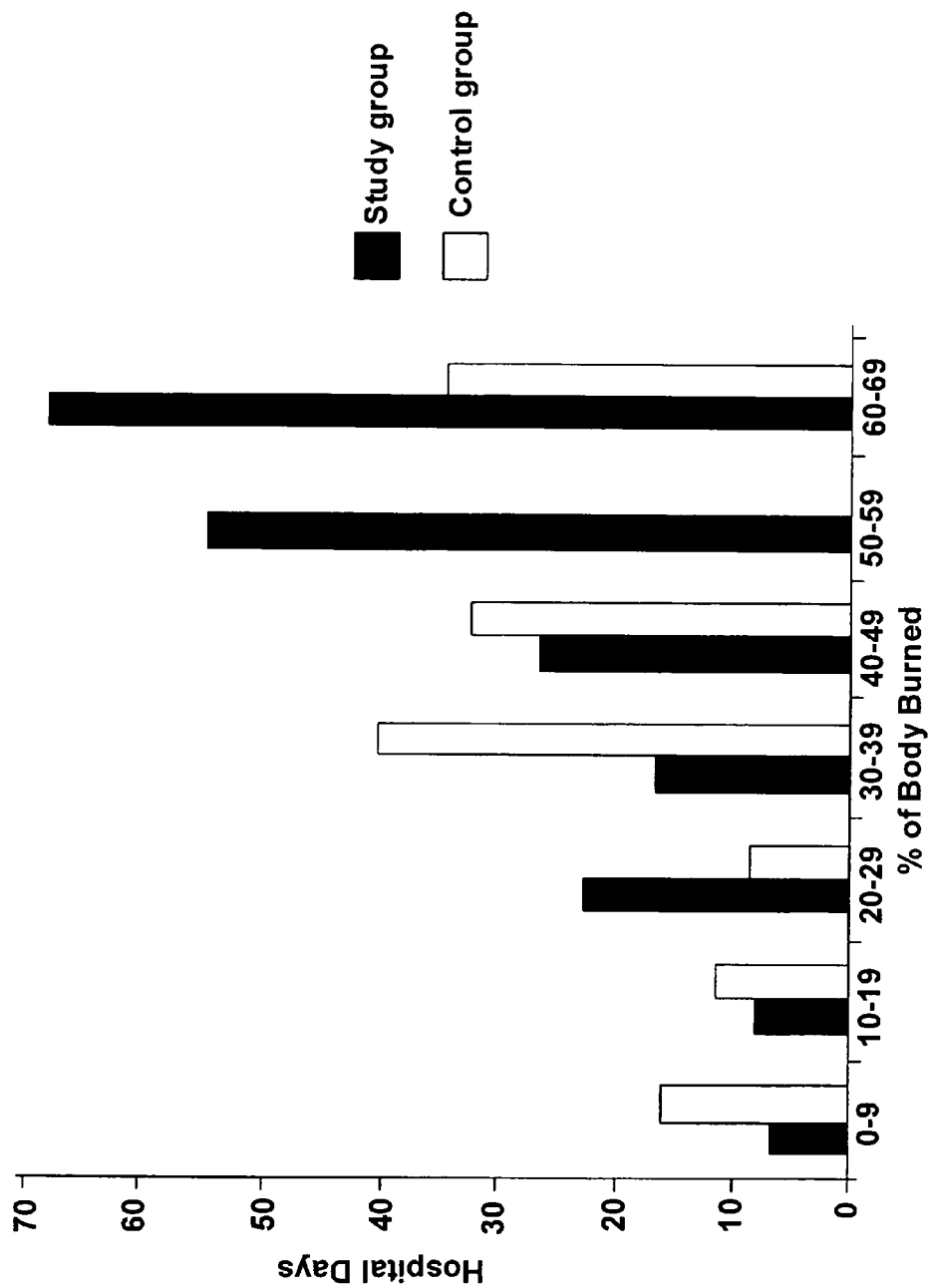

METHOD OF TREATING SKIN ULCERS USING OXIDATIVE REDUCTIVE POTENTIAL WATER SOLUTION

CROSS-REFERENCE TO RELATED APPLICATIONS

This patent application claims the benefit of U.S. Provisional Patent Application Nos. 60/760,635 filed Jan. 20, 2006; 60/760,567 filed Jan. 20, 2006; 60/760,645 filed Jan. 20, 2006; 60/760,557 filed Jan. 20, 2006; 60/730,743 filed Oct. 27, 2005; 60/676,883 filed May 2, 2005; 60/667,101 filed Mar. 31, 2005; and 60/664,361, filed Mar. 23, 2005; each of which is hereby incorporated herein in their entirety by reference.

BACKGROUND OF THE INVENTION

Skin ulcers are a significant clinical problem and can cause even more serious complications such as, for example, gangrene, systemic inflammatory syndrome, and sepsis. When these complications occur in skin ulcers on the extremities current treatment regimens may require amputations including above-the-knee leg amputation (AKA), below-the-knee leg amputations (BKA), and digital amputations with their obvious implications for the patient.

Skin ulcers have many causes, including venous insufficiency, arterial insufficiency, ischemic pressure, and neuropathies. Venous skin ulcers are the most common type of leg skin ulcers with women affected more than men. Venous skin ulcers are associated with venous hypertension and varicosities. Typically, venous skin ulcers are shallow and painful. Arterial skin ulcers are typically found in elderly patients with history of cardiac or cerebrovascular disease, leg claudication, impotence, and pain in distal foot. Concomitant venous disease is present in up to 25% of cases with an arterial ulcer. Pressure skin ulcers result from tissue ischemia. Pressure skin ulcers are commonly deep and often located over bony prominences. Neuropathic skin uclers are associated with trauma, prolonged pressure, usually plantar aspect of feet in patients with, for example, diabetes, neurologic disorders or Leprosy.

Venous insufficiency is a common cause of lower extremity skin ulcers, accounting for up to 80% of all cases. Of the approximately 7 million people in the United States with venous insufficiency, approximately 1 million develop venous leg ulcers. The cost of venous leg ulcers is estimated to be $1 billion per year in the United States and the average cost per patient exceeds $40,000. Venous skin ulcers are more common with increasing age, with peak prevalence between 60 and 80 years of age. However, younger patients also develop venous skin ulcers resulting in significant morbidity and time away from work. de Araujo et al., *Ann. Intern. Med.* 2003 138(4):326-34.

Pressure skin ulcers are another major cause of morbidity in older people and the most important care problem in nursing home residents dramatically increasing the cost of medical and nursing care. In particular, pressure skin ulcers of the foot are very common and are difficult to heal among elderly immobilized patients. Pressure skin ulcers at the malleolus, heel, or both develop as a result of pressure, shear, or friction concentrated on a small area over a bone prominence that lacks subcutaneous tissue. An untreated pressure skin ulcer may worsen and lead to cellulitis, chronic infection, or osteomyelitis. Landi et al., *Ann. Intern. Med.* 2003 139(8):635-41.

Diabetes is also a frequent cause of foot skin ulcers. The prevalence of diabetes in the U.S. is currently about 6%, or over 18 million people, including about 5 million undiagnosed people. In addition, type-2 diabetes appears to be increasing in the U.S. Diabetes is the leading nontraumatic cause of amputation in the U.S. The total number of lower-extremity amputations (LEAs) in diabetic patients in the U.S. is over 80,000 annually. The 3-year mortality rate after a diabetic LEA is between 35 and 50%. Direct costs for diabetic LEAs in the U.S. range from $22,700 for a toe amputation, to $51,300 for an above-the-knee amputation in 2001 dollars. Foot skin ulcers precede about 85% of LEAs in patients with diabetes. The 1-year incidence of new foot skin ulcers in patients with diabetes in the U.S. ranges from 1.0 to 2.6%. V. R. Driver et al., *Diabetes Care* 2005 28:248-253.

The conventional treatment of diabetic foot ulcers includes debridement, revascularization, dressings, and the treatment of any infections present. Debridement should remove all debris and necrotic material to render infection less likely. The common recommendation is that nonadherent dressings should cover diabetic foot ulcers at all times and occlusive dressings may lower the risk of infection.

Both wet and dry gangrene can occur in the diabetic foot. Wet gangrene is caused by a septic arteritis, secondary to soft-tissue infection or ulceration. Dry gangrene is secondary to a severe reduction in arterial perfusion and occurs in chronic critical ischemia. Revascularization followed by surgical debridement is recommended for the treatment of foot ulcers in diabetics. Although antibiotics are a critical component of the therapy, treatment of infection with antibiotics alone is usually insufficient to resolve the majority of diabetic foot infections. American Diabetes Association Consensus Statement, *Diabetes Care* 2003 26:3333-3341. Accordingly, there is particularly a need for additional methods of treatment of foot skin ulcers in diabetics.

The spectrum of chronic skin ulcers in which infection plays a clinical role includes critical limb ischemia (CLI), diabetic foot ulcers, below-knee amputations (BKA), methicillin-resistant *Staphylococcus aureus* (MRSA), and chronic venous insufficiency (CVI). The role of infection in these conditions may range from minor to severe, but it likely plays a significant role in most cases. Infected skin ulcers often require systemic antibiotics and, when present in the extremities, may require amputations.

There is a need to develop treatments of skin ulcers that reduce the need for amputation. In patients over 85 years of age, primary amputation (PA) still carries an excessively high mortality rate of 13-17%. In the highest risk patients, 30-day periprocedural mortality after amputation can range from 430% and morbidity from 20-37%, because many endstage. CLI patients will suffer from infection, sepsis, and progressive renal insufficiency. Successful rehabilitation after BKA is achieved in less than two-thirds of patients; after above-the-knee amputations, that fraction is less than one-half of patients. Overall, less than 50% of all patients requiring amputation ever achieve full mobility. There is a poor overall prognosis for the CLI patient with mortality rates greater than 50% after 3 years and twice the mortality rate after BKA versus limb salvage. In addition, the total cost of treating CLI in the United States is estimated at $10-20 billion per year. Similarly, the annual cost of follow-up or long-term care and treatment for an amputee is significantly greater than if the limb is salvaged.

Depending on the type and severity of the ulcer, the clinical picture could progress to an acute systemic inflammatory response syndrome (SIRS), sepsis or septic shock. The systemic inflammatory response syndrome (SIRS), a syndrome that encompasses the features of systemic inflammation without end-organ damage or identifiable bacteremia. SIRS is separate and distinct from sepsis, severe sepsis or septic shock. The key transition from SIRS to sepsis is the presence of an identified pathogen in the blood. The pathophysiology of SIRS includes, but is not limited to, complement activation, cytokine and arachidonic acid metabolites secretion, stimulated cell-mediated immunity, activation of the clotting cascades, and humoral immune mechanisms. Clinically SIRS is characterized by tachycardia, tachypnea, hypotension, hypoperfusion, oliguria, leukocytosis or leukopenia, pyrexia or hypothermia, metabolic acidosis, and the need for volume support. SIRS may affect all organ systems and may lead to multiple organ dysfunction syndrome (MODS). Thus, even in early stages (i.e. SIRS), there is accumulation of pro-inflammatory cytokines at the site of the ulcer and in the blood that contribute to the establishment of multi-organ failure and death.

Accordingly, there remains a need for new methods of treating skin ulcers. The invention provides such methods. These and other advantages of the invention, as well as additional inventive features, will be apparent from the description of the invention provided herein.

BRIEF SUMMARY OF THE INVENTION

The present invention provides a method of preventing or treating a condition in a patient, which method comprises administering to the patient a therapeutically effective amount of an oxidative reductive potential (ORP) water solution, wherein the solution is stable for at least about twenty-four hours. The condition can include, e.g., medical conditions, illnesses, injuries, allergies, and the like, which are treatable with the ORP water solution of the present invention.

The present invention provides a method of treating skin ulcers in a patient by administering an oxidative reductive potential (ORP) water solution, wherein the solution is stable for at least about twenty-four hours. The invention also is directed to a method of treating skin ulcers in a patient by administering an oxidative reductive potential water solution, wherein the solution comprises anode water and cathode water. In one embodiment, the ORP water solution used in the method of the invention comprises one or more free chlorine speciesand is stable for at least about two months. The ORP water solution preferably comprises anode and cathode water.

In another embodiment, the ORP water solution comprises hypochlorous acid in an amount of from about 15 ppm to about 35 ppm, sodium hypochlorite in an amount of from about 25 ppm to about 50 ppm, is stable for at least about one week, and has a pH of from about 6.2 to about 7.8.

The present invention also provides a method of treating skin ulcers in a patient, which method comprises irrigating and/or washing the skin ulcer with an ORP water solution; soaking the skin ulcer in the ORP water solution; dressing the skin ulcer with a wound dressing saturated with the ORP water solution; and, optionally, repeating the washing, irrigating, soaking, and dressing steps, wherein the ORP water solution preferably has a pH of from about 6.4 to about 7.8. In one embodiment, the skin ulcer is soaked for at least about two minutes and optionally dried for at least about two minutes and the dressing is applied.

The present invention additionally provides a method of reducing the microbial load of a skin ulcer in a patient, which method includes administering the ORP water solution to the patient in an amount effective to reduce the microbial load and the local inflammatory process in the skin ulcer. The present invention further provides methods of decreasing the recurrence rate, decreasing the likelihood of amputation associated with a extremity ulcer, which method comprises administering to the patient an effective amount of the ORP water solution.

The present invention further provides a method of preventing multi-organ failure secondary to gangrene and related to the development of SIRS or sepsis, which method includes administering a therapeutically effective amount of an oxidative reductive potential (ORP) water solution to the patient to inhibit the secretion of new pro inflammatory molecules from inflammatory cells at the site of the skin ulcer and reduce the bacterial load of the skin ulcer, wherein the ORP water solution is stable for at least about twenty-four hours. The ORP water solution can be administered by contacting the solution with the skin ulcer tissues of a patient.

BRIEF DESCRIPTION OF THE DRAWINGS

FIG. 19 is a graphical comparison of the hospital stay length in days for patients treated with an exemplary ORP water solution (Study group) or standard therapy (Control group) broken down by the percentage of body surface area burned.

DETAILED DESCRIPTION OF THE INVENTION

Figure 1:
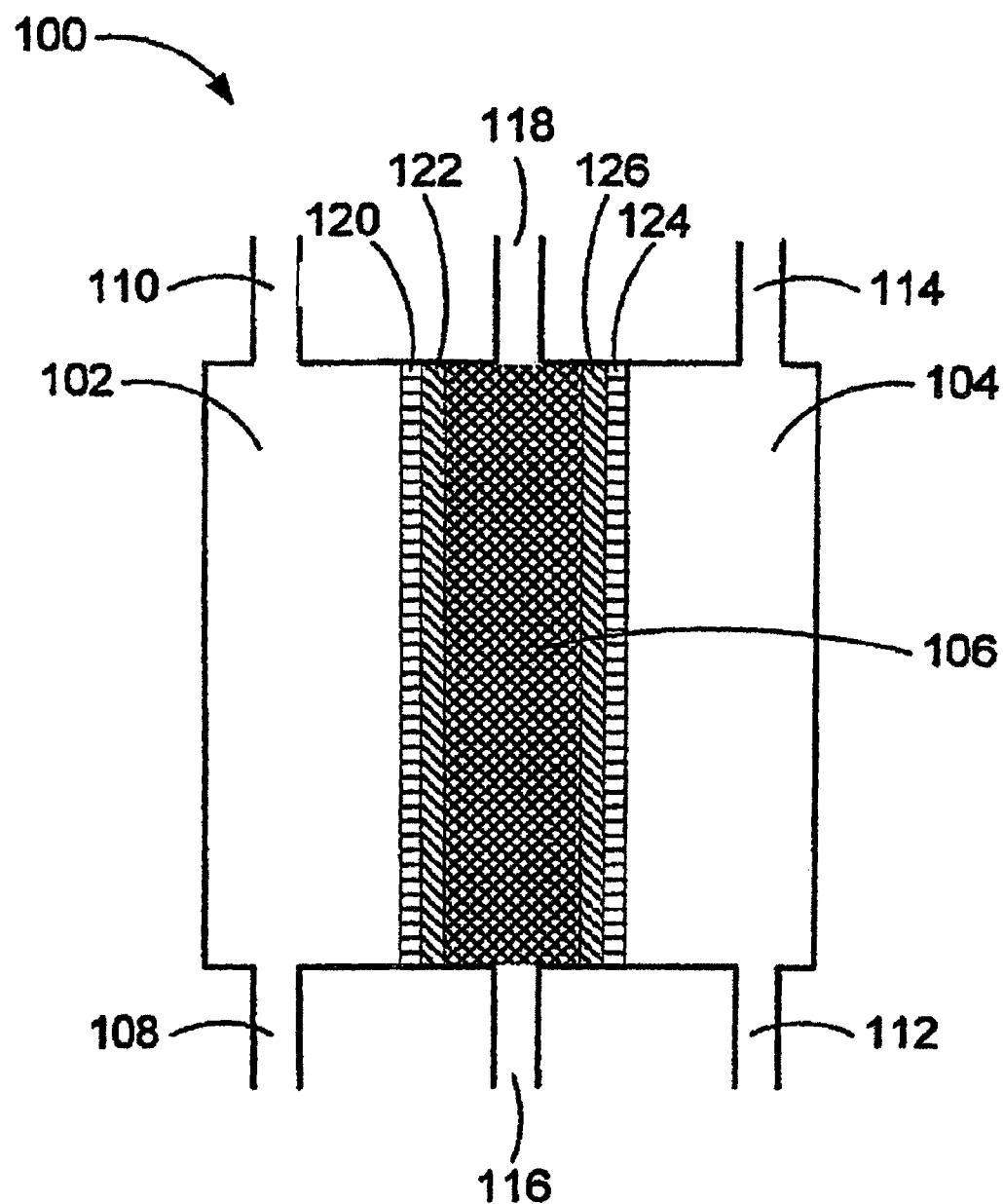
FIG. 1 is a schematic diagram of a three-chambered electrolysis cell for producing an oxidative reductive potential water solution for use in accordance with the invention.

The invention provides for methods of treating a skin ulcer in a patient comprising administering an oxidative reductive potential (ORP) water solution to the patient in an amount effective to treat the skin ulcer, wherein the solution has a pH of about 6.4 to about 7.8 and is stable for at least about one week. Preferably, the ORP water solution is stable for at least about two months and more preferably for at least about one year. The ORP water solution preferably has a pH of about 7.4 to about 7.6

The ORP water solution used in accordance with the invention may comprise anode water and cathode water. Preferably, the cathode water is present in the ORP water solution in an amount of from about 10% by volume to about 50% by volume of the solution. More preferably, the cathode water is present in an amount of from about 20% by volume to about 40% by volume of the solution. Alternatively, the anode water is present in the ORP water solution in an amount of from about 50% by volume to about 90% by volume of the solution.

The ORP water solution used in accordance with the invention can comprise at least one free chlorine species. The free chlorine species can include hypochlorous acid, hypochlorite ions or a combination thereof. Preferably, the free chlorine species is hypochlorous acid. Other free chloride species may be present.

The ORP water solution used in accordance with the invention can be, for example, comprised of free chlorine species in an amount of from about 10 ppm to about 400 ppm. Preferably, the free chlorine species is present in an amount of from about 15 ppm to about 50 ppm. More preferably, the free chlorine species is selected from the following: hypochlorous acid present in an amount of from about 15 ppm to about 35 ppm, sodium hypochlorite present in an amount from about 25 ppm to about 50 ppm, or the combination of hypochlorous acid present in an amount of from about 15 ppm to about 35 ppm and sodium hypochlorite present in an amount from about 25 ppm to about 50 ppm.

The invention provides for methods of treating a skin ulcer in a patient by administering the ORP water solution in any suitable manner. For example, the ORP water may be administered to the patient by washing or irrigating the skin ulcer with the solution. Alternatively, the ORP water solution can be administered to the patient by soaking the skin ulcer in the solution. The skin ulcer can be soaked in the ORP water solution for any suitable length of time, generally for at least about one minute, and preferably for at least about two minutes.

In another embodiment, the ORP water solution can be administered to the patient by dressing the skin ulcer with a wound dressing saturated with the solution. The saturated wound dressing may be left in contact with the wound for a sufficient period of time to treat the wound. Preferably, the saturated wound dressing is changed periodically such as, for example, once a day or multiple times per day to provide a fresh dressing to the wound.

The invention further provides for a method of treating a skin ulcer comprising: (1) washing or irrigating the ulcer with an oxidative reductive potential (ORP) water solution; (2) soaking the ulcer in the ORP water solution; (3) dressing the ulcer with a wound dressing saturated with the ORP water solution, and, (4) optionally repeating steps (1)-(3). Additionally, a gel based on the ORP water solution technology could also be applied to dressings or gauzes for covering wounds. Steps (1)-(3) of the method may be repeated as often as necessary to treat the skin ulcer.

The skin ulcers may optionally be debrided either before or after the application of the ORP water solution to the wound. Preferably, the skin ulcer is debrided before applying the ORP water solution. The skin ulcer can also be debrided prior to the application of a wound dressing saturated with the ORP water solution.

Skin ulcers can be cleaned once a day by irrigation, washing, and/or soaking for the first 3-4 days to properly control the associated infection. The ulcers can be washed with soap and tap water, debrided, and sprayed with an ORP water solution once a day, b.i.d., t.i.d., q.i.d. or more frequently as needed. After cleaning, the ulcer can be soaked or otherwise moistened with the ORP water solution for any suitable period of time, generally from about 60 to about 120 minutes, preferably from about 15 to about 60 minutes, more preferably from about 5 to about 15 minutes. The ulcer may optionally be subject to further rising. Following the moistening of the skin ulcer, the wound is preferably covered up with a moistening gel (the active principle of which can be an ORP water solution) and a dry dressing is applied. The moistening gel can further comprise an ORP water solution. Optionally, this procedure is repeated once a day, b.i.d., t.i.d., q.i.d. or more frequently, for the first 72 hours of the treatment. Thereafter, it can be optionally repeated once every 3 to 4 days, according to the clinical evaluation.

The patient treated according to the invention can be a human or veterinary patient (e.g., a non-human mammal). The skin ulcers to which the ORP water solution is applied can be located anywhere on a patient, including without limitation, wherein the skin ulcer is located on the head, neck, upper extremity, hands, fingers, trunk, genitalia, lower extremity, foot, toes, paws, hooves or combinations thereof. Multiple skin ulcers on one patient can be treated at the same time.

The invention provides for the treatment of skin ulcers of any depth, shape or size. Skin ulcers suitable for treatment include, by way of example, ulcers limited to the superficial epidermis, ulcers which preserve the epidermal basal layer, ulcers penetrating the epidermis, ulcers involving the dermis, ulcers which penetrate through the dermis into the subcutaneous tissue, and ulcers which penetrate to deep tissues including muscle, fat, and bone. The skin ulcers can be any shape, for example, round, oval, linear, or irregularly shaped.

Skin ulcers having any suitable surface area can be treated including, for example, a surface area of at least about 1 mm$^2$, at least about 5 mm$^2$, at least about 1 cm$^2$ or at least about 2 cm$^2$.

The invention provides for methods of treating a skin ulcer in a patient, wherein the skin ulcer is caused by, for example, arterial insufficiency, venous insufficiency, lymphatic insufficiency, neuropathy, pressure, trauma or a combination thereof.

Various types of skin ulcers in a patient can be treated with the ORP water solution according to the invention. For example, the following skin ulcers are suitable for treatment: diabetic foot ulcer, ischemic ulcer, gangrenous ulcer, venous stasis ulcer, decubitus ulcer or traumatic ulcer. In addition, the invention provides for methods of treating skin ulcers in patients with arterial insufficiency wherein the arterial insufficiency is caused by, for example without limitation, atherosclerosis, hypertension, smoking, emboli, diabetes, arterial inflammation, graph-versus-host disease, Raynaud's Disease, Buerger Disease (Thromboangiitis Obliterans) or combinations thereof.

The invention further provides methods of treating skin ulcers in patients with venous insufficiency caused by, for example without limitation, congestive heart failure, phlebitis, blood clots, venous valvular abnormalities, hereditary factors or combinations thereof. Skin ulcers may also be treated in patients with intravascular blood flow abnormalities caused by, for example without limitation, Sickle Cell Anemia, hypercoagulable states, leukostasis, hypervisousity syndromes, DIC or combinations thereof.

The invention also provides for methods of treating skin ulcers in patients with lymphatic insufficiency wherein the lymphatic insufficiency is caused by, for example without limitation, tumor emboli, filarasis or combinations thereof. Similarly, the invention provides for methods of treating skin ulcers in patients with edema wherein the edma is caused by, for example without limitation, congestive heart failure, hepatic cirrhosis, the nephrotic syndrome, malnutrition or combinations thereof.

The invention includes methods for the treatment of pressure skin ulcers wherein the pressure ischemia results from the patient's immobility, paralysis, obesity or combinations thereof. The invention additionally provides for methods of treatment of skin ulcers in patients with neuropathies wherein the neuropathies are caused by, for example without limitation, diabetes, uremia, toxins, amyloid, multiple sclerosis, hereditary neuropathy or combinations thereof.

The invention also provides for methods of treating a skin ulcer in a patient, wherein the skin ulcer is caused by a metabolic disorder (such as, e.g., diabetes, gout), inflammatory condition (such as, e.g., lupus, mixed connective tissue disease, rheumatoid arthritis, any type of primary or secondary vasculitis, hypersensitivity reactions, erythema multiforme, bullous skin dieases, pemphigus vulgaris), infectious disease (such as, e.g., herpes, leprosy, varicella-zoster, sepsis), neoplasm (such as, e.g., skin caner, hemangiomas), degenerative disease (such as, e.g, scleroderma, morphea), hereditary disease (such as, e.g., Sickle Cell Anemia), trauma/environmental insults (such as, e.g., abrasions, radiation, post operative fistulas) or a combination thereof.

The method of the invention may be used to treat a patient having a single skin ulcer or multiple skin ulcers.

Skin ulcers can be treated with the ORP water solution in combination with other therapries in accordance with the invention. For example, without limitation, venous stasis leg ulcers can be treated by administering an ORP water solution as part of a comprehensive outpatient treatment which can include sclerotherapy in as many veins as needed. Following each sclerotherapy session, the patient can wear a Class 2 compression stocking to assist closure of the treated veins. The length of time the stocking needed to be worn varied from about three days to about three weeks depending on the size of the veins injected. Compressive bandage is optionally used. Saphenectomy, can also be performed in suitable patients.

The invention further provides for methods of treating a skin ulcer, wherein the skin ulcer is a foot ulcer in a diabetic patient. The invention provides for a method of treating a foot ulcer in a diabetic patient comprising: (1) debriding the ulcer; (2) washing or irrigating the ulcer with the ORP water solution; (3) soaking the ulcer in the solution for at least two minutes; (4) drying the ulcer for at least about two minutes; (5) dressing the ulcer with a wound dressing saturated with the solution; and (6) optionally repeating steps (1)-(5), wherein the ulcer is an infected Grade 2 or Grade 3 foot ulcer in a diabetic patient, said ulcer having a surface area of at least about 2.0 cm$^2$. Such a method for treating foot ulcer in a diabetic patient can comprise repeating steps (1)-(5) any suitable number of times until the ulcer is substantially healed. Preferably, steps (1)-(5) are repeated at least one time.

The invention provides for methods for decreasing the recurrence rate of a skin ulcer in a patient, methods for decreasing the likelihood of dehiscence of a skin ulcer in a patient, and methods for decreasing the likelihood of amputation resulting from a skin ulcer in a patient comprising treating a skin ulcer in a patient by administering an oxidative reductive potential (ORP) water solution.

In a further embodiment, the present invention is directed to a method for reducing the incidence of systemic inflammatory response syndrome (SIRS) resulting from a skin ulcer comprising administering an ORP water solution. The invention further includes a method for reducing the incidence of sepsis resulting from a skin ulcer comprising administering an ORP water solution. Systemic inflammatory response syndrome (SIRS), a syndrome that encompasses the features of systemic inflammation without end-organ damage or identifiable bacteria. SIRS is separate and distinct from sepsis, severe sepsis or septic shock. The key transition from SIRS to sepsis is the presence of an identified pathogen in the blood. The pathophysiology of SIRS includes, but is not limited to, complement activation, cytokine and arachidonic acid metabolites secretion, stimulated cell-mediated immunity, activation of the clotting cascades, and humoral immune mechanisms. The decrease in the incidence of SIRS or sepsis in accordance with the invention can by any amount, generally by at least about 10%, preferably by at least about 15%, more preferably by at least about 20%, as measured by the reduction in the incidence of SIRS or sepsis in ORP water solution-treated patients relative to povidone iodine-treated patients.

The invention further provides a method for reducing the microbial load of a skin ulcer in a patient comprising treating a skin ulcer in a patient by administering an ORP water solution.

The therapeutically effective amount administered to the patient, e.g., an animal, particularly a human, in the context of the present invention should be sufficient to effect a therapeutic or prophylactic response in the patient over a reasonable time frame. The dose can be readily determined using methods that are well known in the art. One skilled in the art will recognize that the specific dosage level for any particular patient will depend upon a variety of factors. For example, the dose can be determined based on the strength of the particular ORP water solution employed, the severity of the condition, the body weight of the patient, the age of the patient, the physical and mental condition of the patient, general health, sex, diet, and the like. The size of the dose also can be determined based on the existence, nature, and extent of any adverse side effects that might accompany the administration of a particular ORP water solution. It is desirable, whenever possible, to keep adverse side effects to a minimum.

Factors, which can be taken into account for a specific dosage can include, for example, bioavailability, metabolic profile, time of administration, route of administration, rate of excretion, pharmacodynamics associated with a particular ORP water solution in a particular patient, and the like. Other factors can include, e.g., the potency or effectiveness of the ORP water solution with respect to the particular condition to be treated, the severity of the symptoms presented prior to or during the course of therapy, and the like. In some instances, what constitutes a therapeutically effective amount also can be determined, in part, by the use of one or more of the assays, e.g., bioassays, which are reasonably clinically predictive of the efficacy of a particular ORP water solution for the treatment or prevention of a particular condition.

The ORP water solution of the present invention can be administered therapeutically, alone or in combination with one or more other therapeutic agents, to a patient, e.g., a human, e.g., to treat an existing condition. The ORP water solution of the present invention also can be administered prophylactically, alone or in combination with one or more other therapeutic agents, to a patient, e.g., a human, that has been exposed to one or more causative agents associated with the condition. For example, the ORP water solution of the invention can be suitably administered to a diabetic patient that has been exposed to one or more infection-causing microorganisms (e.g., viruses, bacteria and/or fungi) prophylactically to inhibit or decrease the likelihood of infection in a patient, or decrease the severity of an infection that develops as a result of such exposure. That is, the ORP water solution can prevent the development of an infection in contaminated, colonized or critically colonized skin ulcers.

One skilled in the art will appreciate that suitable methods of administering the ORP water solution of the present invention are available, and, although more than one route of administration can be used, a particular route can provide a more immediate and more effective reaction than another route. The therapeutically effective amount can be the dose necessary to achieve an "effective level" of the ORP water solution in an individual patient. The therapeutically effective amount can be defined, for example, as the amount required to be administered to an individual patient to achieve a blood level, tissue level, and/or intracellular level of the ORP water of the present invention to prevent or treat the condition in the patient.

When the effective level is used as a preferred endpoint for dosing, the actual dose and schedule can vary depending, for example, upon interindividual differences in pharmacokinetics, distribution, metabolism, and the like. The effective level also can vary when the ORP water solution of the present invention is used in combination with one or more therapeutic agents other than the ORP water solution of the present invention, e.g., one or more anti-infective agents, one or more "moderating," "modulating" or "neutralizing agents," e.g., as described in U.S. Pat. Nos. 5,334,383 and 5,622,848, one or more anti-inflammatory agents, and the like.

An appropriate indicator can be used for determining and/or monitoring the effective level. For example, the effective level can be determined by direct analysis (e.g., analytical chemistry) or by indirect analysis (e.g., with clinical chemistry indicators) of appropriate patient samples (e.g., blood and/or tissues). The effective level also can be determined, for example, by direct or indirect observations such as, e.g., the concentration of urinary metabolites, changes in markers associated with the condition (e.g., viral count in the case of a viral infection), histopathology and immunochemistry analysis, decrease in the symptoms associated with the conditions, and the like.

The ORP water solution used in accordance with the present invention can be administered using any suitable method of administration known in the art. The ORP water solution used in accordance with the present invention can be administered in combination with one or more pharmaceutically acceptable carriers, vehicles, adjuvants, excipients, or diluents, which are known in the art. An ORP water solution used in accordance with the invention can also be the active principle of a gel, ointment, or the like. One skilled in the art can easily determine the appropriate formulation and method of administration for administering the ORP water in accordance with the present invention. Any necessary adjustments in dose can be readily made by a skilled practitioner to address the nature or severity of the condition being treated in view of other factors, such as, e.g., side effects, changes in the patient's overall condition, and the like.

The ORP water solution administered in accordance with the present invention also can be used as the irrigation solution for negative pressure devices that are used to reduce edema and increase the blood flow. Suitable negative pressure devices can include, e.g., one or more vacuum assisted wound closure devices such as, e.g., the V.A.C.® and V.A.C.® Instill™ devices sold in the United States by Kinetic Concepts, Inc. It is believed that the ORP water solution can act synergistically with the device by controlling the inflammatory-allergic process while reducing the microbial load. Thus the device may be applied to the open ulcer with intermittent or continuous irrigation to treat or prevent tissue infection or necrosis in accordance with the present invention.

The ORP water solution administered in accordance with the present invention also can be used as the irrigation solution for hydrosurgery devices that are used to debride skin ulcers. Suitable hydrosurgery devices can include, for example, the VersaJet devices sold in the United States by Smith and Nephew, Debritom in Europe by Medaxis, JetOx in the United States and Europe by DeRoyal or PulsaVac in Italy. It is believed that the ORP water solution can act synergistically with the device by reducing the microbial load in the wound and by avoiding the formation of infectious mists during the debridement procedure. Thus the device may be used to debride the ulcer with continuous irrigation, reduce the infection process and avoid the formation of infectious mists in accordance with the present invention.

Optionally, several adjuvant therapies can also be utilized in accordance with the invention including bioengineered skin (Apligraf, Organogenesis, Inc., Canton), acellular skin substitutes (Oasis Wound Matrix, Healthpoint), ultrasonic application of ORP water solutions, and local oxygen replacement or hyperbaric oxygen treatment (such as, e.g., hyperbaric boots, the Vent-Ox System).

Preferably, the ORP solution is administered to as a liquid or a gel, e.g., so as to contact the skin ulcer in a patient. The ORP solution of the present invention also can be administered as a steam or a spray. In addition, the ORP water solution of the present invention can be administered by aerosolization, nebulization or atomization. When the ORP water solution of the invention is administered by aerosolization, nebulization or atomization, it is preferably administered in the form of droplets having a diameter in the range of from about 0.1 micron to about 100 microns, preferably from about 1 micron to about 10 microns.

Exemplary nebulizers are described in U.S. Pat. Nos. 5,312,281, 5,287,847, and 6,598,602. U.S. Pat. No. 5,312,281 describes an ultrasonic wave nebulizer, which atomizes water or liquid at low temperature and reportedly can adjust the size of mist. In addition, U.S. Pat. No. 5,287,847 describes a pneumatic nebulizing apparatus with scalable flow rates and output volumes for delivering a medicinal aerosol to neonates, children and adults. Further, U.S. Pat. No. 5,063,922 describes an ultrasonic atomizer.

The method of the present invention also can be used for the prevention or treatment of an infection, which is treatable with the ORP water solution of the present invention. The infection can be caused by one or more infectious pathogens such as, for example, infectious microorganisms. Such microorganisms can include, for example, viruses, bacteria, and fungi. The viruses can include, e.g., one or more viruses selected from the group consisting of the herpes viruses, pox viruses, and papilloma viruses. The bacteria can include, e.g., one or more bacteria selected from the group consisting of *Escherichia coli, Pseudomonas aeruginosa, Staphylococcus aureus*, and *Mycobaterium tuberculosis*. The fungi can include, e.g., one or more fungi selected from the group consisting of *Candida albicans, Histoplasma capsulatum, Aspergillus* spieces, and dermatophytes.

The present invention additionally provides a method of treating impaired or damaged tissue, such as, e.g., a necrotic skin ulcer bed, which method comprises contacting the impaired or damaged tissue with a therapeutically effective amount of the ORP water solution of the present invention. Any suitable method can be used for contacting the impaired or damaged tissue, so as to treat the impaired or damaged tissue in accordance with the present invention. For example, the impaired or damaged tissue can be treated in accordance with the invention by irrigating the tissue with the ORP water solution of the invention, so as to contact the impaired or damaged tissue with the ORP water. Alternatively (and additionally), the ORP water solution of the present invention can be administered as a steam or a spray, or by aerosolization, nebulization or atomization, as described herein, so as to contact the impaired or damaged tissue with the ORP water.

The method of the present invention can be used in the treatment of tissues, which have been impaired or damaged, e.g., by surgery. For instance, the method of the present invention can be used for treating tissues, which have been impaired or damaged by an incision or that have left a fistula. In addition, the method of the present invention can be used for treating tissues, which have been impaired or damaged by oral surgery, graft surgery, implant surgery, transplant surgery, cauterization, amputation, radiation, chemotherapy, and combinations thereof. The oral surgery can include, for example, dental surgery such as, e.g., root canal surgery, tooth extraction, gum surgery, and the like.

The method of the present invention also includes treating tissues, which have been impaired or damaged by one or more burns, cuts, abrasions, scrapes, rashes, ulcers, puncture wounds, combinations thereof, and the like, which are not necessarily caused by surgery. The method of the present invention also can be used for treating impaired or damaged tissue, which is infected, or tissue impaired or damaged due to infection. Such infection can be caused by one or more infectious pathogens, such as, e.g., one or more microorganisms selected from the group consisting of viruses, bacteria, and fungi, as described herein.

The ORP water solution administered in accordance with the present invention also can be used for disinfecting a surface, including a biologic surface, e.g., skin, which method comprises contacting the surface with an anti-infective amount of the ORP water solution of the present invention. In accordance with the method of the present invention, the surface can be contacted using any suitable method. For example, the surface can be contacted by irrigating the surface with the ORP water solution of the invention, so as to disinfect the surface in accordance with the invention. Additionally, the surface can be contacted by applying the ORP water solution of the present invention to the surface as a steam or a spray, or by aerosolization, nebulization or atomization, as described herein, so as to disinfect the surface in accordance with the invention. Further, the ORP water solution of the present invention can be applied to the surface with a cleaning wipe, as described herein. By disinfecting a surface in accordance with the present invention, the surface may be cleansed of infectious microorganisms, thereby, e.g., decreasing the likelihood of infection or other complications (e.g., recurrence, dehiscence, and/or amputation) associated with, e.g., foot ulcers in diabetic patients. Alternatively (or additionally), the ORP water solution of the present invention can be applied to the surface to provide a barrier to infection, thereby disinfecting a surface in accordance with the present invention. The ORP water solution can also be used to disinfect or maintain the sterility of the instruments throughout long surgeries.

The ORP water solution can be used for disinfecting a surface, which is biological, inanimate, or a combination thereof. Biological surfaces can include, for example, tissues within one or more body cavities such as, for example, the oral cavity, the sinus cavity, the cranial cavity, the abdominal cavity, and the thoracic cavity. Tissues within the oral cavity include, e.g., mouth tissue, gum tissue, tongue tissue, and throat tissue. The biological tissue also can include skin, muscle tissue, bone tissue, organ tissue, mucosal tissue, acellular and cellular-skin substitutes, other bioengineered tissues, skin grafts, embryonic and adult stem cells or differentiated cells (e.g. fibroblasts, keratynocytes), and combinations thereof. Inanimate surfaces include, for example, surgically implantable devices, prosthetic devices, and medical devices, as well as the surfaces of internal organs, viscera, muscle, and the like, which may be exposed during surgery.

For topical administration, the ORP water solution can be administered alone or in combination with a carrier, e.g., a thickening agent to provide enhanced efficacy.

The amount of water present the formulations of the invention is generally from about 10% by weight to about 95% by weight, based on the weight of the formulation. Preferably, the amount of water present is from about 50% by weight to about 90% by weight.

It has been found that the ORP water solution administered in accordance with the invention is virtually free of toxicity to normal tissues and normal mammalian cells. The ORP water solution administered in accordance with the invention causes no significant decrease in the viability of eukaryotic cells, no significant increase in apoptosis, no significant acceleration of cell aging and/or no significant oxidative DNA damage in mammalian cells. The non-toxicity is particularly advantageous, and perhaps even surprising, given that the disinfecting power of the ORP water solution administered in accordance with the invention is roughly equivalent to that of hydrogen peroxide, yet is significantly less toxic than hydrogen peroxide is to normal tissues and normal mammalian cells. These findings demonstrate that the ORP water solution administered in accordance with the present invention is safe for use, e.g., in mammals, including humans.

For the ORP water solution administered in accordance with the invention, the cell viability rate is preferably at least about 65%, more preferably at least about 70%, and still more preferably at least about 75% after an about 30 minute exposure to the ORP water solution. In addition, the ORP water solution administered in accordance with the invention preferably causes only up to about 10% of cells, more preferably only up to about 5% of cells, and still more preferably only up to about 3% of cells to expose Annexin-V on their cellular surfaces when contacted with the ORP water solution for up to about thirty minutes or less (e.g., after about thirty minutes or after about five minutes of contact with the ORP water solution). Further, the ORP water solution administered in accordance with the invention preferably causes less than about 15% of cells, more preferably less than about 10% of cells, and still more preferably less than about 5% of cells to express the SA-β-galactosidase enzyme after chronic exposure to the OPR water solution. The ORP water solution administered in accordance with the invention preferably causes caused the same fraction of the oxidative DNA adduct formation caused by saline solution, e.g., less than about 20% of the oxidative DNA adduct formation, less than about 10% of the oxidative DNA adduct formation, or about 5% or less of the oxidative DNA adduct formation normally caused by hydrogen peroxide in cells treated under equivalent conditions.

The ORP water solution administered in accordance with the invention produces no significant RNA degradation. Accordingly, RNA extracted from human cell cultures after an about 30 minutes exposure to the ORP water solution or r at about 3 hours after an about 30 minute-exposure, and analyzed by denaturing gel electrophoresis, will typically show no significant RNA degradation and will typically exhibit two discreet bands corresponding to the ribosomal eukaryotic RNAs (i.e. 28S and 18S) indicating that the ORP water solution administered in accordance with the invention leaves the RNA substantially intact. Similarly, RNA extracted from human cell cultures after about 30 minutes of exposure to the ORP water solution or after about 3 hours of exposure, can be subjected reverse transcription and amplification (RT-PCR) of the constitutive human GAPDH (Glyceraldehyde-3-phosphate dehydrogenase) gene and result in a strong GAPDH band on gel electrophoresis of the RT-PCR products. By contrast, cells treated with HP for a similar period show significant RNA degradation and little if any GAPDH RT-PCR product.

Surprisingly, it has been found that the ORP water solution administered in accordance with the invention is a highly effective inhibitor of mast cell degranulation, one of the primary inflammation-causing biological cascades. The ORP water solution administered in accordance with the invention inhibits degranulation of mast cells regardless of whether they are activated with an antigen or a calcium ionophore. Also surprisingly, it has been found that the ORP water solution administered in accordance with the present invention non-selectively inhibits the secretion of histamine and pro-inflammatory cytokines in mast cells. For example, the ORP water solution of the present invention can inhibit the secretion of, e.g., TNF-α and MIP1-α in mast cells. It is believed that the ORP water solution administered in accordance with the invention also can inhibit the secretion of pro-inflammatory cytokines in other cytokine-secreting cells. These findings demonstrate that the ORP water solution administered in accordance with the present invention should exhibit broad anti-allergic and anti-inflammatory efficacy, which is desirable for treating or preventing the establishment to SIRS and multi-organ failure that worsens the prognosis in patients with infected skin ulcers.

ORP water solution can be administered as a formulation for topical administration according to the present invention further comprises a thickening agent. Any suitable thickening agent may be used to produce a formulation having the desired viscosity which is generally greater than the ORP water solution alone. The thickening agent utilized is preferably compatible with the ORP water solution and other optional components in the formulation. Suitable thickening agents include, but are not limited to, polymers and hydroxyethylcellulose. Suitable polymers may be homopolymers or copolymers and are optionally crosslinked. Other suitable thickening agents are generally known in art (see, e.g., *HANDBOOK OF COSMETIC AND PERSONAL CARE ADDITIVES*, 2nd ed., Ashe et al. eds. (2002), and *HANDBOOK OF PHARMACEUTICAL EXCIPIENTS*, 4th ed., Rowe et al. eds. (2003)).

In one embodiment, the thickening agent is selected from the group consisting of acrylic acid-based polymers, which can include high molecular weight, crosslinked, acrylic acid-based polymers, e.g., having the following general structure:

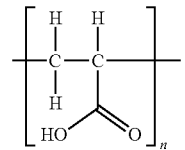

Such polymers are sold under the tradename Carbopol® by Noveon. Carbopol® polymers are generally supplied as rheology modifiers for use thickeners, suspending agents, and stabilizers in a variety of personal care products, pharmaceuticals, and household cleaners. Carbopol® polymers may be used in either solid (e.g., powder) or liquid form.

The acrylic acid-based polymers suitable for use in the invention may be homopolymers or copolymers. Suitable homopolymers may be crosslinked, preferably with allyl sucrose or allylpentaerythritol. Suitable copolymers of acrylic acid can be modified by long chain ($C_{10}$-$C_{30}$) alkyl acrylates and can be crosslinked, e.g., with allylpentaerythritol.

Carbopol® polymers are preferably neutralized in order to achieve maximum viscosity. As supplied, Carbopol® polymers can exist as dry, tightly coiled acidic molecules, held in a coiled structure by hydrogen bonds. Once dispersed in water, or another solvent, such polymer can begin to hydrate and partially uncoil. One way to achieve maximum thickening from Carbopol® polymers is by converting the acidic polymer into a salt. This is easily achieved by neutralizing with a common base such as sodium hydroxide (NaOH) or triethanolamine (TEA) to "uncoil" the long chain polymerand provide an effective thickening form.

Suitable thickening agents preferably will yield the desired viscosity for the formulation, as well as other characteristics, such as appearance, shear resistance, ion resistance, and thermal stability. For example, Carbopol® 934 is preferred for a formulation that is either a suspension or emulsion (rather than a clear gel) with a viscosity greater than 3000 centipoise (cps). Carbopol® 974P may alternatively be used for its advantageous bioadhesive properties.

Any suitable amount of a thickening agent can be included in the formulation to yield the desired viscosity for the formulation. Generally, the amount of thickening agent can be from about 0.1% by weight to about 50% by weight, based on the weight of the formulation. Preferably, the amount of thickening agent is from about 0.1% to about 10% by weight.

The amount of thickening agent also can be based on the volume of the ORP water solution is, e.g., from about 0.1% weight/volume (mg/mL) to about 50% weight/volume (mg/mL). In one embodiment, the amount of thickening agent is from about 0.1% w/v to about 10% w/v.

Exemplary formulations can include of thickening agent from about 0.1 g/250 mL to about 50 mg/250 mL of the ORP water solution, from about 1 mg/250 mL to about 20 mg/250 mL of the ORP water solution or from about 3 mg/250 mL to about 15 mg/250 mL of the ORP water solution.

When acrylic acid-based polymers are used at low concentrations, the formulation can flow easily with a slippery feel. At higher concentrations of such theckness, the formulation can have a high viscosity and can be pseudoplastic and resistant to flow. When shear force is applied by a mixer or pump, the apparent viscosity can be reduced, and the formulation can be pumped.

The formulation of the invention may optionally include a neutralizing agent. Any suitable neutralizing agent may be used to yield the desired pH of the formulation. Suitable neutralizing agents include, for example, sodium hydroxide, triethanolamine, ammonia, potassium hydroxide, L-arginine, AMP-95, Neutrol TE, Tris Amino, Ethomeen, di-isopropanolamine, and tri-isopropanolamine. Other neutralizing agents are generally known in the art (see, e.g., *HANDBOOK OF COSMETIC AND PERSONAL CARE ADDITIVES*, 2nd ed., Ashe et al. eds. (2002), and *HANDBOOK OF PHARMACEUTICAL EXCIPIENTS*, 4th ed., Rowe et al. eds. (2003)). Suitable neutralizing agents may be either in liquid or solid form.

Preferably, the neutralizer triethanolamine used when the thickening agent is an acrylic acid-based polymer such as Carbopol®. The neutralizing agent converts the formulation into a gel.

Any suitable amount of neutralizing agent may be included in the formulation of the invention. Generally, the amount of neutralizing agent is from about 0.1% by weight to about 50% by weight, based on the weight of the formulation. Preferably, the amount of neutralizing agent is from about 0.1% to about 10% by weight, based on the weight of the formulation. On a volume basis, the amount of neutralizing agent can be present in an amount of about 1% to about 50% by volume, based on the volume of the ORP water solution.

When added in liquid form, the neutralizing can be added in an amount of from about 1 mL/250 mL to about 100 mL/250 mL of the ORP water solution. Preferably, the amount of neutralizing agent is from about 10 mL/250 mL to about 90 mg/250 mL of the ORP water solution.

The formulation may further contain additional components such as colorants, fragrances, buffers, physiologically acceptable carriers and/or excipients, and the like. Examples of suitable colorants include, but are not limited to, titanium dioxide, iron oxides, carbazole violet, chromium-cobalt-aluminum oxide, 4-Bis[(2-hydroxyethyl)amino]-9,10-anthracenedione bis(2-propenoic)ester copolymers, and the like. Any suitable fragrance can be used.

The formulation of the invention may be prepared by any suitable means. The components of the formulation, such as the ORP water solution and thickening agent, may be mixed together in any manner to yield a homogenous mixture. Preferably, the components are mixed together for several minutes using an electric mixture or other suitable device to ensure uniformity. The components of the formulation are generally mixed at from about 400 rpm to about 1000 rpm, preferably from about 500 rpm to about 800 rpm, and more preferably from about 500 rpm to about 600 rpm.

The formulation is mixed for a sufficient period of time to yield a homogenous mixture, generally from about 1 minute to about 10 minutes after all of the components have been combined.

When the thickening agent is in the form of a power, it may first be sieved to break up large agglomerates to allow for the preparation of a homogenous formulation.

A neutralizing agent, such as triethanolamine, may subsequently be added to the formulation containing the ORP water solution and thickening agent. As noted above, the addition of triethanolamine may allow the thickening agent, such as Carbopol®, to uncoil and, thus, yield a formulation having the desired viscosity.

A colorant or fragrance may also be added to the mixture either before or after the thickening agent, such as Carbopol®, is dissolved into the ORP water, but before the neutralization step.

The chemical properties of the ORP water solution in the formulation of the invention are typically the same as those of the ORP water solution alone. The properties of the ORP water solution preferably remain even after the addition of a thickening agent and optional neutralizing agent. For example, the pH and disinfecting power of the ORP water solution itself and the formulation containing the ORP water solution preferably are generally the same. Most preferably, all of the clinically relevant characteristics of the ORP water solution described herein apply to the formulation of the invention.

For example, the formulation of the invention is preferably stable for at least about twenty-hours, and preferably at least about two days. More preferably, the formulation is stable for at least about one week (e.g., one week, two weeks, three weeks, four weeks, etc.), and even more preferably at least about two months.

The pH of the formulation is preferably from about 6 to about 8. More preferably from about 6.2 and about 7.8, and most preferably from about 7.4 and about 7.6.

The formulation can exist in any form suitable for topical administration to a patient including, but is not limited to, gel, lotion, cream, paste, ointment, and the like, which forms are known in the art (see, e.g., *MODERN PHARMACEUTICS*, 3rd ed., Banker et al. ed. (1996)). Gels are typically a semi-solid emulsion or suspension that has a three-dimensional structure. In another embodiment, the formulation is in the form of a gel.

Pastes are generally semisolid suspensions that often contain a large portion of solids (e.g., about 20% to about 50%) dispersed in an aqueous or fatty vehicle. Lotions are typically liquid emulsions containing a water-based vehicle and volatiles (more than about 50%) and that have a sufficiently low viscosity (less than 30,000 cps) to be poured. Ointments and creams are preferably semisolid emulsions or suspensions that may contain hydrocarbons or polyethylene glycols as part of the carrier along with other volatile components.

When the formulation of the invention is in the form of a gel, the viscosity of the gel is preferably in the range of from about 10,000 to about 100,000 centipoise (cps) (e.g., about 15,000 cps, about 20,000 cps, about 25,000 cps, about 30,000 cps, about 35,000 cps, about 40,000 cps, about 45,000 cps, about 50,000 cps, about 55,000 cps, about 60,000 cps, about 65,000 cps, about 70,000 cps, about 75,000 cps, about 80,000 cps, about 85,000 cps, about 90,000 cps, about 95,000 cps, or ranges thereof or viscosities with the ranges of such values).

The pH of the gel is preferably in the range of from about 6.0 to about 8.0. Above this pH, the viscosity of the thickening agent, such as the Carbopol® polymer, may. Preferably, the pH of the gel is from about 6.4 to about 7.8, and more preferably from about 7.4 to about 7.6.

The formulation of the invention is suitable for topical administration to a patient, including a human and/or animal, to treat a variety of conditions. Specifically, the formulation may be applied to animals (e.g., mice, rats, pigs, cows, horses, dogs, cats, rabbits, guinea pigs, hamsters, birds) and humans. Topical administration includes application to the skin and biological tissues as well as other routes of administration.

Conditions in a patient that may be treated according to the invention include, for example, the following: surgical/open wound cleansing agent; skin pathogen disinfection (e.g., for bacteria, mycoplasmas, virus, fungi, prions); wound disinfection (e.g., battle wounds); wound healing promotion; burn healing promotion; treatment of skin fungi; psoriasis; athlete's foot; ear infections (e.g., swimmer's ear); traumatic wounds; acute, subchronic and chronic infections (e.g. diabetic foot infections being an example of the latter), pressure ulcers, derma-abrasion, debrided wounds, laser re-surfacing, donor sites/grafts, exuding partial and full thickness wounds, superficial injuries (lacerations, cuts, abrasions, minor skin irritations), any skin ulcer with acute or chronic inflammation or hypersensitivity, and other medical applications on or in the human or animal body. Ulcers treated according to the invention may or may not have abscesses, secretion or necrotic tissue present.

The ORP water solution administered in accordance with the invention may be used or applied in a therapeutically effective amount to provide the desired therapeutic effect on bacteria, viruses, and/or germs. A therapeutically effective amount can include to an amount of the formulation that results in an improvement of the condition being treated or to be prevented. For example, when used to treat an infection, a therapeutically effective amount can include an amount that is effective to reduce the extent of the infection and/or prevent further infection. As is appreciated by one skilled in the art, the efficacy of the formulation resulting from administering the formulation may be short-term (i.e., a few days) and/or long-term (e.g., months).

The ORP water solution or a formulation thereof can further be applied over a sufficient period of time, for example, about one, about two, several days, about one week, or several weeks, until the desired effect on the patient is observed.

The ORP water solution or a formulation thereof can be applied in any suitable manner. For example, a quantity of the ORP water solution or a formulation thereof can be applied to the surface of the patient to be treated and then evenly spread using the patient's own fingers. Alternatively, a health care provider may apply the formulation to the patient's tissue. A suitable implement, for example, a disposable wipe or cloth, may be used to apply the formulation.

The ORP water solution administered in accordance with the present invention can be produced by an oxidation-reduction process, e.g., by an electrolytic process or redox reaction, in which electrical energy is used to produce one or more chemical changes in an aqueous solution. Exemplary processes for preparing suitable ORP water solutions are described, e.g., in U.S. Patent Application Publication Nos. US 2005/0139808 and US 2005/0142157.

In the electrolytic process, electrical energy is introduced into and transported through water by the conduction of electrical charge from one point to another in the form of an electrical current. In order for the electrical current to arise and subsist there should be charge carriers in the water, and there should be a force that makes the carriers move. The charge carriers can be electrons, as in the case of metal and semiconductors, or they can be positive and negative ions in the case of solutions. A reduction reaction occurs at the cathode while an oxidation reaction occurs at the anode. At least some of the reductive and oxidative reactions that are believed to occur are described in International Application WO 03/048421 A1.

As used herein, water produced at an anode is referred to as anode water and water produced at a cathode is referred to as cathode water. Anode water typically contains oxidized species produced from the electrolytic reaction while cathode water typically contains reduced species from the reaction. Anode water generally has a low pH, typically of from about 1 to about 6.8. The anode water preferably contains chlorine in various forms including, for example, chlorine gas, chloride ions, hydrochloric acid and/or hypochlorous acid, or one or more precursors thereof. Oxygen in various forms is also preferably present including, for example, oxygen gas, and possibly one or more other oxidized water species formed during production (e.g., products of peroxides and/or ozone), or one or more precursors thereof. Cathode water generally has a high pH, typically from about 7.2 to about 11. Cathode water can contain hydrogen gas, hydroxyl radicals, and/or sodium ions.

The ORP water solution of the invention may be acidic, neutral or basic, and generally has a pH of from about 1 to about 14. At this pH, the ORP water solution can safely be applied in suitable quantities to hard surfaces without damaging the surfaces or harming objects, such as human skin, that comes into contact with the ORP water solution. Typically, the pH of the ORP water solution is from about 3 to about 8. More preferably, the pH of the ORP water solution is from about 6.4 to about 7.8, and most preferably, the pH is from about 7.4 to about 7.6.

The ORP water solution administered in accordance with the invention can have an oxidation-reduction potential of from about −1000 millivolts (mV) to about +1150 millivolts (mV). This potential is a measure of the tendency (i.e., the potential) of a solution to either accept or transfer electrons that are sensed by a metal electrode and compared with a reference electrode in the same solution. This potential may be measured by standard techniques including, for example, measuring the electrical potential in millivolts of the ORP water solution relative to standard reference such as, e.g., a silver/silver chloride electrode. The ORP water solution administered in accordance with the invention preferably has a potential of from about −400 mV to about +1300 mV. More preferably, the ORP water solution has a potential of from about 0 mV to about +1250 mV, and still more preferably from about +500 mV to about +1250 mV. Even more preferably, the ORP water solution administered in accordance with the present invention has a potential of from about +800 mV to about +1100 mV, and most preferably from about +800 mV to about +1000 mV.

Various ionic and other species may be present in the ORP water solution administered in accordance with the invention. For example, the ORP water solution may contain chlorine (e.g., free chlorine and, optionally, bound chlorine) and dissolved oxygen and, optionally, ozone and peroxides (e.g., hydrogen peroxide). The presence of one or more of these species is believed to contribute to at least the disinfectant ability of the ORP water solution to kill a variety of microorganisms, such as bacteria and fungi, as well as viruses.

Free chlorine typically includes, but is not limited to, hypochlorous acid (HClO), hypochlorite ions (ClO−) and sodium hypochlorite (NaOCl), other molecular or radical chlorine species, and precursors thereof. The ratio of hypochlorous acid to hypochlorite ion is dependent upon pH.

At a pH of 7.4, hypochlorous acid levels are typically from about 25 ppm to about 75 ppm. Temperature also impacts the ratio of the free chlorine component.

Bound chlorine typically refers to products of chlorine and nitrogen-containing compounds, e.g., products of chlorine and ammonia or organic amines (e.g., chloramines). Bound chlorine is optionally present in the ORP water solution, but is preferably present in an amount of less than about 20 ppm.

One or more chlorine species and oxygen, and, optionally, ozone and hydrogen peroxide can be present in the ORP water solution in any suitable amount. The levels of these components may be measured by any suitable method, including methods known in the art.

The total chlorine content, which includes both free chlorine and, optionally, bound chlorine, can be from about 10 parts per million (ppm) to about 400 ppm, e.g., from about 10 parts ppm to about 200 ppm, from about 20 ppm to about 150 ppm, from about 30 ppm to about 100 ppm, from about 30 to about 80 ppm, or, e.g., from about 50 ppm to about 200 ppm or from about 80 ppm to about 150 ppm.

The chlorine content may be measured by methods known in the art, such as the DPD colorimeter method (Lamotte Company, Chestertown, Md.) or other known methods such as, e.g., methods established by the Environmental Protection Agency. In the DPD colorimeter method, a yellow color is formed by the reaction of free chlorine with N,N-diethyl-p-phenylenediamine (DPD) and the intensity is measured with a calibrated calorimeter that provides the output in parts per million. Further addition of potassium iodide turns the solution a pink color to provide the total chlorine value. The amount of bound chlorine present can be determined by subtracting free chlorine from the total chlorine.

The total amount of oxidizing chemical species present in the ORP water solution is preferably in the range of about 2 millimolar (mM) and can include the aforementioned chlorine species, one or more additional oxidized water species (e.g., one or more oxygen species), and additional species that may be difficult to measure such as Cl–, ClO3, Cl2–, and ClOx.

The ORP water solutions administered in accordance with the invention preferably comprises one or more oxidized water species which can yield free radicals (such as, e.g., hydroxyl radicals) on exposure to iron. The ORP water can optionally include one or more chemical compounds generated during the production thereof such as, e.g., sodium hydroxide (NaOH), chlorine dioxide (ClO2), peroxides (e.g., hydrogen peroxide (H2O2), and ozone (O3) although, sodium hydroxide, chlorine dioxide, hydrogen peroxide, and ozone may potentially react with hypocholrite resulting in their consumption and the production of other chemical species.

The ORP water solution of the invention is generally stable for at least about twenty-four hours, and typically at least about two days. More typically, the water solution is stable for at least about one week (e.g., about one week, about two weeks, about three weeks, about four weeks, etc.), and preferably at least about two months. More preferably, the ORP water solution is stable for at least about six months after its preparation. Even more preferably, the ORP water solution is stable for at least about one year, and most preferably for at least about three years.

Conventional ORP water solutions have an extremely limited shelf-life, usually only a few hours. As a result of this short lifespan, using conventional ORP water solutions requires the production to take place in close proximity to the point of use. From a practical standpoint, this means that the facility, e.g., a healthcare facility such as a hospital, must purchase, house and maintain the equipment necessary to produce conventional ORP water solution. Additionally, conventional manufacturing techniques have not been able to produce sufficient commercial-scale quantities to permit widespread use, e.g., as a general disinfecting agent for healthcare facilities.

Unlike conventional ORP water solutions, the ORP water solution administered in accordance with the invention is stable for at least about twenty-hours after its preparation. In addition, the ORP water solution administered in accordance with the invention is generally environmentally safe and, thus, avoids the need for costly disposal procedures.

Preferably, the ORP water solution administered in accordance with the invention is stable for at least about one week (e.g., about one week, about two weeks, about three weeks, about four weeks, etc.), and more preferably at least about two months. Still more preferably, the ORP water solution administered in accordance with the invention is stable for at least about six months. Even more preferably, the ORP water solution administered in accordance with the invention is stable for at least about one year, and most preferably is stable for more than about one year, e.g., at least about two years or at least about three years.

Stability can be measured based on the ability of the ORP water solution to remain suitable for one or more uses, for example, inhibiting mast cell degranulation, inhibiting histamine and cytokine secretion, decontamination, disinfection, sterilization, anti-microbial cleansing, and wound cleansing, for a specified period of time after its preparation under normal storage conditions (e.g., room temperature). The stability of the ORP water solution administered in accordance with the invention also can be measured by storage under accelerated conditions, e.g., from about 30° C. to about 60° C., wherein the ORP water solution preferably is stable for up to about 90 days, and more preferably for up to about 180 days.

Stability also can be measured based on the concentration over time of one or more species (or precursors thereof) present in solution during the shelf-life of the ORP water solution. Preferably, the concentrations of one or more species, e.g., free chlorine, hypochlorous acid and one or more additional oxidized water species are maintained at about 70% or greater of their initial concentration for at least about two months after preparation of the ORP water solution. More preferably, the concentration of one of more of these species is maintained at about 80% or greater of their initial concentration for at least about two months after preparation of the ORP water solution. Still more preferably, the concentration of one or more of such species is maintained at about 90% or greater, and most preferably is maintained at about 95% or greater, of their initial concentration for at least about two months after preparation of the ORP water solution.

Stability also can be determined based on the reduction in the amount of organisms present in a sample following exposure to the ORP water solution. Measuring the reduction of organism concentration can be made on the basis of any suitable organism including, e.g., bacteria, fungi, yeasts, or viruses. Suitable organisms can include, e.g., *Escherichia coli, Staphylococcus aureus, Candida albicans*, and *Bacillus athrophaeus* (formerly *B. subtilis*).

Stability also can be determined based on the reduction in the amount of endotoxins (e.g. lipopolysacharides), growth factors, cytokines and other proteins and lipids present in a sample following exposure to the ORP water solution.

The ORP water solution administered in accordance with the invention can function as a low-level disinfectant capable of an about four log (104) reduction in the concentration of live microorganisms, and also can function as a high-level disinfectant capable of an about six log (106) reduction in concentration of live microorganisms. Preferably, the ORP water solution administered in accordance with the invention is capable of yielding at least about an about four log (104) reduction in total organism concentration, following exposure for one minute when measured at least about two months after preparation of the solution. More preferably, the ORP water solution is capable of an about $10^4$-about $10^6$ reduction of organism concentration when measured at least about six months after preparation of the solution. Still more preferably, the ORP water solution is capable of an about $10^4$-about $10^6$ reduction of organism concentration when measured at least about one year after preparation of the ORP water solution, and most preferably when measured more than about one year, e.g., at least about two years or at least about three years, after preparation of the ORP water solution.

For instance, the ORP water solution is capable of at least about five log (105) reduction in the concentration of a sample of live microorganism selected from the group consisting of *Pseudomonas aeruginosa, Escherichia coli, Enterococcus hirae, Acinetobacter baumannii, Acinetobacter* species, *Bacteroides fragilis, Enterobacter aerogenes, Enterococcus faecalis,* Vancomycin Resistant-*Enterococcus faecium* (VRE, MDR), *Haemophilus influenzae, Klebsiella oxytoca, Klebsiella pneumoniae, Micrococcus luteus, Proteus mirabilis, Serratia marcescens, Staphylococcus aureus, Staphylococcus epidermidis, Staphylococcus haemolyticus, Staphylococcus hominis, Staphylococcus saprophyticus, Streptococcus pneumoniae, Streptococcus pyogenes, Candida albicans* and *Candida tropicalis*, within 30 seconds of exposure, when measured at least two months after preparation of the ORP water solution.

In one embodiment, the ORP water solution administered in accordance with the invention can reduce a sample of live microorganisms including, but not limited to, *Escherichia coli, Pseudomonas aeruginosa, Staphylococcus aureus* and *Candida albicans*, from an initial concentration of between about 1×106 and about 1×108 organisms/ml to a final concentration of about zero organisms/ml within about one minute of exposure when measured at least about two months after preparation of the ORP water solution. This corresponds to from about a six log (106) to about an eight log (108) reduction in organism concentration. Preferably, the ORP water solution is capable of achieving an about 106-about 108 reduction of *Escherichia coli, Pseudomonas aeruginosa, Staphylococcus aureus* or *Candida albicans* organisms when measured at least about six months after preparation, and more preferably when measured at least about one year after preparation.

Alternatively, the ORP water solution administered in accordance with the present invention can produce about a six log (106) reduction in the concentration of a spore suspension of *Bacillus* athrophaeus spores within about five minutes of exposure when measured at least about two months after preparation of the ORP water solution. Preferably, the ORP water solution administered in accordance with the invention can achieve about a 106 reduction in the concentration of *Bacillus athrophaeus* spores when measured at least about six months after preparation, and more preferably when measured at least about one year after preparation. The ORP water solution is further capable of an about four log (104) reduction in the concentration of a spore suspension of *Bacillus athrophaeus* spores within about thirty (30) seconds of exposure, when measured at least two months after preparation of the ORP water solution. Preferably, the ORP water solution is capable of achieving this reduction in the concentration of *Bacillus athrophaeus* spores when measured at least about six months after preparation, and more preferably at least one about year after preparation.

The ORP water solution is also capable of an about six log (106) reduction in the concentration of fungal spores, such as *Aspergillis niger* spores, within about five to about ten minutes of exposure, when measured at least two months after preparation of the ORP water solution. Preferably, the ORP water solution is capable of achieving this reduction in the concentration of fungal spores when measured at least six months after preparation, and more preferably at least one year after preparation.

The ORP water solution administered in accordance with the invention further can produce more than 3 log (103) reduction in the concentration of viruses, such as Human Immunodeficiency Virus (HIV) and adenovirus, after from an about five to an about ten minutes exposure when measured at least about two months after preparation of the ORP water solution. Preferably, the ORP water solution can achieve a >103 reduction in the concentration of viruses when measured at least about six months after preparation, and more preferably when measured at least about one year after preparation.

The ORP water solution administered in accordance with the invention further can completely inhibit the growth of *Mycobacterium bovis* with an about five minutes exposure when measured at least about two months after preparation of the ORP water solution. Preferably, the ORP water solution can achieve the total inhibition in the concentration of Mycobacteria when measured at least about six months after preparation, and more preferably when measured at least about one year after preparation.

In one embodiment, the ORP water solution of the invention comprises one or more chlorine species. Preferably, the chlorine species present is a free chlorine species. The free chlorine species may be selected from the group consisting of hypochlorous acid (HOCl), hypochlorite ions (OCl–), sodium hypochlorite (NaOCl), chloride ion (Cl–), dissolved chlorine gas (Cl2), and mixtures thereof.

The total amount of free chlorine species can be from about 10 parts per million (ppm) to about 400 ppm, e.g., from about 20 ppm to about 150 ppm, from about 30 ppm to about 100 ppm, from about 30 to about 80 ppm, or, e.g., from about 50 ppm to about 200 ppm, from about 80 ppm to about 150 ppm, from about 10 ppm and about 400 ppm, preferably from about 50 ppm and about 200 ppm, and most preferably from about 50 ppm and about 80 ppm. The amount of hypochlorous acid is in the generally from about 15 ppm and about 75 ppm, preferably from about 25 ppm and about 35 ppm. The amount of sodium hypochlorite is generally in the range of from about 25 ppm and about 50 ppm. Chlorine dioxide levels are optionally present at less than 5 ppm. In one embodiment, the ORP water solution includes one or more chlorine species or one or more precursors thereof and one or more additional oxidized water species or one or more precursors thereof, and, optionally, hydrogen peroxide, and is stable for at least about 24 hours, preferably for at least about one week, more preferably for at least about two months, and still more preferably for at least about six months after its preparation. Even more preferably, such ORP water solution is stable for at least about one year, and most preferably for more than about one year, e.g., at least about two years or at least about three years.

It is also preferred that the ORP water solution includes one or more chlorine species (e.g., hypochlorous acid and sodium hypochlorite) or one or more precursors thereof and one or more additional oxidized water species (e.g., oxygen) or one or more precursors thereof, and has a pH of from about 6 to about 8, more preferably from about 6.2 to about 7.8, and most preferably from about 7.4 to about 7.6. An exemplary ORP water solution administered in accordance with the present invention can comprise, e.g., from about 15 ppm to about 35 ppm hypochlorous acid, from about 25 ppm to about 50 ppm sodium hypochlorite, from about 1 ppm to about 4 ppm of one or more additional oxidized water species, a pH of from about 6.2 to about 7.8, and can be stable for at least about one week, e.g., at least about two months, at least about six months, at least about one year, or more than about one year, e.g., at least about two years or at least about three years.

In accordance with the present invention, a therapeutically effective amount of the ORP water solution can be administered alone or in combination with one or more additional therapeutic agents so as to treat or prevent peritonitis or so as to prevent the formation of adhesions or abscesses associated therewith. For example, the ORP water solution can be administered in conjunction with one or more additional therapeutic agents, e.g., one or more compounds selected from the group consisting of anti-infective agents (e.g., anti-bacterial agents (such as, e.g., antibiotics), anti-fungal agents and anti-viral agents), anti-inflammatory agents, recombinant proteins or antibodies, one or more synthetic drugs and combinations thereof. Administering such therapeutic agents in conjunction with the ORP water solution can include administering one or more of such additional agents, e.g., prior to, during (e.g., contemporaneously, by co-administration or in combination with), or following administration of the ORP water solution.

Suitable antibiotics can include, without limitation, penicillin, cephalosporins or other β-lactams, macrolides (e.g., erythromycin, 6-O-methylerythromycin, and azithromycin), fluoroquinolones, sulfonamides, tetracyclines, aminoglycosides, clindamycin, quinolones, metronidazole, vancomycin, chloramphenicol, antibacterially effective derivatives thereof, and combinations thereof. Suitable anti-infective agents also can include antifungal agents such as, for example, amphotericin B, fluconazole, flucytosine, ketoconazole, miconazole, derivatives thereof, and combinations thereof. Suitable anti-inflammatory agents can include, e.g., one or more anti-inflammatory drugs, e.g., one or more anti-inflammatory steroids or one or more non-steroidal anti-inflammatory drugs (NSAIDs). Exemplary anti-inflammatory drugs can include, e.g., cyclophilins, FK binding proteins, anti-cytokine antibodies (e.g. anti-TNF), steroids, and NSAIDs.

Organisms that can be controlled, reduced, killed or eradicated by treatment with the ORP water solution used in accordance with the invention include, e.g., *Pseudomonas aeruginosa, Escherichia coli, Enterococcus hirae, Acinetobacter baumannii, Acinetobacter* species, *Bacteroides fragilis, Enterobacter aerogenes, Enterococcus faecalis,* Vancomycin resistant-*Enterococcus faecium* (VRE, MDR), *Haemophilus influenzae, Klebsiella oxytoca, Klebsiella pneumoniae, Micrococcus luteus, Proteus mirabilis, Serratia marcescens, Staphylococcus aureus, Staphylococcus epidermidis, Staphylococcus haemolyticus, Staphylococcus hominis, Staphylococcus saprophyticus, Streptococcus pneumoniae, Streptococcus pyogenes, Salmonella choleraesuis, Shigella dysenteriae*, and other susceptible bacteria, as well as yeasts, e.g., *Trichophyton mentagrophytes, Candida albicans* and *Candida tropicalis*. The ORP water solution can also be used in accordance with the invention to control, reduce, kill or eradicate viruses including, e.g., adenovirus, human immunodeficiency virus (HIV), rhinovirus, influenza (e.g., influenza A), hepatitis (e.g., hepatitis A), coronavirus (responsible for, e.g., Severe Acute Respiratory Syndrome (SARS)), rotavirus, avian flu virus, respiratory syncytial virus, herpes simplex virus, varicella zoster virus, rubella virus, and other susceptible viruses.

In accordance with the invention, the ORP water solution can be administered alone or in combination with one or more pharmaceutically acceptable carriers, e.g., vehicles, adjuvants, excipients, diluents, combinations thereof, and the like, which are preferably compatible with one or more of the species that exist in the ORP water solution. One skilled in the art can easily determine the appropriate formulation and method for administering the ORP water solution used in accordance with the present invention. For instance, the use of a gel based formulation containing the ORP water solution can be used to maintain hydration of the peritoneal cavity while providing a barrier against microorganisms. Suitable gel formulations are described, e.g., in U.S. Patent Application Publication No. US 2005/0142157.

Any necessary adjustments in dose can be readily made by a skilled practitioner to address the nature and/or severity of the condition being treated in view of one or more clinically relevant factors, such as, e.g., side effects, changes in the patient's overall condition, and the like. For example, the ORP water solution can be formulated by combining or diluting the ORP water solution with about 25% (wt./wt. or vol./vol.) of a suitable carrier, about 50% (wt./wt. or vol./vol.) of a suitable carrier, about 75% (wt./wt. or vol./vol.) of a suitable carrier, about 90% (wt./wt. or vol./vol.) of a suitable carrier, about 95% (wt./wt. or vol./vol.) of a suitable carrier, or even with about 99% (wt./wt. or vol./vol.) or more of a suitable carrier. Suitable carriers can include, e.g., water (e.g., distilled water, sterile water, e.g., sterile water for injection, sterile saline and the like). Suitable carriers also can include one or more carriers described in U.S. patent application Ser. No. 10/916,278. Exemplary formulations can include, e.g., solutions in which the ORP water solution is diluted with sterile water or sterile saline, wherein the ORP water solution is diluted by about 25% (vol./vol.), by about 50% (vol./vol.), by about 75% (vol./vol.), by about 90% (vol./vol.), by about 95% (vol./vol.), or by 99% (vol./vol.) or more, depending on the therapeutic application and/or any other therapeutically relevant factors.

The ORP water solution could also include various amounts of ions and carbohydrates to make the solution hypo-, iso- or hyperosmolar for the purpose of compatibility with the body tissues, organs and cavities. Exemplary formulations can include, e.g., solutions in which the ORP water solution are added prior, during or after its production, sodium chloride and glucose to increase the osmolarity of the solution to be applied in the peritoneal cavity of a kidney patient. Alternatively, a final concentration of 0.9% sodium chloride could be attained in the ORP solution for make it iso-osmolar and compatible with parenteral injection.

The ORP water solution could also be treated as required for reducing the contents of pyrogens, endotoxins, or the like, that could be contaminating the solution.

Following its preparation, the ORP water solution can be transferred to one or more suitable containers, e.g., a sealed container for distribution and sale to end users such as, e.g., health care facilities including, e.g., hospitals, nursing homes, doctor offices, outpatient surgical centers, dental offices, and the like. Suitable containers can include, e.g., a sealed container that maintains the sterility and stability of the ORP water solution held by the container. The container can be constructed of any material that is compatible with the ORP water solution. Preferably, the container is generally non-reactive with one or more ions or other species present in the ORP water solution.

Preferably, the container is constructed of plastic or glass. The plastic can be rigid so that the container is capable of being stored on a shelf. Alternatively, the container can be flexible, e.g., a container made of flexible plastic such as, e.g., a flexible bag. Suitable plastics can include, e.g., polypropylene, polyester terephthalate (PET), polyolefin, cycloolefin, polycarbonate, ABS resin, polyethylene, polyvinyl chloride, and mixtures thereof. Preferably, the container comprises one or more polyethylenes selected from the group consisting of high-density polyethylene (HDPE), low-density polyethylene (LDPE), and linear low-density polyethylene (LLDPE). Most preferably, the container is constructed of high density polyethylene.

The container preferably has an opening to permit dispensing of the ORP water solution. The container opening can be sealed in any suitable manner. For example, the container can be sealed with a twist-off cap or stopper. Optionally, the opening can be further sealed with a foil layer.

The headspace gas of the sealed container may be air or other suitable gas that does not react with the ORP water solution or other components of a formulation containing the ORP water solution. Suitable headspace gases included nitrogen, oxygen, and mixtures thereof.

The ORP water solution administered in accordance with the invention can include a mixture of anode water (e.g., water produced in the anode chamber of an electrolytic cell) and cathode water (e.g., water produced in the cathode chamber of an electrolysis cell). Preferably, the ORP water solution administered in accordance with the present invention contains cathode water, e.g., in an amount of from about 10% by volume to about 90% by volume of the solution. More preferably, cathode water is present in the ORP water solution in an amount of from about 10% by volume to about 50% by volume, and still more preferably of from about 20% by volume to about 40% by volume of the solution, e.g., from about 20% by volume to about 30% by volume of the solution. Additionally, anode water can be present in the ORP water solution, e.g., in an amount of from about 50% by volume to about 90% by volume of the solution. Exemplary ORP water solutions can contain from about 10% by volume to about 50% by volume of cathode water and from about 50% by volume to about 90% by volume of anode water. The anode and cathode water can be produced using the three-chambered electrolysis cell shown in FIG. 3.

The ORP water solution containing both anode water and cathode water can be acidic, neutral or basic, and preferably has a pH of from about 1 to about 14, more preferably from about 3 to about 8, still more preferably from about 6.4 to about 7.8, and most preferably from about 7.4 to about 7.6.

In a preferred embodiment, the ORP water solution is administered to a diabetic patient with an infected foot ulcer in amount effective to treat the infected foot ulcer. Such patients to which the ORP water solution can be administered may be diagnosed with either Type I or Type II diabetes mellitus. Diabetic patients suitable for treatment can have an ankle-arm index (as measured by Doppler) of greater than or equal to 0.8, a transcutaneous oxygen press (TcPO2) value of greater than or equal to 30 mm Hg, and adequate circulation to the foot as evidenced by a palpable pulse on the foot (either dorsalis pedis or posterior tibial artery). Further, patients with lower ankle-arm indices can also be treated so as to, for example without limitation, prevent amputation. If amputation is necessary, the ORP water solution can also be use to treat the amputation stump.

Foot ulcers that are suitable for treatment according to the invention are generally, but not exculsively, located at or below the medial or lateral malleolus (ankle bone protrusions) surface of the foot. Such ulcers may extend through the dermis and into subcutaneous tissue with possible exposure of muscle, tendon but without exposure of the bone and/or joint capsule. Granulation issue may optionally be present in the ulcer. The surface area of the ulcer to be treated can be greater than or equal to about 2.0 cm2.

Preferably, the method of the invention includes administering the ORP water solution in an amount effective to treat infected diabetic foot ulcers that are either Grade 2 or Grade 3 according to the PEDIS classification. Grade 2 (mild) infections involve skin and subcutaneous tissue only without involvement of deeper tissues or systemic signs. The patient also can exhibit one or more of the following: (1) local swelling or induration; (2) local warmth; (3) local tenderness or pain; (4) erythema 0.5-2 cm from ulcer margin; and (5) purulent discharge. Grade 3 (moderate) infections are characterized by erythema of more than 2 about cm and at least one of conditions exhibited by Grade 2 infections or infection involving structures deeper than skin and subcutaneous tissues such as abscess, sceptic arthritis, and fasciitis.

The ORP water solution may be administered to patients with skin ulcers at any location using any suitable manner, e.g., topically by washing, irrigating, soaking or dressing the ulcer. Preferably, the ulcer is both washed and soaked, washed and dressed, or soaked and dressed. Most preferably, the ulcer is washed, soaked and dressed. Ulcer irrigation can be performed in accordance with the invention. The delivery pressure of ulcer irrigation plays an important factor in promoting ulcer healing. A delivery pressure of from about 5 psi to about 10 psi can be used in accordance with the invention for removing debris and bacteria from an ulcer while minimizing the damage to the surrounding normal tissues.

Prior to the administration of the ORP water solution, the skin ulcer is preferably subject to debridement therapy to remove hyperkeratinized, necrotic, and otherwise unhealthy tissue down to healthy appearing tissue. In debriding the ulcer, the wound margins are excised to healthy bleeding tissue. The ulcer may be cleaned of debris after debridement.

In between the washing, dressing and soaking, the skin ulcer may be allowed to air dry for any suitable period of time. Preferably, the skin ulcer is allowed to air dry for about two minutes.

The skin ulcer may be washed by applying the ORP water solution directly to the surface of the ulcer, for example, by pouring the ORP water solution over the ulcer. The skin ulcer is soaked by submersing the ulcer either partially or completely in the ORP water solution. The ulcer may soak for any suitable period of time. Generally, the skin ulcer is soaked in the ORP water solution for at least one minute. Preferably, the skin ulcer is soaked for at least about two minutes and for as long as hours, preferably as long as about 60 minutes, preferably as long as about 15 minutes. The application can be done daily for the first week, or twice a week, only if the ulcer is heavily infected and until it improves. The ulcer may be dressed by applying a moist wound dressing saturated with the ORP water solution. In addition to the moist wound dressing, the ulcer may optionally be dressed with dry gauze and an adhesive covering.

In applying a wound dressing to the skin ulcer, the gauze is typically cut to the size of the ulcer. The gauze can be saturated with the ORP water solution and any excess solution is wrung out of the gauze. Preferably, the dressing is not supersaturated with the ORP water solution although a supersaturated dressing can be effective for practicing the method of the invention. A sufficient amount of soaked gauze is preferably applied to fill, but not pack the wound. Dry gauze and tape can then be applied to the soaked gauze to hold it in place over the foot ulcer.

In one embodiment of the invention, the skin ulcer of a patient is first washed with the ORP water solution. The amount of ORP water solution used to wash the ulcer is preferably sufficient to remove debris. Next, the skin ulcer is soaked in the ORP water solution for a suitable period of time, preferably at least about two minutes. The patient's foot ulcer is then, optionally, air dried for a suitable period of time, preferably at least about two minutes. After drying, the foot ulcer can be dressed with a moist wound dressing that has been saturated with the ORP water solution. Dry gauze and an adhesive covering may be optionally applied on top of the moist wound dressing.

The process of washing, soaking and dressing the skin ulcer may be repeated at suitable intervals. Preferably, the procedure in which the ulcer is washed, soaked and dressed is repeated about once per month, about once per week, about once daily, or several times per day. The treatment of the ulcer using the ORP water solution may continue until the ulcer is sufficiently healed which may require repeating the procedure at least one time. The healing of the skin ulcer can be measured by a reduction of bacterial counts obtained from wound biopsy cultures or the rate of wound closure.

In another embodiment, the method of the invention involves three treatments of washing, soaking and dressing a skin ulcer over a three week period of time. Preferably, daily dressing changes are carried out during the course of the treatment in which new gauze dressing moistened with the ORP water solution is applied to the foot ulcer. The dressing on the ulcer may be changed more than once a day, for example, twice or three times per day, if the dressings become soiled. Preferably, debridement of the wound is preformed before each weekly procedure to remove necrotic or hyperkeratinized tissue.

The present invention also provides a method of reducing the microbial load in of a skin ulcer in a patient comprising administering an oxidative reductive potential water solution to the patient in an amount effective to reduce the microbial load in the skin ulcer. Preferably, the solution has a pH of from about 6.4 to about 7.8 and is stable for at least about one week, or the solution has a pH of from about 6.4 to about 7.8 and comprises anode water and cathode water. The microbial load can be determined by the number of positive pre-therapy and post-therapy cultures of the foot ulcer and the number of bacterial strains isolated from pre-therapy and post-therapy cultures from the foot ulcer. The microbial load can result from one or more organisms including, e.g., viruses, bacteria, and fungi.

Administering the ORP water in accordance with the invention can accelerate the healing of skin ulcers relative to conventional therapy. Accelerating healing in accordance with the invention can provide, without limitation, more rapid wound closure, faster in-growth of granulation tissue, prevention of systemic complications, reduction of antibiotic use, and shorter hospital stays. Accelerating healing in accordance with the invention can reduce healing times by about five days or more, e.g., about 7 days sooner, e.g., about 10 days sooner, in ORP water solution-treated patients relative to povidone iodine-treated patients.

The invention still further provides a method of decreasing likelihood of side effects resulting from administering an oxidative reductive potential water solution to the patient in an amount effective to treat the ulcer(s).

The invention additionally provides a method of decreasing the recurrence rate (e.g., recurrence post-treatment) of a skin ulcer in a patient which method includes administering an oxidative reductive potential water solution to the patient in an amount effective to decrease the likelihood of recurrence of the skin ulcer. Preferably, the solution has a pH of from about 6.4 to about 7.8 and is stable for at least about one week, or, has a pH of from about 6.4 to about 7.8 and comprises anode water and cathode water.

The invention further provides a method of decreasing the likelihood of dehiscence of a skin ulcer (e.g., post-treatment) in a patient comprising administering an oxidative reductive potential water solution to the patient in an amount effective to decrease the likelihood of dehiscence of the foot ulcer. Preferably, the solution has a pH of from about 6.4 to about 7.8 and is stable for at least about one week, or, has a pH of from about 6.4 to about 7.8 and comprises anode water and cathode water. Decreasing the likelihood of dehiscence in accordance with the invention can include decreasing the likelihood, e.g., by at least about 10%, preferably by at least about 20%, more preferably by at least about 30%, e.g., as measured by the reduction in the incidence of dehiscence in ORP water solution-treated patients relative to povidone iodine-treated patients.

The invention still further provides a method of decreasing likelihood of amputation resulting from a skin ulcer in a patient comprising administering an oxidative reductive potential water solution to the patient in an amount effective to decrease the likelihood of amputation. Preferably, the solution has a pH of from about 6.4 to about 7.8 and is stable for at least one week, or, wherein the solution has a pH of from about 6.4 to about 7.8 and comprises anode water and cathode water. Decreasing the likelihood of amputation in accordance with the invention can decrease the likelihood of amputation, e.g., by at least about 10%, preferably by at least about 15%, more preferably by at least about 20%, e.g., as measured by the reduction in the number of amputations in ORP water solution-treated patients relative to povidone iodine-treated patients.

The ORP water solution further may be applied to disinfect and sterilize, for example, to disinfect and sterilize medical or dental equipment by contacting the equipment with the ORP water solution for a sufficient period of time to reduce the level of organisms present on the equipment to a desired level. For disinfection and sterilization of hard surfaces, the ORP water solution may be applied to the hard surface directly from a container in which the ORP water solution is stored. For example, the ORP water solution may be poured, sprayed or otherwise directly applied to the hard surface. The ORP water solution may then be distributed over the hard surface using a suitable substrate such as, for example, cloth, fabric or paper towel. In hospital applications, the substrate is preferably sterile. Alternatively, the ORP water solution may first be applied to a substrate such as cloth, fabric or paper towel. The wetted substrate is then contacted with the hard surface. Alternatively, the ORP water solution may be applied to hard surfaces by dispersing the solution into the air as described herein. Alternatively, the ORP water solution can be applied as a gel to keep moistened and protected the skin ulcer. The ORP water solution may be applied in a similar manner to humans and animals.

An implement may optionally be used to apply the ORP water solution to hard surfaces such as floors, walls, and ceilings. For example, the ORP water solution may be dispensed onto a mop head for application to floors. Other suitable implements for applying the ORP water solution to hard surfaces are described in U.S. Pat. No. 6,663,306.

The invention further provides a cleaning wipe comprising a water insoluble substrate and the ORP water solution as described herein, wherein the ORP water solution is dispensed onto the substrate. The ORP water solution may be impregnated, coated, covered or otherwise applied to the substrate. Preferably, the substrate is pretreated with the ORP water solution before distribution.

Suitable substrate can include, e.g., cleaning wipes made of any suitable water-insoluble absorbent or adsorbent material. A wide variety of materials can be used as the substrate. It should have sufficient wet strength, abrasivity, loft and porosity, and should not so adversely impact the stability of the ORP water solution as to preclude the intended use. Examples include non woven substrates, woven substrates, hydroentangled substrates and sponges.

The substrate may have one or more layers. Each layer may have the same or different textures and abrasiveness. Differing textures can result from the use of different combinations of materials or from the use of different manufacturing processes or a combination thereof. The substrate can thus provide a vehicle for delivering the ORP water solution to the surface to be treated.

The substrate may be a single nonwoven sheet or multiple nonwoven sheets. The nonwoven sheet may be made of wood pulp, synthetic fibers, natural fibers, and blends thereof. Suitable synthetic fibers for use in the substrate include, without limitation, polyester, rayon, nylon, polypropylene, polyethylene, other cellulose polymers, and mixtures of such fibers. The nonwovens may include nonwoven fibrous sheet materials which include meltblown, coform, air-laid, spun bond, wet laid, bonded-carded web materials, hydroentangled (also known as spunlaced) materials, and combinations thereof. These materials can comprise synthetic or natural fibers or combinations thereof. A binder may optionally be present in the substrate.

Examples of suitable nonwoven, water insoluble substrates include 100% cellulose Wadding Grade 1804, 100% polypropylene needlepunch material NB 701-2.8-W/R, a blend of cellulosic and synthetic fibres-Hydraspun 8579, and 70% Viscose/30% PES Code 9881. Additional examples of nonwoven substrates suitable for use in the cleaning wipes are described in U.S. Pat. Nos. 4,781,974, 4,615,937, 4,666,621, and 5,908,707, and International Patent Application Publications WO 98/03713, WO 97/40814, and WO 96/14835.

The substrate may also be made of woven materials, such as cotton fibers, cotton/nylon blends, or other textiles. Regenerated cellulose, polyurethane foams, and the like, which are used in making sponges, may also be suitable for use.

The liquid loading capacity of the substrate should be at least about 50%-1000% of the dry weight thereof, and preferably at least from about 200%-about 800%. This is expressed as loading about ½ to 10 times the weight of the substrate. The weight of the substrate can vary without limitation from about 0.01 to about 1,000 grams per square meter, most preferably from about 25 to about 120 grams/m2 (referred to as "basis weight") and can exist as a sheet or web which is cut, die-cut, or otherwise can be sized into the appropriate shape and size. The cleaning wipes will preferably have a certain wet tensile strength which is preferably from about 25 to about 250 Newtons/m, more preferably about 75-170 Newtons/m.

The ORP water solution may be dispensed, impregnated, coated, covered or otherwise applied to the substrate by any suitable method. For example, individual portions of substrate may be treated with a discrete amount of the ORP water solution. Preferably, a mass treatment of a continuous web of substrate material with the ORP water solution is carried out. The entire web of substrate material may be soaked in the ORP water solution. Alternatively, as the substrate web is spooled, or even during creation of a nonwoven substrate, the ORP water solution can be sprayed or metered onto the web. A stack of individually cut and sized portions of substrate may be impregnated or coated with the ORP water solution in its container by the manufacturer.

Cleaning wipes may optionally contain additional components to improve the properties of the wipes. For example, cleaning wipes may further comprise polymers, surfactants, polysaccharides, polycarboxylates, polyvinyl alcohols, solvents, chelating agents, buffers, thickeners, dyes, colorants, fragrances, and mixtures thereof to improve the properties of the wipes. These optional components should not impact the stability of the ORP water solution so adversely as to preclude the intended end use. Examples of various components that may optionally be included in cleaning wipes are described in U.S. Pat. Nos. 6,340,663, 6,649,584 and 6,624,135. Suitable cleaning wipes are further described in U.S. Patent Application Publication No. 2005/0139808.

The ORP water solution of the invention may alternatively be dispersed into the environment through a gaseous medium, such as air. The ORP water solution may be dispersed into the air by any suitable means. For example, the ORP water solution may be formed into droplets of any suitable size and dispersed into a room. Suitable methods of dispersing the ORP water solution into the environment are described in U.S. Patent Application Publication No. 2005/139808.

The ORP water solution may optionally contain a bleaching agent and a suitable household additive, e.g., as described in U.S. Patent Application Publication No 2005/0139808.

The ORP water solution administered in accordance with the invention is preferably produced using at least one electrolysis cell comprising an anode chamber, a cathode chamber and a salt solution chamber located between the anode and cathode chambers, wherein at least some of the anode and cathode water are combined such that the ORP water solution comprises anode water and cathode water. A diagram of an exemplary three chamber electrolysis cell that can be used in preparing an exemplary ORP water solution is shown in FIG. 1.

The electrolysis cell 100 has an anode chamber 102, cathode chamber 104 and salt solution chamber 106. The salt solution chamber is located between the anode chamber 102 and cathode chamber 104. The anode chamber 102 has an inlet 108 and outlet 110 to permit the flow of water through the anode chamber 102. The cathode chamber 104 similarly has an inlet 112 and outlet 114 to permit the flow of water through the cathode chamber 104. The salt solution chamber 106 has an inlet 116 and outlet 118. The electrolysis cell 100 preferably includes a housing to hold all of the components together.

The anode chamber 102 is separated from the salt solution chamber by an anode electrode 120 and an anion ion exchange membrane 122. The anode electrode 120 may be positioned adjacent to the anode chamber 102 with the membrane 122 located between the anode electrode 120 and the salt solution chamber 106. Alternatively, the membrane 122 may be positioned adjacent to the anode chamber 102 with the anode electrode 120 located between the membrane 122 and the salt solution chamber 106.

The cathode chamber 104 is separated from the salt solution chamber by a cathode electrode 124 and a cathode ion exchange membrane 126. The cathode electrode 124 may be positioned adjacent to the cathode chamber 104 with the membrane 126 located between the cathode electrode 124 and the salt solution chamber 106. Alternatively, the membrane 126 may be positioned adjacent to the cathode chamber 104 with the cathode electrode 124 located between the membrane 126 and the salt solution chamber 106.

The electrodes are preferably constructed of metal to permit a voltage potential to be applied between the anode chamber and cathode chamber. The metal electrodes are preferably planar and have similar dimensions and cross-sectional surface area to that of the ion exchange membranes. The electrodes are preferably configured to expose a substantial portion of the surface of the ion exchange members to the water in their respective anode chamber and cathode chamber. This permits the migration of ionic species between the salt solution chamber, anode chamber and cathode chamber. Preferably, the electrodes have a plurality of passages or apertures evenly spaced across the surface of the electrodes.

A source of electrical potential is connected to the anode electrode 120 and cathode electrode 124 so as to induce an oxidation reaction in the anode chamber 102 and a reduction reaction in the cathode chamber 104.

The ion exchange membranes 122 and 126 used in the electrolysis cell 100 may be constructed of any suitable material to permit the exchange of ions between the salt solution chamber 106 and the anode chamber 102 such as, e.g., chloride ions (Cl−) and between the salt solution salt solution chamber 106 and the cathode chamber 104 such as, e.g., sodium ions (Na+). The anode ion exchange membrane 122 and cathode ion exchange membrane 126 may be made of the same or different material of construction. Preferably, the anode ion exchange membrane comprises a fluorinated polymer. Suitable fluorinated polymers include, for example, perfluorosulfonic acid polymers and copolymers such as perfluorosulfonic acid/PTFE copolymers and perfluorosulfonic acid/TFE copolymers. The ion exchange membrane may be constructed of a single layer of material or multiple layers. Suitable ion exchange membrane polymers can include one or more ion exchange membrane polymers marketed under the trademark Nafion®.

The source of the water for the anode chamber 102 and cathode chamber 104 of the electrolysis cell 100 may be any suitable water supply. The water may be from a municipal water supply or alternatively pretreated prior to use in the electrolysis cell. Preferably, the water is pretreated and is selected from the group consisting of softened water, purified water, distilled water, and deionized water. More preferably, the pretreated water source is ultrapure water obtained using reverse osmosis and UV light purification equipment.

The salt water solution for use in the salt solution chamber 106 may be any aqueous salt solution that contains suitable ionic species to produce the ORP water solution. Preferably, the salt water solution is an aqueous sodium chloride (NaCl) salt solution, also commonly referred to as a saline solution. Other suitable salt solutions include other chloride salts such as potassium chloride, ammonium chloride and magnesium chloride as well as other halogen salts such as potassium and bromine salts. The salt solution may contain a mixture of salts.

Figure 2:
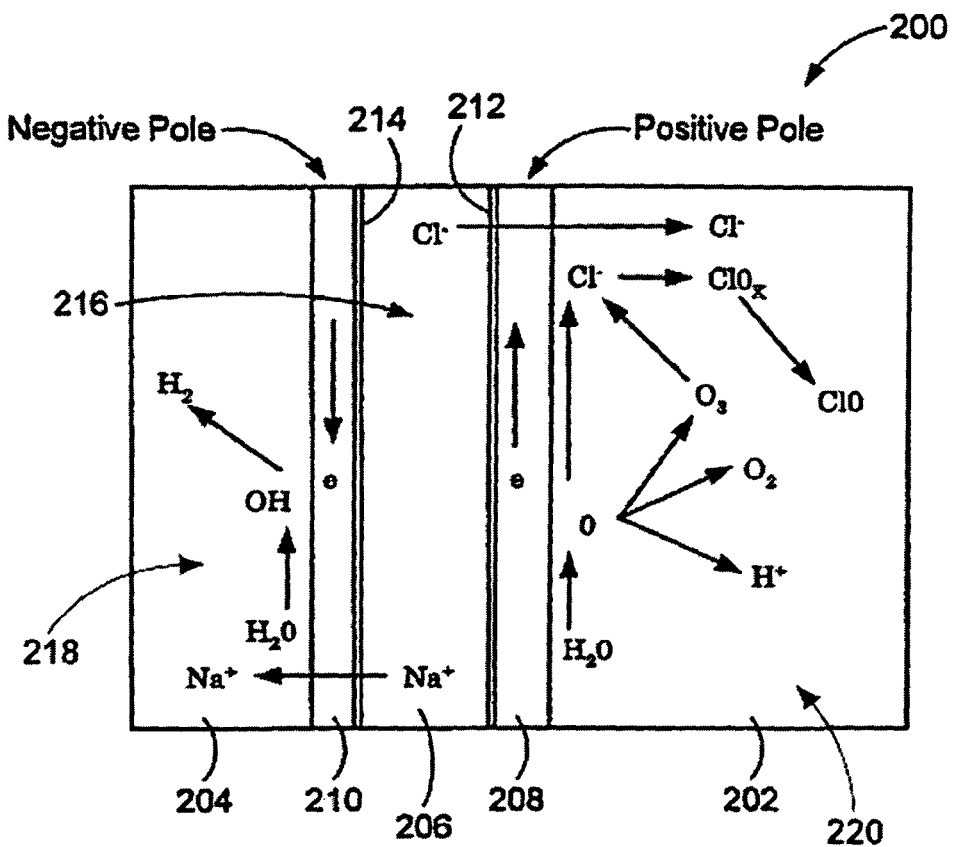
FIG. 2 illustrates a three-chambered electrolysis cell and depicts ionic species generated in an exemplary production process for producing an oxidative reductive potential water solution for use in accordance with the invention.

FIG. 2 illustrates what are believed to be various ionic species produced in the three chambered electrolysis cell useful in connection with the invention. The three chambered electrolysis cell 200 includes an anode chamber 202, cathode chamber 204, and a salt solution chamber 206. Upon application of a suitable electrical current to the anode 208 and cathode 210, the ions present in the salt solution flowing through the salt solution chamber 206 migrate through the anode ion exchange membrane 212 and cathode ion exchange membrane 214 into the water flowing through the anode chamber 202 and cathode chamber 204, respectively.

FIG. 2 illustrates what are believed to be the various ionic species produced in the three chambered electrolysis cell useful in the invention. The three chambered electrolysis cell 200 includes an anode chamber 202, cathode chamber 204, and a salt solution chamber 206. Upon application of a suitable electrical current to the anode 208 and cathode 210, the ions present in the salt solution flowing through the salt solution chamber 206 migrate through the anode ion exchange membrane 212 and cathode ion exchange membrane 214 into the water flowing through the anode chamber 202 and cathode chamber 204, respectively.

Positive ions migrate from the salt solution 216 flowing through the salt solution chamber 206 to the cathode water 218 flowing through the cathode chamber 204. Negative ions migrate from the salt solution 216 flowing through the salt solution chamber 206 to the anode water 220 flowing through the anode chamber 202.

Preferably, the salt solution 216 is aqueous sodium chloride (NaCl) that contains both sodium ions (Na+) and chloride ions (Cl−) ions. Positive Na+ ions migrate from the salt solution 216 to the cathode water 218. Negative Cl− ions migrate from the salt solution 216 to the anode water 220.

The sodium ions and chloride ions may undergo further reaction in the anode chamber 202 and cathode chamber 204. For example, chloride ions can react with various oxygen-containing ions and other species (e.g., oxygen free radicals, O2, O3) present in the anode water 220 to produce ClOn− and ClO−. Other reactions may also take place in the anode chamber 202 including the formation of oxygen free radicals, hydrogen ions (H+), oxygen (as O2), and, optionally, ozone (O3) and peroxides (e.g., hydrogen peroxide). In the cathode chamber 204, hydrogen gas (H2), hydroxide ions (OH−), sodium hydroxide (NaOH), and other radicals may be formed.

Figure 3:
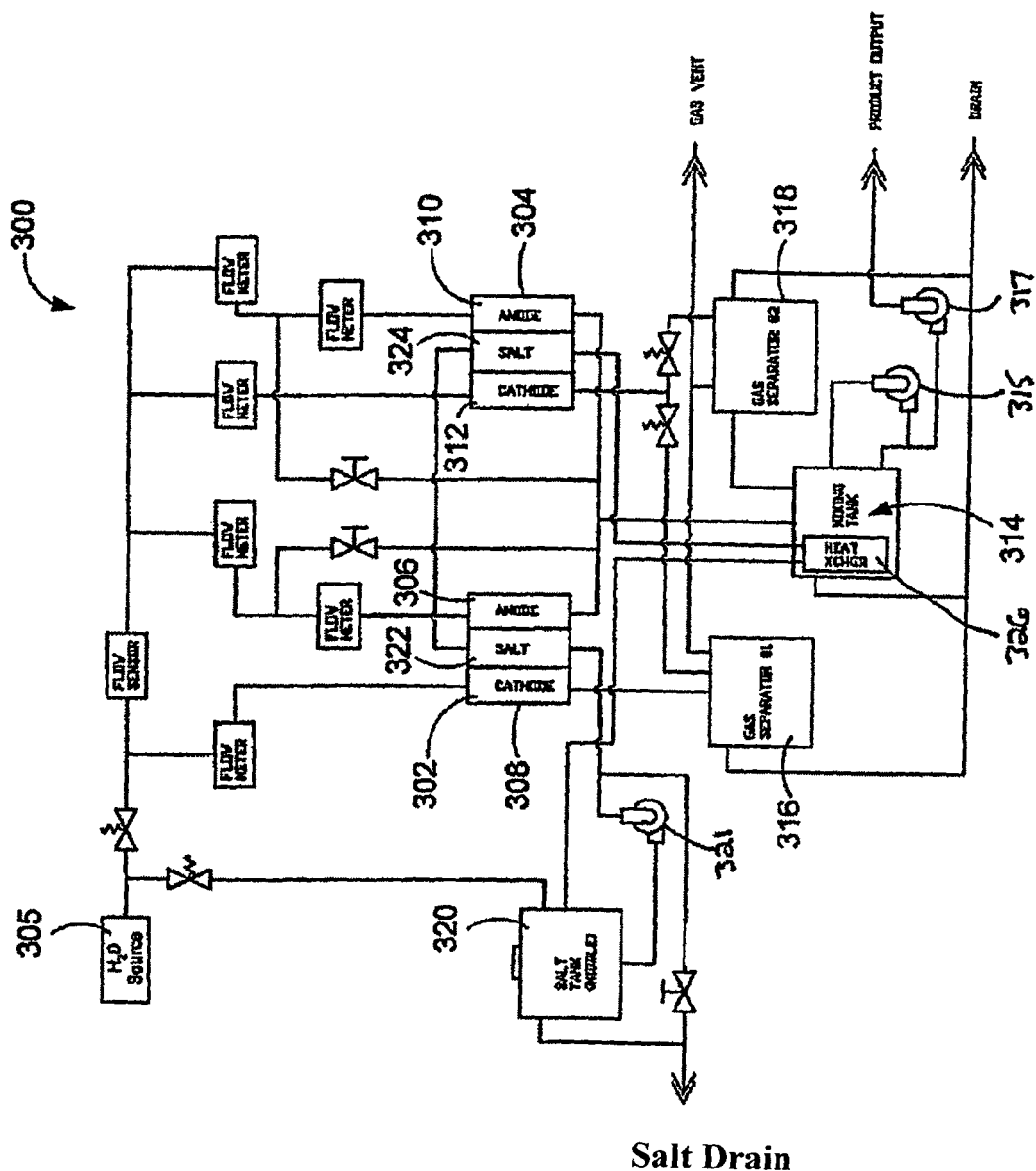
FIG. 3 is a schematic flow diagram of a process for producing an exemplary oxidative reductive potential water administered in accordance with the present invention.

The process and apparatus for producing the ORP water solution also can utilize at least two three chambered electrolysis cells. A diagram of a process for producing an ORP water solution using two electrolysis cells of the invention is shown in FIG. 3.

The process 300 includes two three-chambered electrolytic cells, specifically a first electrolytic cell 302 and second electrolytic cell 304. Water is transferred, pumped or otherwise dispensed from the water source 305 to anode chamber 306 and cathode chamber 308 of the first electrolytic cell 302 and to anode chamber 310 and cathode chamber 312 of the second electrolytic cell 304. Typically, the process of the invention can produce from about 1 liter/minute to about 50 liters/minute of ORP water solution. The production capacity may be increased by using additional electrolytic cells. For example, three, four, five, six, seven, eight, nine, ten or more three-chambered electrolytic cells may be used to in increase the output of the ORP water solution of the invention.

The anode water produced in the anode chamber 306 and anode chamber 310 are collected in the mixing tank 314. A portion of the cathode water produced in the cathode chamber 308 and cathode chamber 312 is collected in mixing tank 314 and combined with the anode water. The remaining portion of cathode water produced in the process is discarded. The cathode water may optionally be subjected to gas separator 316 and/or gas separator 318 prior to addition to the mixing tank 314. The gas separators remove gases such as hydrogen gas that are formed in cathode water during the production process.

The mixing tank 314 may optionally be connected to a recirculation pump 315 to permit homogenous mixing of the anode water and portion of cathode water from electrolysis cells 302 and 304. Further, the mixing tank 314 may optionally include suitable devices for monitoring the level and pH of the ORP water solution. The ORP water solution may be transferred from the mixing tank 314 via pump 317 for application in disinfection or sterilization at or near the location of the mixing tank. Alternatively, the ORP water solution may be dispensed into suitable containers for shipment to a remote site (e.g., warehouse, hospital, etc.).

The process 300 further includes a salt solution recirculation system to provide the salt solution to salt solution chamber 322 of the first electrolytic cell 302 and the salt solution chamber 324 of the second electrolytic cell 304. The salt solution is prepared in the salt tank 320. The salt solution is transferred via pump 321 to the salt solution chambers 322 and 324. Preferably, the salt solution flows in series through salt solution chamber 322 first followed by salt solution chamber 324. Alternatively, the salt solution may be pumped to both salt solution chambers simultaneously.

Before returning to the salt tank 320, the salt solution may flow through a heat exchanger 326 in the mixing tank 314 to control the temperature of the ORP water solution as needed.

The ions present in the salt solution are depleted over time in the first electrolytic cell 302 and second electrolytic cell 304. An additional source of ions may periodically be added to the mixing tank 320 to replace the ions that are transferred to the anode water and cathode water. The additional source of ions may be used to maintain a constant pH of the salt solution which tends to drop (i.e., become acidic) over time. The source of additional ions may be any suitable compound including, for example, salts such as sodium chloride. Preferably, sodium hydroxide is added to the mixing tank 320 to replace the sodium ions (Na+) that are transferred to the anode water and cathode water.

When the process utilizes at least two three-chambered electrolytic cells, each of the electrolytic cells preferably includes an anode chamber, cathode chamber, and salt solution chamber separating the anode and cathode chambers. The apparatus preferably includes a mixing tank for collecting the anode water produced by the electrolytic cells and a portion of the cathode water produced by one or more of the electrolytic cells. Preferably, the apparatus further includes a salt recirculation system to permit recycling of the salt solution supplied to the salt solution chambers of the electrolytic cells.

The following examples further illustrate the invention but, of course, should not be construed as in any way limiting in its scope.

Examples 1-3

These examples demonstrate the unique features of the ORP water solution of the invention. The samples of the ORP water solution in Examples 1-3 were analyzed in accordance with the methods described herein to determine the physical properties and levels of ionic and other chemical species present in each sample. The results obtained for chlorine dioxide, ozone and hydrogen peroxide are based on standard tests used to measure such species; however, the results may be indicative of different species, which can also generate positive test results. Further, it has been reported that chlorine dioxide, ozone and hydrogen peroxide can react with hypochlorite resulting in their consumption and the production of other species (e.g., HCl and $O_2$). The pH, oxidative-reductive potential (ORP) and ionic species present are set forth in Table 1 for each sample of the ORP water solution.

TABLE 1

Physical characteristics and ion species present for the ORP water solution samples

|  | EXAMPLE 1 | EXAMPLE 2 | EXAMPLE 3 |
|---|---|---|---|
| pH | 7.45 | 7.44 | 7.45 |
| ORP (mV) | +879 | +881 | +874 |
| Total $Cl^-$ (ppm) | 110 | 110 | 120 |
| Bound $Cl^-$ (ppm) | 5 | 6 | 6 |

The ORP water solution has suitable physical characteristics for use in disinfection, sterilization and/or cleaning.

Examples 4-10

These examples demonstrate the addition of a bleaching agent to the ORP water solution according to the invention in various amounts. In particular, these examples demonstrate the antimicrobial activity and fabric bleaching ability of the compositions.

A 10% Clorox® bleach solution was prepared using distilled water. The following solutions were then prepared using the 10% bleach solution: 80% ORP water solution/20% bleach (Example 4); 60% ORP water solution/40% bleach (Example 5); 40% ORP water solution/60% bleach (Example 6); 20% ORP water solution/80% bleach (Example 7); and 0% ORP water solution/100% bleach (Example 8). Two control solutions were also used for comparison including 100% ORP water solution/0% bleach (Example 9) and an ORP water solution with 0.01% Tween 20 detergent (Example 10). The physical characteristics of these samples were determined, specifically pH, oxidative-reductive potential (ORP), total chlorine ($Cl^-$) content, hypochlorous acid ($HClO^-$) content, chlorine dioxide content and peroxide content, and are set forth in Table 2.

TABLE 2

Physical characteristics of ORP water solution/bleach compositions

|  | pH | ORP (mV) | Total $Cl^-$ (ppm) | $HClO^-$ (ppm) |
|---|---|---|---|---|
| Ex. 4 | 8.92 | +789 | 1248 | 62 |
| Ex. 5 | 9.20 | +782 | 2610 | 104 |
| Ex. 6 | 9.69 | +743 | 4006 | 80 |
| Ex. 7 | 9.86 | +730 | 4800 | 48 |
| Ex. 8 | 9.80 | +737 | 5000 | 50 |
| Ex. 9 | 7.06 | +901 | 64 | 32 |
| Ex. 10 | 6.86 | +914 | 51 | 26 |

The large bolus of chlorine ions added as part of the bleaching agent prevented the accurate measurement of the chlorine dioxide and peroxide levels as indicated with the n.d. designations. Also, the results obtained for chlorine dioxide and peroxide are based on standard tests used to measure such species; however, the results may be indicative of different species which can also generate positive test results. Further, it has been reported that chlorine dioxide, ozone and hydrogen peroxide can react with hypochlorite resulting their consumption and the production of other species (e.g., HCl and $O_2$). As these examples demonstrate, the hypochlorous acid levels of the ORP water solution with and without the addition of a bleaching agent are similar.

The samples of Examples 4-10 were subjected to a high spore count test using *Bacillus subtilis* var. *niger* spores (ATCC #9372 obtained from SPS Medical of Rush, N.Y.).

Spore suspensions were concentrated (by evaporation in a sterile hood) to $4 \times 10^6$ spores per 100 microliters. A 100 microliter sample of the spore suspension were mixed with 900 microliters of each of the samples in Examples 4-10. The samples were incubated at room temperature for periods of 1 to 5 minutes as set forth in Table 3. At the indicated times, 100 microliters of the incubated samples were plated onto individual TSA plates and incubated for 24 hours at 35° C.±2° C., after which the number of resulting colonies on each plate was determined. The control plates demonstrated that the starting spore concentrations were $>1 \times 10^6$ spores/100 microliters. The concentration of Bacillus spores for the various samples at the various incubation times (as the average of two determinations) is set forth in Table 3.

TABLE 3

Bacillus spore concentrations (spores/100 microliters)

|       | 1 minute | 2 minutes | 3 minutes | 4 minutes | 5 minutes |
|-------|----------|-----------|-----------|-----------|-----------|
| Ex. 4 | >>1000   | 411       | 1         | 0         | 2         |
| Ex. 5 | >>1000   | 1000      | 1         | 0         | 0         |
| Ex. 6 | >>1000   | >>1000    | >1000     | 22        | 0         |
| Ex. 7 | >>1000   | >>1000    | >1000     | 15        | 0         |
| Ex. 8 | >>1000   | >>1000    | >1000     | 3         | 1         |
| Ex. 9 | >>1000   | 74        | 0         | 0         | 0         |
| Ex 10 | >>1000   | 239       | 3         | 0         | 0         |

As these results demonstrate, as the concentration of bleach (as 10% aqueous bleach solution) increases, the amount of Bacillus spores killed is reduced for the samples incubated for 2-3 minutes. However, for samples incubated for 5 minutes, the bleach concentration does not impact Bacillus spore kill. Further, the results demonstrate that the addition of 0.01% detergent to the ORP water solution does not reduce spore kill.

The samples of Examples 4-10 were subjected to a fabric bleaching test. The fabric upon which the samples were tested was a 100% rayon children's t-shirt with dark blue dye patches. Two inch square pieces of dyed fabric were placed into 50 mL plastic tubes. Each fabric piece was covered by a sample of the solution in Examples 4-10. The elapsed time until complete bleaching was obtained, as determined by the whitening of the fabric, is set forth in Table 4.

TABLE 4

Time until complete bleaching of fabric sample

| Example | Time       |
|---------|------------|
| Ex. 4   | 39 minutes |
| Ex. 5   | 23 minutes |
| Ex. 6   | 18 minutes |
| Ex. 7   | 19 minutes |
| Ex. 8   | 10 minutes |
| Ex. 9   | >6 hours   |
| Ex. 10  | >6 hours   |

As demonstrated by these examples, as the concentration of the ORP water solution increases in the composition, the time until complete bleaching is achieved increases.

Example 11

This example demonstrates the use of an exemplary ORP water solution, Microcyn as an effective antimicrobial solution.

An In-Vitro Time-Kill evaluation was performed using Microcyn oxidative reductive potential water. Microcyn was evaluated versus challenge suspensions of fifty different microorganism strains—twenty-five American Type Culture Collection (ATCC) strains and twenty-five Clinical Isolates of those same species—as described in the Tentative Final Monograph, Federal Register, 17 Jun. 1994, vol. 59:116, pg. 31444. The percent reductions and the Log 10 reductions from the initial population of each challenge strain were determined following exposures to Microcyn for thirty (30) seconds, one (1) minute, three (3) minutes, five (5) minutes, seven (7) minutes, nine (9) minutes, eleven (11) minutes, thirteen (13) minutes, fifteen (15) minutes, and twenty (20) minutes. All agar-plating was performed in duplicate and Microcyn was evaluated at a 99% (v/v) concentration. All testing was performed in accordance with Good Laboratory Practices, as specified in 21 C.F.R. Part 58.

The following table summarizes the results of the above-mentioned In-Vitro Time-Kill evaluation at the thirty second exposure mark for all populations tested which were reduced by more than 5.0 $Log_{10}$:

TABLE 5

In-Vitro 30-second Kill.

| No. | Microorganism Species | Initial Population (CFU/mL) | Post-Exposure Population (CFU/mL) | $Log_{10}$ Reduction | Percent Reduction |
|-----|----------------------|------------------------------|-----------------------------------|----------------------|-------------------|
| 1 | Acinetobacter baumannii (ATCC #19003) | $2.340 \times 10^9$ | $<1.00 \times 10^3$ | 6.3692 | 99.9999 |
| 2 | Acinetobacter baumannii Clinical Isolate BSLI #061901Ab3 | $1.8150 \times 10^9$ | $<1.00 \times 10^3$ | 6.2589 | 99.9999 |
| 3 | Bacteroides fragilis (ATCC #43858) | $4.40 \times 10^{10}$ | $<1.00 \times 10^3$ | 7.6435 | 99.9999 |
| 4 | Bacteroides fragilis Clinical Isolate BSLI #061901Bf6 | $2.70 \times 10^{10}$ | $<1.00 \times 10^3$ | 7.4314 | 99.9999 |
| 5 | Candida albicans (ATCC #10231) | $2.70 \times 10^{10}$ | $<1.00 \times 10^3$ | 6.3345 | 99.9999 |
| 6 | Candida albicans Clinical Isolate BSLI #042905Ca | $5.650 \times 10^9$ | $<1.00 \times 10^3$ | 6.7520 | 99.9999 |
| 7 | Enterobacter aerogenes (ATCC #29007) | $1.2250 \times 10^9$ | $<1.00 \times 10^3$ | 6.0881 | 99.9999 |

TABLE 5-continued

In-Vitro 30-second Kill.

| No. | Microorganism Species | Initial Population (CFU/mL) | Post-Exposure Population (CFU/mL) | $\text{Log}_{10}$ Reduction | Percent Reduction |
|---|---|---|---|---|---|
| 8 | Enterobacter aerogenes Clinical Isolate BSLI #042905Ea | $1.0150 \times 10^9$ | $<1.00 \times 10^3$ | 6.0065 | 99.9999 |
| 9 | Enterococcus faecalis (ATCC #29212) | $2.610 \times 10^9$ | $<1.00 \times 10^3$ | 6.4166 | 99.9999 |
| 10 | Enterococcus faecalis Clinical Isolate BSLI #061901Efs2 | $1.2850 \times 10^9$ | $<1.00 \times 10^3$ | 6.1089 | 99.9999 |
| 11 | Enterococcus faecium VRE, MDR (ATCC #51559) | $3.250 \times 10^9$ | $<1.00 \times 10^3$ | 6.5119 | 99.9999 |
| 12 | Enterococcus faecium Clinical Isolate BSLI #061901Efm1 | $1.130 \times 10^9$ | $<1.00 \times 10^3$ | 6.0531 | 99.9999 |
| 13 | Escherichia coli (ATCC #11229) | $5.00 \times 10^8$ | $<1.00 \times 10^3$ | 5.6990 | 99.9998 |
| 14 | Escherichia coli Clinical Isolate BSLI #042905Ec1 | $3.950 \times 10^8$ | $<1.00 \times 10^3$ | 5.5966 | 99.9997 |
| 15 | Escherichia coli (ATCC #25922) | $6.650 \times 10^8$ | $<1.00 \times 10^3$ | 5.8228 | 99.9998 |
| 16 | Escherichia coli Clinical Isolate BSLI #042905Ec2 | $7.40 \times 10^8$ | $<1.00 \times 10^3$ | 5.8692 | 99.9998 |
| 17 | Haemophilus influenzae (ATCC #8149) | $1.5050 \times 10^9$ | $<1.00 \times 10^4$ | 5.1775 | 99.9993 |
| 18 | Haemophilus influenzae Clinical Isolate BSLI #072605Hi | $1.90 \times 10^9$ | $<1.00 \times 10^4$ | 5.2788 | 99.9995 |
| 19 | Klebsiella oxytoca MDR (ATCC #15764) | $1.120 \times 10^9$ | $<1.00 \times 10^3$ | 6.0492 | 99.9999 |
| 20 | Klebsiella oxytoca Clinical Isolate BSLI #061901Ko1 | $1.810 \times 10^9$ | $<1.00 \times 10^3$ | 6.2577 | 99.9999 |
| 21 | Klebsiella pneumoniae subsp. ozaenae (ATCC #29019) | $1.390 \times 10^9$ | $<1.00 \times 10^3$ | 6.1430 | 99.9999 |
| 22 | Klebsiella pneumoniae Clinical Isolate BSLI #061901Kpn2 | $9.950 \times 10^8$ | $<1.00 \times 10^3$ | 5.9978 | 99.9999 |
| 23 | Micrococcus luteus (ATCC #7468) | $6.950 \times 10^8$ | $<1.00 \times 10^3$ | 5.8420 | 99.9999 |
| 24 | Micrococcus luteus Clinical Isolate BSLI #061901Ml2 | $1.5150 \times 10^9$ | $<1.00 \times 10^3$ | 6.1804 | 99.9999 |
| 25 | Proteus mirabilis (ATCC #7002) | $1.5950 \times 10^9$ | $<1.00 \times 10^3$ | 6.2028 | 99.9999 |
| 26 | Proteus mirabilis Clinical Isolate BSLI #061901Pm2 | $2.0950 \times 10^9$ | $<1.00 \times 10^3$ | 6.3212 | 99.9999 |
| 27 | Pseudomonas aeruginosa (ATCC #15442) | $6.450 \times 10^8$ | $<1.00 \times 10^3$ | 5.8096 | 99.9999 |
| 28 | Pseudomonas aeruginosa Clinical Isolate BSLI #072605Pa | $1.3850 \times 10^9$ | $<1.00 \times 10^3$ | 6.1414 | 99.9999 |
| 29 | Pseudomonas aeruginosa (ATCC #27853) | $5.550 \times 10^8$ | $<1.00 \times 10^3$ | 5.7443 | 99.9999 |
| 30 | Pseudomonas aeruginosa Clinical Isolate BSLI #061901Pa2 | $1.1650 \times 10^9$ | $<1.00 \times 10^3$ | 6.0663 | 99.9999 |
| 31 | Serratia marcescens (ATCC #14756) | $9.950 \times 10^8$ | $<1.00 \times 10^3$ | 5.9978 | 99.9999 |
| 32 | Serratia marcescens Clinical Isolate BSLI #042905Sm | $3.6650 \times 10^9$ | $<1.00 \times 10^3$ | 6.5641 | 99.9999 |
| 33 | Staphylococcus aureus (ATCC #6538) | $1.5050 \times 10^9$ | $<1.00 \times 10^3$ | 6.1775 | 99.9999 |
| 34 | Staphylococcus aureus Clinical Isolate BSLI #061901Sa1 | $1.250 \times 10^9$ | $<1.00 \times 10^3$ | 6.0969 | 99.9999 |
| 35 | Staphylococcus aureus (ATCC #29213) | $1.740 \times 10^9$ | $<1.00 \times 10^3$ | 6.2405 | 99.9999 |

TABLE 5-continued

In-Vitro 30-second Kill.

| No. | Microorganism Species | Initial Population (CFU/mL) | Post-Exposure Population (CFU/mL) | $\text{Log}_{10}$ Reduction | Percent Reduction |
|---|---|---|---|---|---|
| 36 | *Staphylococcus aureus* Clinical Isolate BSLI #061901Sa2 | $1.1050 \times 10^9$ | $<1.00 \times 10^3$ | 6.0434 | 99.9999 |
| 37 | *Staphylococcus epidermidis* (ATCC #12228) | $1.0550 \times 10^9$ | $<1.00 \times 10^3$ | 6.0233 | 99.9999 |
| 38 | *Staphylococcus epidermidis* Clinical Isolate BSLI #072605Se | $4.350 \times 10^8$ | $<1.00 \times 10^3$ | 5.6385 | 99.9998 |
| 39 | *Staphylococcus haemolyticus* (ATCC #29970) | $8.150 \times 10^8$ | $<1.00 \times 10^3$ | 5.9112 | 99.9999 |
| 40 | *Staphylococcus haemolyticus* Clinical Isolate BSLI #042905Sha | $8.350 \times 10^8$ | $<1.00 \times 10^3$ | 5.9217 | 99.9999 |
| 41 | *Staphylococcus hominis* (ATCC #27844) | $2.790 \times 10^8$ | $<1.00 \times 10^3$ | 5.4456 | 99.9996 |
| 42 | *Staphylococcus hominis* Clinical Isolate BSLI #042905Sho | $5.20 \times 10^8$ | $<1.00 \times 10^3$ | 5.7160 | 99.9998 |
| 43 | *Staphylococcus saprophyticus* (ATCC #35552) | $9.10 \times 10^8$ | $<1.00 \times 10^3$ | 5.9590 | 99.9999 |
| 44 | *Staphylococcus saprophyticus* Clinical Isolate BSLI #042905Ss | $1.4150 \times 10^9$ | $<1.00 \times 10^3$ | 6.1508 | 99.9999 |
| 45 | *Streptococcus pneumoniae* (ATCC #33400) | $2.1450 \times 10^9$ | $<1.00 \times 10^4$ | 5.3314 | 99.9995 |
| 46 | *Streptococcus pyogenes* (ATCC #19615) | $5.20 \times 10^9$ | $<1.00 \times 10^3$ | 6.7160 | 99.9999 |
| 47 | *Streptococcus pyogenes* Clinical Isolate BSLI #061901Spy7 | $2.5920 \times 10^9$ | $<1.00 \times 10^3$ | 6.4141 | 99.9999 |

While their microbial reductions were measured at less than 5.0 $\text{Log}_{10}$, Microcyn also demonstrated antimicrobial activity against the remaining three species not included in Table 5. More specifically, a thirty second exposure to Microcyn reduced the population of *Streptococcus pneumoniae* (Clinical Isolate; BSLI #072605Spn1) by more than 4.5 $\text{Log}_{10}$, which was the limit of detection versus this species. Further, when challenged with *Candida tropicalis* (ATCC #750), Microcyn demonstrated a microbial reduction in excess of 3.0 $\text{Log}_{10}$ following a thirty second exposure. Additionally, when challenged with *Candida tropicalis* (BSLI #042905Ct), Microcyn demonstrated a microbial reduction in excess of 3.0 $\text{Log}_{10}$ following a twenty minute exposure.

The exemplary results of this In-Vitro Time-Kill evaluation demonstrate that Microcyn oxidative reductive potential water exhibits rapid (i.e., less than 30 seconds in most cases) antimicrobial activity versus a broad spectrum of challenging microorganisms. Microbial populations of forty-seven out of the fifty Gram-positive, Gram-negative, and yeast species evaluated were reduced by more than 5.0 $\text{Log}_{10}$ within thirty seconds of exposure to the product.

Example 12

This example demonstrates a comparison of the antimicrobial activity of an exemplary ORP water solution, Microcyn, versus HIBICLENS® chlorhexidine gluconate solution 4.0% (w/v) and 0.9% sodium chloride irrigation (USP).

An In-Vitro Time-Kill evaluation was performed as described in Example 11 using HIBICLENS® chlorhexidine gluconate solution 4.0% (w/v) and a sterile 0.9% sodium chloride irrigation solution (USP) as reference products. Each reference product was evaluated versus suspensions of the ten American Type Culture Collection (ATCC) strains specifically denoted in the Tentative Final Monograph. The data collected was then analyzed against the Microcyn microbial reduction activity recorded in Example 11.

Microcyn oxidative reductive potential water reduced microbial populations of five of the challenge strains to a level comparable to that observed for the HIBICLENS® chlorhexidine gluconate solution. Both Microcyn and HIBICLENS® provided a microbial reduction of more than 5.0 $\text{Log}_{10}$ following a thirty second exposure to the following species: *Escherichia coli* (ATCC #11229 and ATCC #25922), *Pseudomonas aeruginosa* (ATCC #15442 and ATCC #27853), and *Serratia marcescens* (ATCC #14756). Further, as shown above in Table 5, Microcyn demonstrated excellent antimicrobial activity against *Micrococcus luteus* (ATCC #7468) by providing a 5.8420 $\text{Log}_{10}$ reduction after a thirty second exposure. However, a direct *Micrococcus luteus* (ATCC #7468) activity comparison to HIBICLENS® was not possible because after a thirty second exposure, HIBICLENS® reduced the population by the detection limit of the test (in this specific case, by more than 4.8 $\text{Log}_{10}$). It is noted that the sterile 0.9% sodium chloride irrigation solution reduced microbial populations of each of the six challenge strains discussed above by less than 0.3 $\text{Log}_{10}$ following a full twenty minute exposure.

Microcyn oxidative reductive potential water provided greater antimicrobial activity than both HIBICLENS® and the sodium chloride irrigation for four of the challenge strains tested: *Enterococcus faecalis* (ATCC #29212), *Staphylococcus aureus* (ATCC #6538 and ATCC #29213), and *Staphylococcus epidermidis* (ATCC #12228). The following table summarizes the microbial reduction results of the In-Vitro Time-Kill evaluation for these four species:

TABLE 6

Comparative kill results.

| Microorganism Species | Exposure Time | Log₁₀ Reduction Microcyn | HIBICLENS ® | NaCl Irrigation |
|---|---|---|---|---|
| Enterococcus faecalis (ATCC #29212) | 30 seconds | 6.4166 | 1.6004 | 0.3180 |
| | 1 minute | 6.4166 | 2.4648 | 0.2478 |
| | 3 minutes | 6.4166 | 5.2405 | 0.2376 |
| | 5 minutes | 6.4166 | 5.4166 | 0.2305 |
| | 7 minutes | 6.4166 | 5.4166 | 0.2736 |
| | 9 minutes | 6.4166 | 5.4166 | 0.2895 |
| | 11 minutes | 6.4166 | 5.4166 | 0.2221 |
| | 13 minutes | 6.4166 | 5.4166 | 0.2783 |
| | 15 minutes | 6.4166 | 5.4166 | 0.2098 |
| | 20 minutes | 6.4166 | 5.4166 | 0.2847 |
| Staphylococcus aureus (ATCC #6538) | 30 seconds | 6.1775 | 1.1130 | 0.0000 |
| | 1 minute | 6.1775 | 1.7650 | 0.0191 |
| | 3 minutes | 6.1775 | 4.3024 | 0.0000 |
| | 5 minutes | 6.1775 | 5.1775 | 0.0000 |
| | 7 minutes | 6.1775 | 5.1775 | 0.0000 |
| | 9 minutes | 6.1775 | 5.1775 | 0.0000 |
| | 11 minutes | 6.1775 | 5.1775 | 0.0267 |
| | 13 minutes | 6.1775 | 5.1775 | 0.0000 |
| | 15 minutes | 6.1775 | 5.1775 | 0.0191 |
| | 20 minutes | 6.1775 | 5.1775 | 0.0000 |
| Staphylococcus aureus (ATCC #29213) | 30 seconds | 6.2405 | 0.9309 | 0.0000 |
| | 1 minute | 6.2405 | 1.6173 | 0.0000 |
| | 3 minutes | 6.2405 | 3.8091 | 0.0460 |
| | 5 minutes | 6.2405 | 5.2405 | 0.0139 |
| | 7 minutes | 6.2405 | 5.2405 | 0.0000 |
| | 9 minutes | 6.2405 | 5.2405 | 0.0113 |
| | 11 minutes | 6.2405 | 5.2405 | 0.0283 |
| | 13 minutes | 6.2405 | 5.2405 | 0.0000 |
| | 15 minutes | 6.2405 | 5.2405 | 0.0000 |
| | 20 minutes | 6.2405 | 5.2405 | 0.0615 |
| Staphylococcus epidermidis (ATCC #12228) | 30 seconds | 5.6385 | 5.0233 | 0.0456 |
| | 1 minute | 5.6385 | 5.0233 | 0.0410 |
| | 3 minutes | 5.6385 | 5.0233 | 0.0715 |
| | 5 minutes | 5.6385 | 5.0233 | 0.0888 |
| | 7 minutes | 5.6385 | 5.0233 | 0.0063 |
| | 9 minutes | 5.6385 | 5.0233 | 0.0643 |
| | 11 minutes | 5.6385 | 5.0233 | 0.0211 |
| | 13 minutes | 5.6385 | 5.0233 | 0.1121 |
| | 15 minutes | 5.6385 | 5.0233 | 0.0321 |
| | 20 minutes | 5.6385 | 5.0233 | 0.1042 |

The results of this comparative In-Vitro Time-Kill evaluation demonstrate that Microcyn oxidative reductive potential water not only exhibits comparable antimicrobial activity to HIBICLENS® against *Escherichia coli* (ATCC #11229 and ATCC #25922), *Pseudomonas aeruginosa* (ATCC #15442 and ATCC #27853), *Serratia marcescens* (ATCC #14756), and *Micrococcus luteus* (ATCC #7468), but provides more effective treatment against *Enterococcus faecalis* (ATCC #29212), *Staphylococcus aureus* (ATCC #6538 and ATCC #29213), and *Staphylococcus epidermidis* (ATCC #12228). As shown in Table 6, Microcyn exemplifies a more rapid antimicrobial response (i.e., less than 30 seconds) in some species. Moreover, exposure to Microcyn results in a greater overall microbial reduction in all species listed in Table 6.

Example 13

This example illustrates stability, lack of toxicity, and antimicrobial activity of an exemplary ORP water solution, Microcyn, used in accordance with the invention.

Microcyn is a superoxidized solution of neutral pH with germicidal, sterilizing and wound antiseptic activity. Microcyn is prepared from pure water and salt (NaCl), has a small concentration of sodium (e.g., <55 ppm) and chlorine (e.g., <80 ppm), a pH in the range of 7.2 to 7.8, and oxidation-reduction potential in the range of 840 mV to 960 mV. Microcyn 60 is produced in one concentration only, and need not be activated or diluted. This solution is produced from water obtained by reverse osmosis, which is then subjected to an electrochemical gradient generated by high voltage and sodium chloride. In this way, the reactive species that form in the multiple chambers where the electrochemical gradient is generated are selected in a controlled way to create Microcyn. The result is a solution with a controlled content of free radicals that confer a high oxidation-reduction potential (+840 mV to +960 mV) and consequently high antimicrobial activity.

Hypochlorous acid and sodium hypochlorite are the most abundant elements contained in Microcyn, with others in minor concentration, such as, chloride ions, among others. Although applicants do not wish to be bound by a particular theory, it is believed that the disinfectant effect does not necessarily depend exclusively on the quantity of chlorine, but also may depend on the content of reactive species of oxygen and/or oxygen, or one or more precursors thereof. Also, and in contrast to other superoxidized solutions that have been reported in the literature, Microcyn has a neutral pH (6.4-7.8), is not corrosive and is stable in storage up to 2 years. All these characteristics have made it possible to produce a superoxidized solution that is effective as a high-level disinfectant and compatible for use both on inanimate and biological surfaces (e.g., tissues).

Accelerated stability tests have demonstrated that Microcyn can be stored in widely varying temperature conditions, from 4 to 65° C., without losing its disinfectant activity for a period of 2 years. This property of prolonged stability on the shelf is also the difference from superoxidized solutions reported previously that are only effective if they are used immediately after being produced. In other words, while Microcyn can be stored and distributed even in extreme conditions without losing its antimicrobial activity, other solutions would have to be produced by a specialized and costly machine in every hospital that tried to use that solution. Nevertheless, the manufacturer recommends that, once the container of Microcyn is opened, it be used within 30 days for the purpose of guaranteeing uniform activity and consistent results.

The dose of Microcyn can be changed only by changes in the volume applied per unit area of the skin. In the toxicological studies, the doses of Microcyn applied topically to the intact skin varied between 0.05 and 0.07 mL/cm²; in the study of acute dermatological toxicity and in the investigation of skin irritation, they were up to 8.0 mL/cm², and in those that investigated its application in deep wounds, Microcyn was applied in a dose of 0.09 mL/cm².

Toxicological studies were carried out that applied Microcyn topically to the intact skin, using a single application with exposure of 4 to 24 h. Multiple applications of Microcyn, one or two times a day, during a period of 7 days were assessed for deep wounds in rats.

Two studies were carried out on the intact skin of rabbits to evaluate the effect of Microcyn as to acute irritation and dermal toxicity. No clinical signs, dermal irritation, or abnormalities in the skin at autopsy were found in any of the animals exposed to Microcyn.

The characterization of local and systemic toxicity from topically applied Microcyn to a deep wound was evaluated in rats. No abnormalities, significant differences in the parameters of the blood chemistry or hematic cytology were observed, nor anomalies in the autopsies. The skin irritation gradings and the histopathology of the wounds and the tissues around the place of application did not reveal any difference between the wounds treated with Microcyn and those of the control group treated with saline solution. The deposition of collagen II during the wound healing process was also not altered with the use of Microcyn as measured by immunohistochemistry.

The systemic toxicity of Microcyn was also evaluated by means of an intraperitoneal injection in mice. For this, five mice were injected with a single dose (50 mL/kg) of Microcyn by the intraperitoneal route. In the same way, five control mice were injected with a single dose (50 mL/kg) of saline solution (sodium chloride at 0.9%). In this investigation, neither mortality nor any evidence of systemic toxicity was observed in any of the animals that received the single intraperitoneal dose of Microcyn, for which the LD50 is above 50 mL/kg.

Microcyn was administered by the oral route to rats to allow its absorption and to characterize any inherent toxic effect of the product. For this a single dose (4.98 mL/kg) was administered by esophageal tube to three albino rats of the Sprague-Dawley strain. There was no mortality, nor were there clinical signs or abnormalities in the autopsies of any of the animals exposed to the single oral dose of Microcyn.

The potential of topically applied Microcyn for ocular irritation was also evaluated in rabbits. Ocular irritation was not observed nor any other clinical sign in any animal exposed to Microcyn by topical administration through the ocular route.

Microcyn was applied by the inhalatory route to rats to determine potential acute toxicity by inhalation. All the animals showed a very slight or slight reduction in activity and piloerection after the exposure, but they were all asymptomatic on the following day. Mortality or abnormalities were not observed at autopsy of the animals exposed to Microcyn by inhalation.

Evaluation of the potential for sensitization of the skin with Microcyn was carried out in guinea pigs using a modified occlusion patch method (Buehler). Irritation was not observed in the animals of the control group after a simple treatment challenge, nor in the animals evaluated (treated by induction) after challenge with the treatment. Therefore, Microcyn does not provoke a sensitizing reaction.

The reduction of the microbial load with Microcyn in abdominal wounds in vivo was evaluated in rats. The wall was surgically opened, further closed with a synthetic mesh and then infected with a known *E coli* bacterial load. In these experiments Microcyn demonstrated to be superior to saline solution in reducing the bacterial load. Under macroscopic evaluation, the wound was severely infected only in the saline group. The mesh was exclusively integrated in the abdominal walls of the animals in the Microcyn group. Quantitative cultures in 30 animals per group showed a better reduction in the microbial load with Microcyn reducing the microbial load by 99.997% versus a 99.969% reduction with saline solution. Furthermore, abscess formation was present in 7 animals with MIcrocyn and 17 animals treated with saline solution.

Thus, when it has been applied to the intact skin, deep open dermal wounds, in the conjunctival sac, by oral and inhalation routes or by means of intraperitoneal injection, Microcyn has not shown adverse effects related to the product. There is also experience in having treated more than 500 patients with wounds of very diverse nature in the skin and mucosae, with excellent antiseptic and cosmetic results. Accordingly, topically applied Microcyn should be effective and well-tolerated in this clinical trial.

Microcyn is packaged in transparent 240 mL PET bottles. This product is stored at ambient temperature and remains stable for up to 2 years on the shelf if the bottle is not opened. On having been opened, it is recommended that all of the product be used in less than 90 days. From its profile of high biological safety, Microcyn can be emptied into the sink without risk of contamination or corrosion.

Multiple microbial trials have been run with Microcyn, both in the United States and in Mexico. Eradication of more than 90% of the bacteria occurs in the first few seconds of exposure. The antibacterial and antimycotic activity that Microcyn exhibits in accordance with this standard is summarized in Table 7.

TABLE 7

| Bacterium | Catalog | Time of action (reduction below 99.999%) |
|---|---|---|
| *Ps. aeruginosa* | ATCC 25619 | 1 min |
| *St. aureus* | ATCC 6538 | 1 min |
| *E. coli* | ATCC 11229 | 1 min |
| *S. typhi* | CDC 99 | 1 min |
| *C. albicans* | ATCC | 1 min |
| *B. subtilis* | 9372 | |
| Low spore ($10^4$) | | 10 min |
| High spore ($10^6$) | | 15 min |

The sporicidal activity trial was carried out in accordance with the PAHO [Pan-American Health Organization]/WHO protocol.

Microcyn was found to reduce the viral load of human immunodeficiency virus (strain SF33) by more than 3 logs in five minutes. This was verified by the absence of cytopathic effect and by the level of Agp24 in the trials of virus treated with Microcyn (these trials were undertaken in accordance with the virucide protocols of the United States Environmental Protection Agency (DIS/TSS 7/Nov. 12, 1981.)

The virucidal activity of Microcyn has been confirmed in studies carried out in the United States against HIV and its activity against *Listeria monocytogenes*, MRSA and *Mycobacterium bovis* has also been demonstrated. Thus, it has been demonstrated that Microcyn, when it is administered as recommended, can eradicate bacteria, fungi, viruses and spores from one to fifteen minutes of exposure.

Example 14

This example provides a formulation of the invention suitable for topical administration to a patient. The formulation contains:

| Component | Quantity |
|---|---|
| ORP water solution | 250 mL |
| Carbopol ® polymer powder (thickening agent) | 15 g |
| Triethanolamine (neutralizing agent) | 80 mL |

Example 15

This example provides a formulation of the invention suitable for topical administration to a patient. The formulation contains:

| Component | Quantity |
|---|---|
| ORP water solution | 1000 mL |
| Carbopol ® polymer powder (thickening agent) | 15 g |
| Triethanolamine (neutralizing agent) | 80 mL |

Example 16

This example provides a formulation of the invention suitable for topical administration to a patient. The formulation contains:

| Component | Quantity |
| --- | --- |
| ORP water solution | 250 mL |
| Carbopol ® polymer powder (thickening agent) | 7 g |
| Triethanolamine (neutralizing agent) | 12 mL |

Example 17

This example describes the manufacture of a formulation of the invention comprising an ORP water solution and a thickening agent.

An ORP water solution is put into a suitable container, such as a glass beaker or jar. Carbopol® 974P polymer is passed through a coarse sieve (or strainer), which permits rapid sprinkling, whilst at the same time breaking up any large agglomerates. The polymer Carbopol® 974P is then added as the thickening agent. The Carbopol® polymer is added slowly to prevent the formation of clumps and, thus, avoid an excessively long mixing cycle.

The solution is mixed rapidly during the addition of the Carbopol® polymer so that the powder dissolves at room temperature. The neutralizing agent triethanolamine is then added to the solution and mixed by means of an electric mixer or other suitable device, until a homogeneous gel is obtained. The addition of the neutralizing agent to the Carbopol® polymer composition converts the formulation into a gel.

Example 18

This study demonstrates the effectiveness of the use of an exemplary ORP water solution, Microcyn, in accordance with the invention for the treatment of infected diabetic foot ulcers as compared with conventional wound therapy.

This study was a prospective, single blind, randomized, controlled investigation that compared a Microcyn regimen to a "Control" regimen in the treatment of infected diabetic foot ulcers. Patients were randomized when they met the criteria for the study and when they presented to the diabetic foot clinic. Randomization was by alternate assignment to either Microcyn or Control. Patients were not informed as to whether they were receiving the Microcyn treatment or the Control treatment. However, if a patient happened to become aware of which treatment they were receiving, they were not disqualified from the study.

Forty-five patients were enrolled into the 20 week study. Patients were eligible to be screened if they presented with an infected diabetic foot ulcer. The patients signed an informed consent prior to receiving any study related treatment. Within the Study Population, eight patients (18%) out of the 45 randomized were excluded from the study immediately after the initial assessments due to severe arterial obstruction in the study leg. The patients were transferred to a vascular surgeon for either limb salvage or major amputation. No other patients dropped out during the study.

There were no statistically significant differences with respect to any demographic characteristics between the Microcyn and Control groups (Tables 8 and 9).

TABLE 8

Patient Characteristics

| Parameter | Treatment Group | N | Mean | S.D. | P-Value |
| --- | --- | --- | --- | --- | --- |
| Age (Years) | Microcyn | 21 | 61.9 | 11.9 | NS |
| | Control | 16 | 67.8 | 11.6 | |
| Diabetes Duration (years) | Microcyn | 21 | 16.4 | 8.1 | NS |
| | Control | 16 | 17.0 | 10.2 | |
| Mean Fasting Glycemia | Microcyn | 21 | 163.0 | 59.0 | NS |
| | Control | 16 | 152.0 | 65.8 | |
| Ulcer Duration (weeks) | Microcyn | 21 | 8.58 | 8.50 | NS |
| | Control | 16 | 8.67 | 8.50 | |
| Branch/Ankle Index | Microcyn | 21 | 0.9 | 0.5 | NS |
| | Control | 16 | 1.14 | 0.7 | |

TABLE 9

Patient Gender and Weight

| Parameter | Category | Microcyn n (%) | Control n (%) | P-Value |
| --- | --- | --- | --- | --- |
| Gender | M | 9 (45.0) | 8 (50.0) | NS |
| | F | 12 (55.0) | 8 (50.0) | |
| Obesity | ≦27 kg/m | 15 (71.4) | 12 (75.0) | NS |
| | ≧27 kg/m | 6 (28.6) | 4 (16.0) | |

Patients underwent sharp debridement of the study ulcer to remove necrotic or hyperkeratinized tissue during the study. Patients in the two study arms received similar treatment regimens with the exception that soap and Microcyn were used in place of the povidone iodine and saline rinses. All study wounds received identical dressings, consisting of an application of a gel used in providing a moist wound environment, gauze, and adhesive covering. In addition to instructions to avoid weight bearing as much as possible, patients were provided with off weight bearing custom molded inserts to relieve pressure at the ulcer site, if the ulcer was on a weight bearing area. All patients in both treatment groups were seen daily initially, then depending on the condition of the wound, were required to be seen every third day or once a week.

The Endpoints for the study were as follows: primary—reduction in fetid odor, cellulitis, healing, and safety—serious adverse events. Analysis of the data revealed a relationship between treatment and odor reduction, cellulitis, and healing (Table 10). All patients (100%) in the Microcyn intervention group showed a reduction in fetid odor, compared to only a quarter (25%) of the patients in the Control group. The percentage of patients in the Microcyn intervention group that showed a reduction in cellulitis was approximately 81% compared to about 44% in the Control group. Healing, defined as 1) advancement from infection to the formation of granulation tissue in the wound and 2) development of healthy tissue peri-wound, was observed for the Microcyn intervention group to be about 90% and 94%, respectively. For the Control group, the values were found to be 63% and 31%, respectively.

TABLE 10

Outcomes

| Outcome | Microcyn N (%) | Control N (%) | P-value [1] | NNT [2] |
|---|---|---|---|---|
| Fetid Odor Reduction | 21 (100.0) | 4 (25.0) | 0.001 | 2 |
| Cellulitis Reduction | 17 (80.9) | 7 (43.7) | 0.01 | 3 |
| Healing | | | | |
| Advances from infection to granulating tissue | 19 (90.4) | 10 (62.5) | 0.05 | 4 |
| Improvement of tissue and skin around the ulcer | 19 (90.4) | 5 (31.2) | 0.001 | 2 |

[1] P-values based on Yates correction for chi-squared.
[2] NNT = Number needed to treat. NNT significant clinical efficacy range = 2-4

Thus, patients treated with Microcyn showed an important, clinical benefit with respect to the reduction of fetid odor, cellulitis, and healing when compared to patients treated with conventional therapy alone.

Example 19

This example demonstrates the efficacy of an exemplary ORP water solution, Dermacyn, for the treatment of diabetic foor ulcers and for decreasing micorbial load and/or complications associated with diabetic foot ulcers, particularly, recurrence, dehiscence and amputation.

Infection in the presence of peripheral vascular disease is considered to be one of the most important prognostic factor for the risk of amputation in diabetic foot disease. Antibiotic therapy, surgical treatment of deep infection and antiseptic dressings are commonly used for the treatment of infection in diabetic foot. The value of local control of infection in healing diabetic wounds is recognized as critical for wound healing.

This was an open-label (not blinded), single centre study. The global treatment of all subjects included general antibiotic therapy, surgery and weight bearing relief. The Dermacyn treated group (Group D) was recruited prospectively. Once all subjects in this group had been treated, data for the control group of povidone iodine treated subjects (Group C) were collected retrospectively from the medical records.

Subjects were males and females of over 18 years of age with a history of diabetes and at least one HbAC1 reading and stage II/III B-D ulcers using the Texas University Classification (T.U.C.), which were all localized below the ankle. After the completion of the treatment of Group D, Group C were matched for age, duration of diabetes and class of ulceration using the T.U.C. before their data were collected.

Treatment was given to all subjects following the clinician's standard care protocol so the same treatment was given to both groups (apart from the use of Dermacyn or povidone iodine). All subjects were on antibiotic therapy for at least one week prior to the start of treatment. Microbiological specimens were taken at enrolment (or the equivalent start of treatment in the control group) and then every month until surgical closure treatment. Local treatment was carried out daily using gauze with Dermacyn or gauze with povidone iodine.

Treatment took part in two stages:

Stage I—Subjects underwent debridement of their ulcers. They then had gauze soaked in either Dermacyn or povidone iodine applied to the wound sites for the next 24 hours. These dressings were changed daily. All subjects with peripheral vascular disease were referred for revascularization using endovascular techniques or by-pass surgery before any elective surgery took place. In subjects with T.U.C. III B/D lesions, surgical treatment of bone infection was carried out (esostectomy-minor amputations). Subjects were discharged 10-20 days prior to conducting the definitive closure surgery.

Stage II—Subjects were then re-admitted for debridement and surgery as required (i.e. conservative, minor or major). Following surgery, subjects had gauze soaked in either Dermacyn or povidone iodine (as previously allocated) applied to the wound sites and left in place for 24 hours. These dressings were then changed daily.

The primary outcome measure was the microbial load reduction (demonstrated by number of positive cultures at entry and at surgery or during follow up). Secondary outcome measures were: healing time (in days), recurrence (in days), type of re-operation (conservative, minor or major), dehiscence and local adverse effects. The analysis consists of basic descriptive statistics and a statistical analysis of the effect of treatment on microbiological outcomes at surgery. To analyse the effect of Dermacyn treatment on microbial load at surgery, the microbial load at surgery was dichotomised into a successful or unsuccessful outcome, where zero bacterial strains was considered successful and any non-zero number of bacterial strains was considered unsuccessful. The difference between the two treatment groups in the proportion of successful microbiological outcomes was tested for statistical significance using Fisher's exact test. In addition, the odds ratio for the odds of a successful outcome was calculated by logistic regression. These analyses were post-hoc analyses.

Data have been recorded for 218 subjects, of whom 110 were treated with Dermacyn (Group D) and 108 were treated with povidone iodine (Group C). The mean age of the subjects was 69.6 years, and 33.5% were female. The mean duration of diabetes at entry was 17.4 years. Demographic characteristics were well balanced between the two groups. Baseline demographics are given in Tables 11 and 12.

TABLE 11

Summary of Age (years)

| | Treatment Group | | |
|---|---|---|---|
| | Group D | Group C | All subjects |
| N | 110 | 108 | 218 |
| Mean | 69.4 | 69.8 | 69.6 |
| SD | 8.45 | 7.53 | 7.99 |
| Median | 70 | 70 | 70 |
| Minimum | 40 | 50 | 40 |
| Maximum | 91 | 88 | 91 |

TABLE 12

Summary of Sex

| | Treatment Group (n and %) | | | | | |
|---|---|---|---|---|---|---|
| | Group D | | Group C | | All subjects | |
| | n | % | n | % | n | % |
| Male | 69 | 62.7 | 76 | 70.4 | 145 | 66.5 |
| Female | 41 | 37.3 | 32 | 29.6 | 73 | 33.5 |

The mean number of bacterial strains was well balanced between the two groups, although more subjects in Group D (39) than Group C (27) had only one bacterial strain on entry. The microbial load reduction at surgery (or follow up) was significantly higher in Group D than in Group C. If a successful outcome is defined as zero bacterial strains after surgery, the number of subjects for whom treatment was a success was 97 in Group D, compared to 74 in Group C. The differences between the treatment groups in the proportion of microbiological success was significant (p<0.001, Fisher's exact test). Consistent with this, the odds ratio for a successful outcome was 3.4 (95% CI 1.7-7.0) for patients treated with Dermacyn.

A summary of the number of bacterial strains before and after surgery (in categories) is shown in Table 13, and a summary of successful microbiological outcome (successful outcome being defined as zero bacterial strains after surgery) is shown in Table 14.

TABLE 13

Summary of number of bacterial strains before and after surgery (in categories)

| Number of bacterial strains | Group D before surgery n (%) | Group D after surgery n (%) | Group C before surgery n (%) | Group C after surgery n (%) | All subjects before surgery n (%) | All subjects after surgery n (%) |
|---|---|---|---|---|---|---|
| 1 | 39 (35.8) | 97 (88.2) | 27 (25.2) | 74 (68.5) | 66 (30.6) | 171 (78.4) |
| 2 | 28 (25.7) | 12 (10.9) | 39 (36.4) | 25 (23.1) | 67 (31.0) | 37 (17.0) |
| 3 | 34 (31.2) | 1 (0.9) | 38 (35.5) | 9 (8.3) | 72 (33.3) | 10 (4.6) |
| 4 | 7 (6.4) | — | 2 (1.9) | — | 9 (4.2) | — |
| 5 | 1 (0.9) | — | 1 (0.9) | — | 2 (0.9) | — |

TABLE 14

Summary of successful microbiological outcome (successful outcome is defined as zero bacterial strains after surgery)

| Successful treatment | Group D n | Group D (%) | Group C n | Group C (%) | All subjects n | All subjects (%) |
|---|---|---|---|---|---|---|
| Yes | 97 | 88.2 | 74 | 68.5 | 171 | 78.4 |
| No | 13 | 11.8 | 34 | 31.5 | 47 | 21.6 |

The mean healing time was slightly shorter in Group D (45.2 days) than in Group C (58 days). The summary of healing times is shown in Table 15. The recurrence rate was slightly higher in Group C (12 recurrences) than in Group D (10 recurrences). The summary of re-ulceration (recurrence) is shown in Table 16.

TABLE 15

Summary of Healing Time (in days)

| | Treatment Group (n and %) | | |
|---|---|---|---|
| | Group D | Group C | All subjects |
| N | 110 | 108 | 218 |
| Mean | 45.2 | 58 | 51.6 |
| SD | 14.4 | 20 | 18.5 |
| Median | 43 | 55 | 48 |
| Minimum | 20 | 21 | 20 |
| Maximum | 87 | 125 | 125 |

TABLE 16

Summary of re-ulceration (recurrence)

| Re-ulceration occurrence | Group D n | Group D % | Group C n | Group C % | All subjects n | All subjects % |
|---|---|---|---|---|---|---|
| Yes | 10 | 9.1 | 12 | 11.1 | 22 | 10.1 |
| No | 100 | 90.9 | 96 | 88.9 | 196 | 89.9 |

A greater number of subjects in Group D (60) had conservative surgical treatment than in Group C (47), and there were 50 subjects in Group D who required some form of amputation, compared to 61 in Group C (shown in Table 17). A summary of the type of surgery is shown in Table 18.

TABLE 17

Summary of Category of Surgery

| | Treatment Group (n and %) | | | | | |
|---|---|---|---|---|---|---|
| | Group D | | Group C | | All subjects | |
| Type of Surgery | n | % | n | % | n | % |
| Conservative treatment | 60 | 54.5 | 47 | 43.5 | 107 | 49.1 |
| Minor amputations | 45 | 40.9 | 51 | 47.2 | 96 | 44 |
| Major amputations | 5 | 4.5 | 10 | 9.3 | 15 | 6.9 |

TABLE 18

Summary of Detailed Type of Surgery

| | Treatment Group (n and %) | | | | | |
|---|---|---|---|---|---|---|
| | Group D | | Group C | | All subjects | |
| Surgical procedure | n | % | n | % | n | % |
| Above knee amputation | 0 | 0.0 | 3 | 2.8 | 3 | 1.4 |
| Below knee amputation | 5 | 4.5 | 7 | 6.5 | 12 | 5.5 |
| Chopart amputation | 2 | 1.8 | 1 | 0.9 | 3 | 1.4 |
| Debridement | 2 | 1.8 | 2 | 1.9 | 4 | 1.8 |
| Dressing | 14 | 12.7 | 7 | 6.5 | 21 | 9.6 |
| Lisfranc amputation | 2 | 1.8 | 2 | 1.9 | 4 | 1.8 |
| Panmetatarsal head resection (resection of all metatarsale heads) | 8 | 7.3 | 7 | 6.5 | 15 | 6.9 |
| Ray amputation (single) | 15 | 13.6 | 17 | 15.7 | 32 | 14.7 |
| Ray amputations (plural) | 3 | 2.7 | 3 | 2.8 | 6 | 2.8 |
| Skin graft | 7 | 6.4 | 7 | 6.5 | 14 | 6.4 |
| Transmetatarsal amputation | 11 | 10.0 | 19 | 17.6 | 30 | 13.8 |
| Toe amputation (single) | 8 | 7.3 | 5 | 4.6 | 13 | 6.0 |
| Toe amputations (plural) | 4 | 3.6 | 4 | 3.7 | 8 | 3.7 |
| Ulcerectomy | 1 | 0.9 | 3 | 2.8 | 4 | 1.8 |
| Ulcerectomy and resection of bone (sequestrectomy) | 28 | 25.5 | 21 | 19.4 | 49 | 22.5 |

Occurrences of surgical dehiscence (the situation of not healing after surgery due to infection or ischemia) were slightly higher in Group C (21) than in Group D (14). The summary of surgical dehiscence is shown in Table 19.

TABLE 19

Summary of surgical dehiscence

| Surgical Dehiscence | Treatment Group (n and %) | | | | | |
|---|---|---|---|---|---|---|
| | Group D | | Group C | | All subjects | |
| | n | % | n | % | n | % |
| Yes | 14 | 12.7 | 21 | 19.4 | 35 | 16.1 |
| No | 96 | 87.3 | 87 | 80.6 | 183 | 83.9 |

There were no local adverse effects reported in the Group D compared to 18 reported in Group C. The summary of the rate of local adverse effects is shown in Table 20.

TABLE 20

Summary of local adverse effects

| Event occurrence | Treatment Group (n and %) | | | | | |
|---|---|---|---|---|---|---|
| | Group D | | Group C | | All subjects | |
| | n | % | n | % | n | % |
| Yes | 0 | 0.0 | 18 | 16.7 | 18 | 8.3 |
| No | 110 | 100 | 90 | 83.3 | 100 | 91.7 |

This example demonstrates that treatment with the exemplary ORP water solution, Dermacyn, resulted in fewer bacterial strains isolated, fewer local adverse effects, fewer surgical dehiscences, and shorter healing times than was observed with conventional therapy. Thus, this example is believed to demonstrate that the treatment of diabetic foot ulcers with Dermacyn has therapeutic advantages over conventional povidone iodine topical therapy.

Example 20

This study demonstrates the effectiveness of an exemplary ORP water solution, Dermacyn (M60), for the treatment of venous stasis skin ulcers.

A total of 61 adults (56 women, 5 men) with a venous stasis skin ulcer resultin from varicose veins of at least 10 year's duration, at least 3 cm in length or width and an ankle:brachial pressure index of at least 0.8 were included. Over twelve months thirty five patients (31 women, 4 men) were treated with venous sclerotherapy, compressive bandage and Dermacyn. The results were compared to those obtained in a historical control group (25 women, 1 man) treated with venous sclerotherapy, compressive bandage and povidone iodine. The age distributions (Table 21) and site of the ulcers (Table 22) were similar for the two groups.

TABLE 21

Age Distribution.

| | Microcyn | | Control | |
|---|---|---|---|---|
| Age (y) | No. | % | No. | % |
| 20 a 29 | — | — | 2 | 7.7 |
| 30 a 39 | 2 | 5.7 | 2 | 7.7 |
| 40 a 49 | 4 | 11.4 | 4 | 15.4 |
| 50 a 59 | 6 | 17.1 | 6 | 23.0 |
| 60 a 69 | 18 | 51.4 | 7 | 26.9 |

TABLE 21-continued

Age Distribution.

| | Microcyn | | Control | |
|---|---|---|---|---|
| Age (y) | No. | % | No. | % |
| 70 a 79 | 4 | 11.4 | 4 | 15.4 |
| 80 a 89 | 1 | 2.9 | 1 | 3.8 |
| Total | 35 | 100.0 | 26 | 100.0 |

TABLE 22

Site of ulcer.

| VEIN INSUFFICIENCY | Microcyn | CONTROL |
|---|---|---|
| Superficial | 14 | 21 |
| Bilateral | 5 | 3 |
| Internal | 7 | 0 |
| Left Leg | 5 | 2 |
| Right Leg | 4 | 0 |

The control group included 82 ulcers and the Dermacyn-treated group 100 ulcers.

Wound disinfection was recommended once daily with either agent (i.e. Dermacyn or povidone iodine). Antibotics were administered to 65.4% of the control patients and 68.6% of the Dermacyn-treated patients. The follow-up continued until the patient's reference leg was ulcer healed or for a minimum of 12 months.

Figure 4:
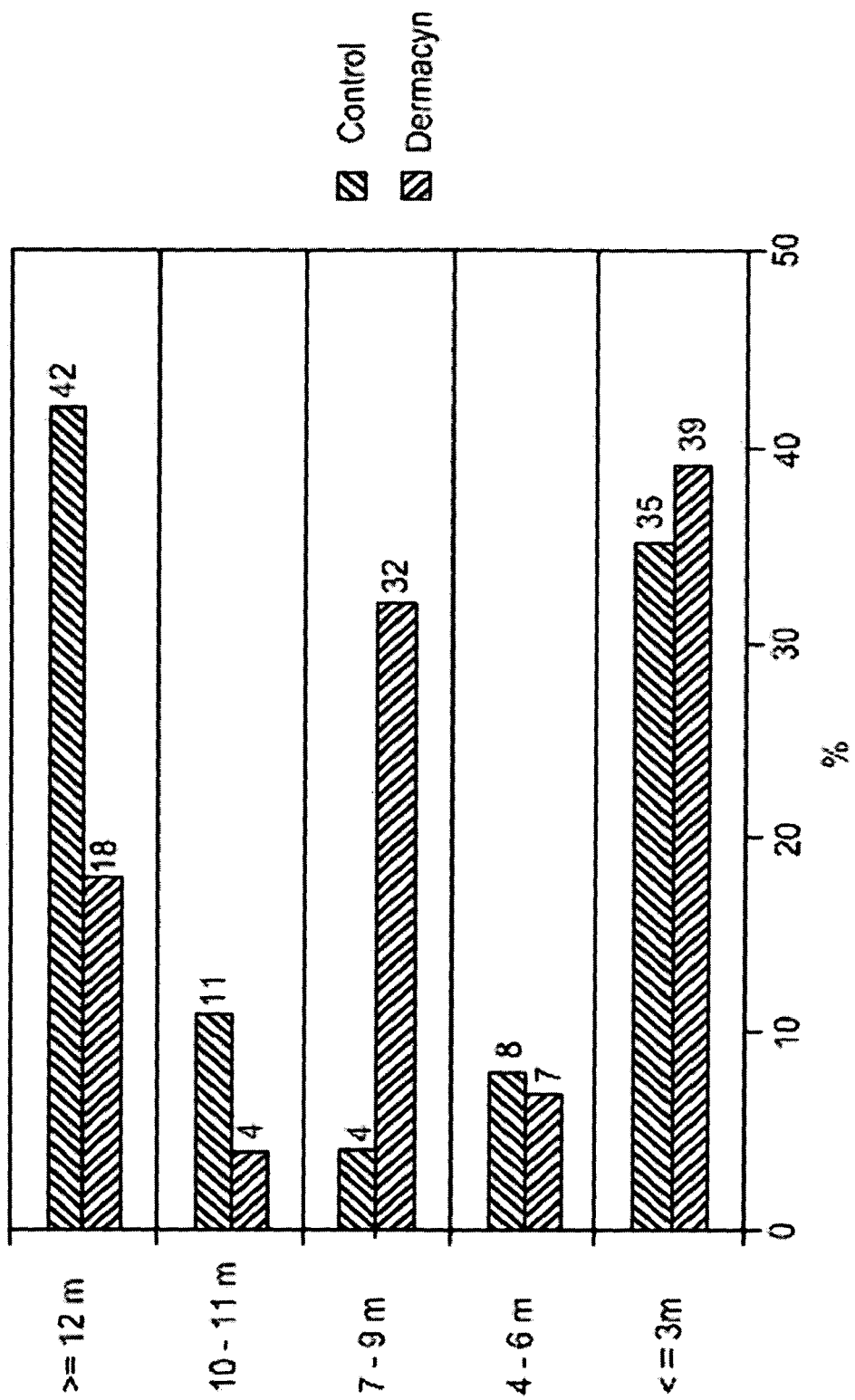
FIG. 4 depicts a graphical comparison of the number of meters control and ORP water solution-treated (Dermacyn) patients can walk.
Figure 5:
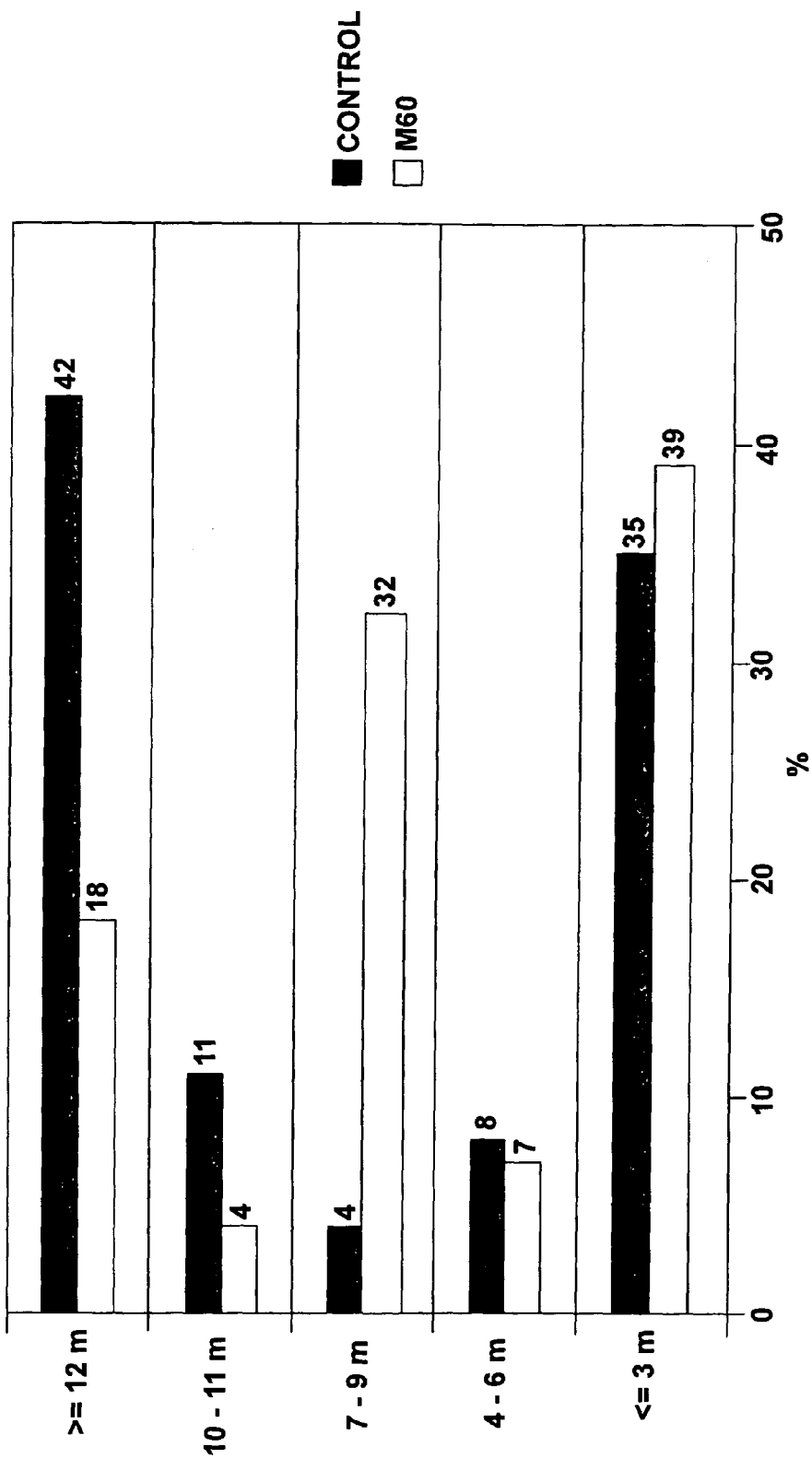
FIG. 5 depicts a graphical comparison of the number of months required for ulcers to heal in control and ORP water solution-treated (M60) patients (>=12 m, greater than or equal to 12 months; 10-11 m, 10-11 months; 7-9 m, 7-9 months; 4-6 m, 4-6 months; <=3 m, less than or equal to 3 months) (in percent of all ulcers in the group).

The primary end-point was quality of life. For this purpose a validated QOL-SF36 scale was used (Sam et. al., *Eur J Vasc Endovasc Surg.* 2004, 28:253-256.) Secondary outcomes were the complete healing of ulcers on the trial leg and adverse events. FIG. 4 shows the improvement in overall physical activity in the Dermacyn group patients compared with controls. In addition, 78% of the ulcers treated with Dermacyn versus only 47% in the control group healed in by 9 months (see FIG. 5).

Figure 6:
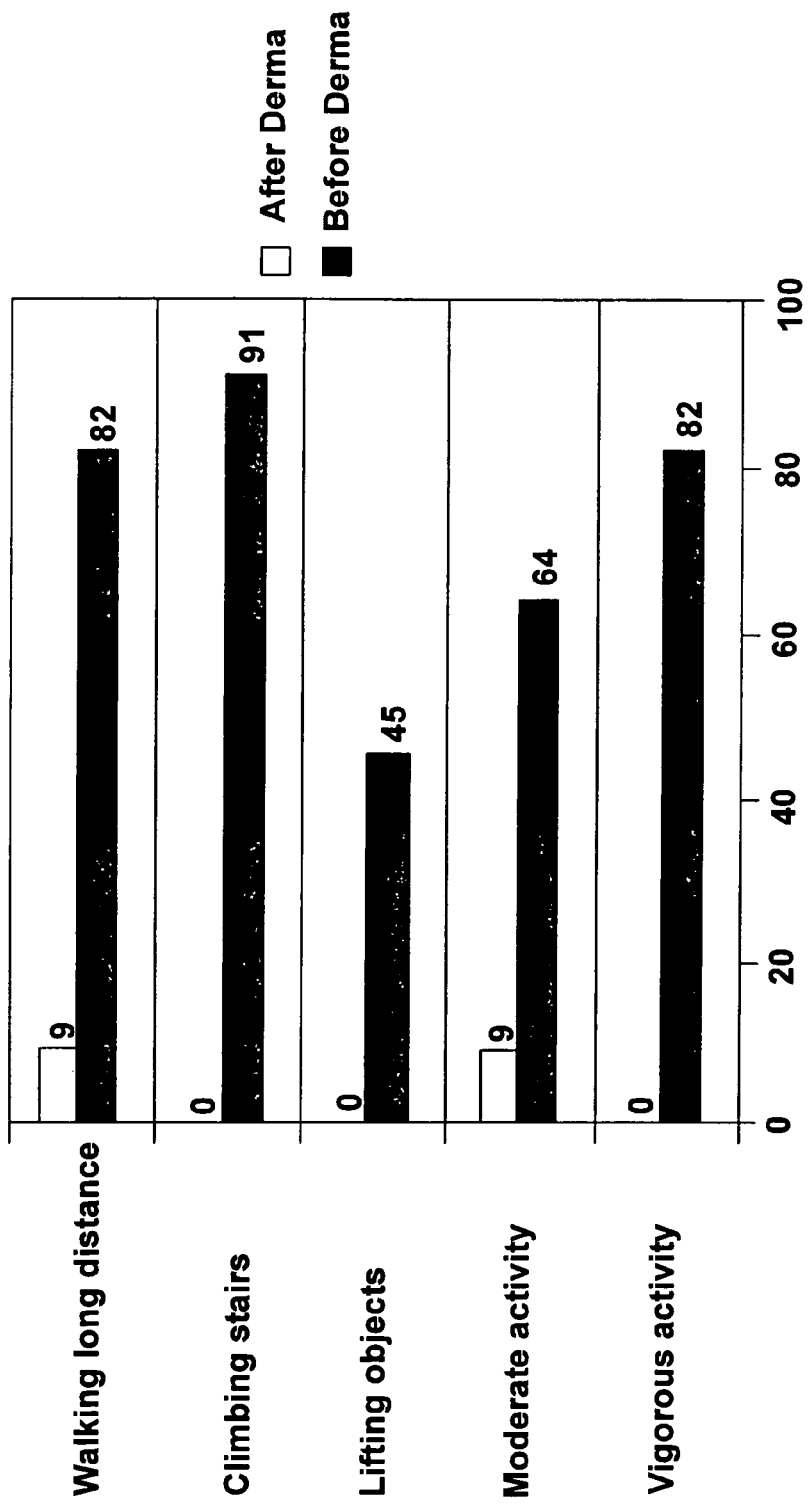
FIG. 6 depicts a graphical comparison of the functional status, based on ability to perform the listed tasks, of patients before and after ORP water solution (Derma)-treatment.
Figure 7:
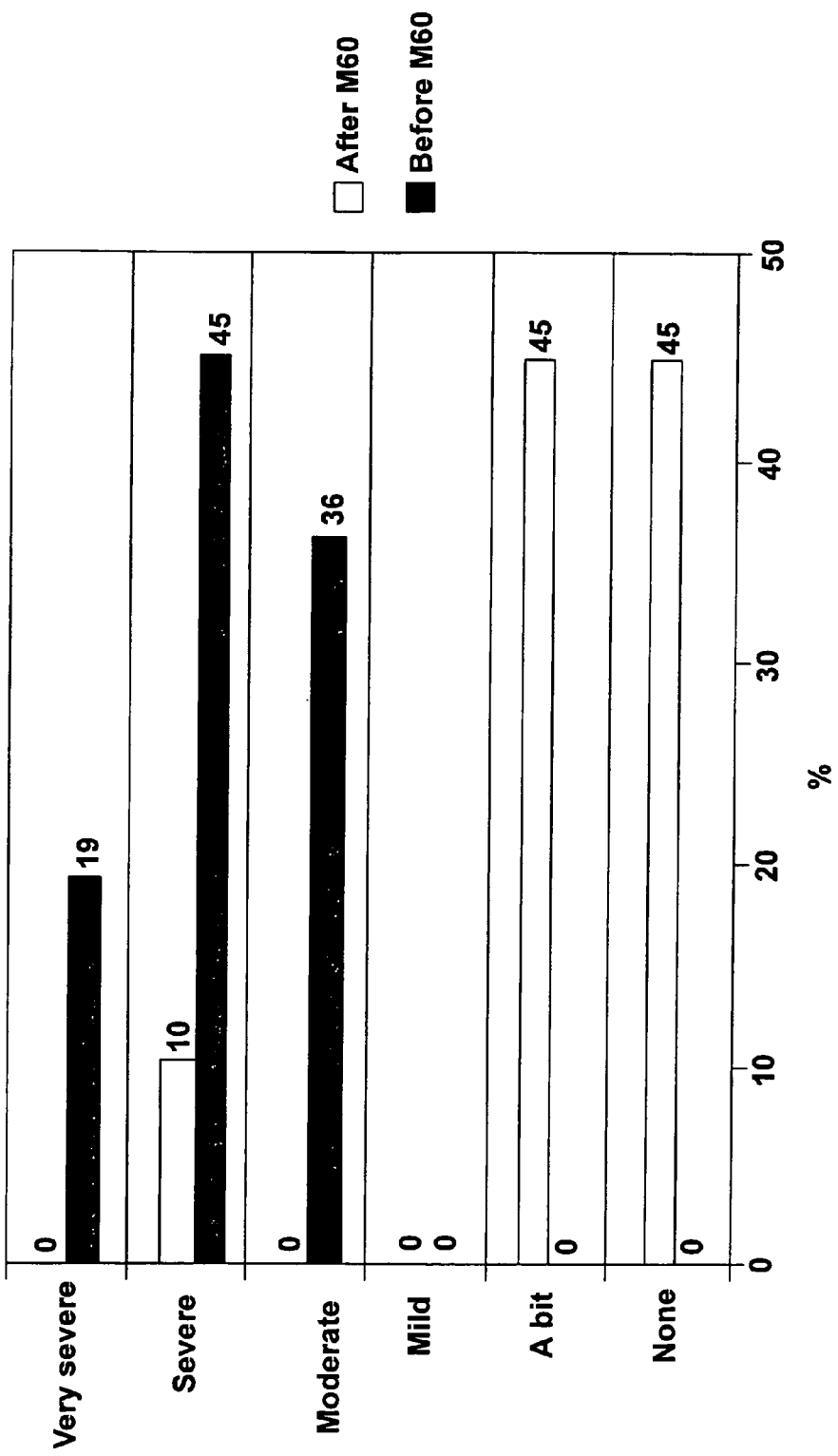
FIG. 7 depicts a graphical comparison of pain associated with ulcers reported by patients before and after ORP water solution (M60)-treatment.

The only side effect found at the time of application was burning sensation in up to 30% of patients of Dermacyn-treated patients. This sensation was self limited and lasted few minutes at the most. It also disappeared in the second or third day of application and had not impact in the healing process, as can be observed in FIG. 6, which shows the functional improvements made by Dermacyn-treated patients. In addition, the Dermacyn-treated patients showed improvements in pain intensity with ORP water treatment (FIG. 7). The Dermacyn-treated patients also showed improvements in vitality, social function, and overall mental health.

This study shows that venous leg skin ulcers treated with Dermacyn had a better quality of life in comparison to those treated with povidone iodine during the study.

Example 21

This study can be done to demonstrate the safety and efficacy of an exemplary ORP water solution, Dermacyn, used in accordance with the invention as a replacement solution for the Versajet™ (Smith & Nephew) jet lavage system in the treatment of necrotic tissue (ulcers) distal to the malleoli, as compared to the standard regimen.

This will be a prospective randomized, double-blind, controlled study. Approximately 30 patients (about 20 in the Dermacyn group/about 10 in the Control group) will be enrolled in the study. The population for this study will be patients with lower extremity ulcers (e.g., diabetic foot ulcers, venous stasis ulcers). All of the study's inclusion and exclusion criteria must be satisfied by the Day 0 for the patient to be eligible for enrollment into the study. The inclusion criteria are: patient is 18 years old or older; patient's lower extremity ulcer has necrotic tissue present and is a candidate for mechanical debridement by the jet lavage system; patient's ulcer is located distal to the malleoli; patient's ulcer surface area is greater than or equal to 1.0 cm$^2$; patient's ulcer extends through the dermis and into subcutaneous tissue (granulation tissue may be present), with possible exposure of muscle, or tendon, but without bone, and/or joint capsule involvement; and patient's Ankle-Arm Index by Doppler is an ABI of greater than or equal to 0.8 or patient's toe pressure is greater than or equal to 40 mmHg.

The exclusion criteria are: patient has clinical evidence of gangrene on any part of the treatment limb; patient's ulcer is expected to be resected or amputated during the study period; patient's has the following signs of a systemic inflammatory response syndrome (SIRS); patient's ulcer has a total surface area that is less than 1 cm$^2$; patient has one or more medical condition(s) (including renal, hepatic, hematologic, neurologic, or immune disease) that in the opinion of the investigator would make the patient an inappropriate candidate for this study; patient has known active alcohol or drug abuse; patient is receiving oral or parenteral corticosteroids, immunosuppressive or cytotoxic agents, or is anticipated to require such agents during the course of the study; patient has known allergies to chlorine; patient's ulcer is accompanied by osteomyelitis; and patient has any condition(s) which seriously compromises the patient's ability to complete this study.

After the informed consent has been obtained, inclusion and exclusion criteria met, the patient will be randomized (2:1 randomization) into one of the following treatments: Treatment—Dermacyn with the jet lavage system, plus the use of a hydrogel wound dressing regimen; Control—Saline (standard treatment with the jet lavage systems), plus the use of a hydrogel wound dressing regimen.

Each patient randomized to Dermacyn will receive applications of the study product Dermacyn, with the Versajet jet lavage system during mechanical debridement of the patient's wound. A standard pressure setting on the Versajet will be used for diabetic foot ulcers, which will be distal to the malleoli. After debridement, Dermacyn will be applied onto the wound in sufficient quantities to rinse the wound bed free of debris. The wound will be covered with a hydrogel dressing. At every dressing change, the wound will be rinsed out with Dermacyn and covered with a new hydrogel dressing. The dressings will be changed every 3 days, unless otherwise specified by the investigator. The clinical response factors (CFRs) ((1) reduction of bacteria in the wound, (2) reduction in wound area, and (3) development of granulation tissue) will be determined during the weekly visits.

Each Control patient will receive applications of the Control product (saline solution) with the Versajet jet lavage system during mechanical debridement of the patient's wound. After debridement, saline will be applied onto the wound in sufficient quantities to rinse the wound bed free of debris. The wound will be covered with a hydrogel dressing. At every dressing change, the wound will be rinsed out with saline and covered with a new hydrogel dressing. The dressings will be changed every 3 days, unless otherwise specified by the investigator. The clinical response factors will be determined during the weekly visits.

Debridement of the wound may be performed at each weekly visit. Any necrotic tissue will be debrided with jet lavage prior to the wound assessments. Debris from the ulcer will be rinsed with either Dermacyn or saline (dependent upon the randomization). Between visits the patient will rinse the wound with Dermacyn or saline (dependent upon randomization) at every dressing change. Photographs of the wound will be taken at every visit after debridement.

The primary efficacy endpoints will be: (1) reduction of bacteria in the wound, (2) reduction in wound area, and (3) development of granulation tissue. Safety will be assessed in all patients who are randomized in the study. The treatment of emergent and serious adverse events will be recorded.

Example 22

This study will demonstrate the safety and efficacy of an exemplary ORP water solution, Dermacyn, as a replacement solution for the Jet-Ox ND lavage system in the treatment of necrotic tissue in lower extremity ulcers as compared to the standard regimen used by the Jet-Ox ND system.

The Jet-Ox ND system removes necrotic tissue from chronic wounds via a controlled spray lavage of sterile saline, without damage to underlying healthy tissues. This study will replace saline with Dermacyn, which is expected to provide the same spray lavage effect and additionally reduce the bacterial load of the wound that may be inhibiting wound closure.

Twenty patients will be studied (randomized to yield 10 Dermacyn patients and 10 Control patients). The inclusion criteria will be: patient is older than 18 years; patient has a lower extremity below-the-knee ulcer with necrotic tissue present and is a candidate for mechanical debridement with the Jet-Ox ND lavage system; patients ulcer has been present >30 days prior to the screening visit; the ulcer surface area is >1 cm2 the ulcer extends through the dermis and into subcutaneous tissue (granulation tissue may be present) with possible exposure of muscle, tendon but, without exposed bone or capsule; patients ankle/arm index by doppler is >0.8 and/or patients toe pressure is >40 mmHg; and the patient has a palpable pulse at the dorsalis pedis and/or posterior tibial artery.

There will be the following exclusion criteria: renal, hepatic, hematologic, neurologic or immuno-compromised patients, including having Human Immunodeficiency virus (HIV) or Acquired Immunodeficiency Syndrome (AIDS); that in the opinion of the investigator would make the patient an inappropriate candidate for the study; wounds with the following clinical signs of infection; gangrene on any part of the treatment limb; ulcer exhibits exposed bone (positive probe to bone) or has other evidence of underlying osteomyelitis at the ulcer site; expectation that the infected ulcer will be amputated or resected during the study period; severe malnutrition as evidenced by an albumin of <2.0; known alcohol or drug abuse; patients receiving oral or parenteral corticosteroids, immunosuppressive or cytotoxic agents, coumadin, heparin, or is anticipated to require such agents during the course of the study; and patient has known allergy to chlorine.

Each individual will be randomized into one of two treatment arms; Dermacyn or saline. The target ulcer will receive mechanical debridement, followed by irrigation of the wound with either Dermacyn or saline and bandaging with a hydrogel dressing. A central wound biopsy for quantitive culture will be taken, along with laboratory studies (hematology, serum chemistry and pregnancy testing as appropriate), non-invasive peripheral vascular studies, medical history and physical examination, ulcer tracings, and ulcer photographs.

A Jet-Ox ND lavage system will be dispensed along with Dermacyn or saline, hydrogel and bandaging materials. Directions for home use will be provided. Visits will include screening, enrollment [day 0] with randomization, weekly visits with debridement, photographs and assessments. Efficacy will be determined by (1) reduction of bacteria in the wound, (2) reduction in wound area, and (3) development of granulation tissue during the course of the study. Safety will be assessed in all patients who are randomized in the study. Treatment emergent and serious adverse events will be recorded.

Example 23

This example demonstrates the effect of an exemplary ORP water solution versus hydrogen peroxide (HP) on the viability of human diploid fibroblasts (HDFs). To study this potential toxicity, HDFs were exposed in vitro to ORP water solution and hydrogen peroxide (HP). HP is known to be toxic to eukaryotic cells, increasing apoptosis and necrosis and reducing cellular viability. In this example, cell viability, apoptosis and necrosis were measured in HDFs exposed to pure ORP water solution and 880 mM HP (a concentration employed for antiseptic uses of HP) for 5 and 30 minutes.

Figure 8A:
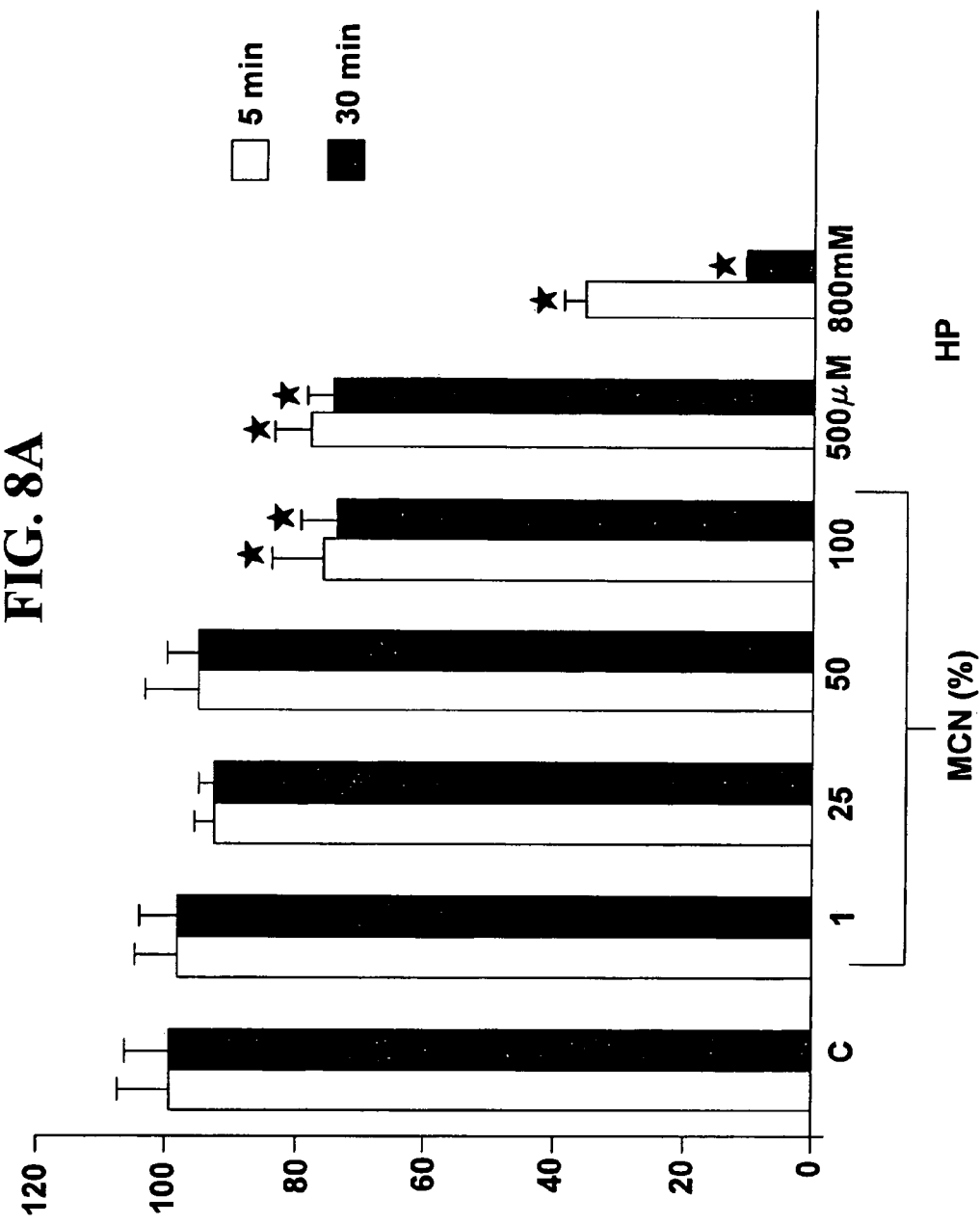
FIGS. 8A-8C depicts a graphical comparison of cell viability, apoptosis and necrosis in human dermal fibroblasts (HDFs) treated with an exemplary ORP water solution (MCN) versus hydrogen peroxide (HP).
Figure 8B:
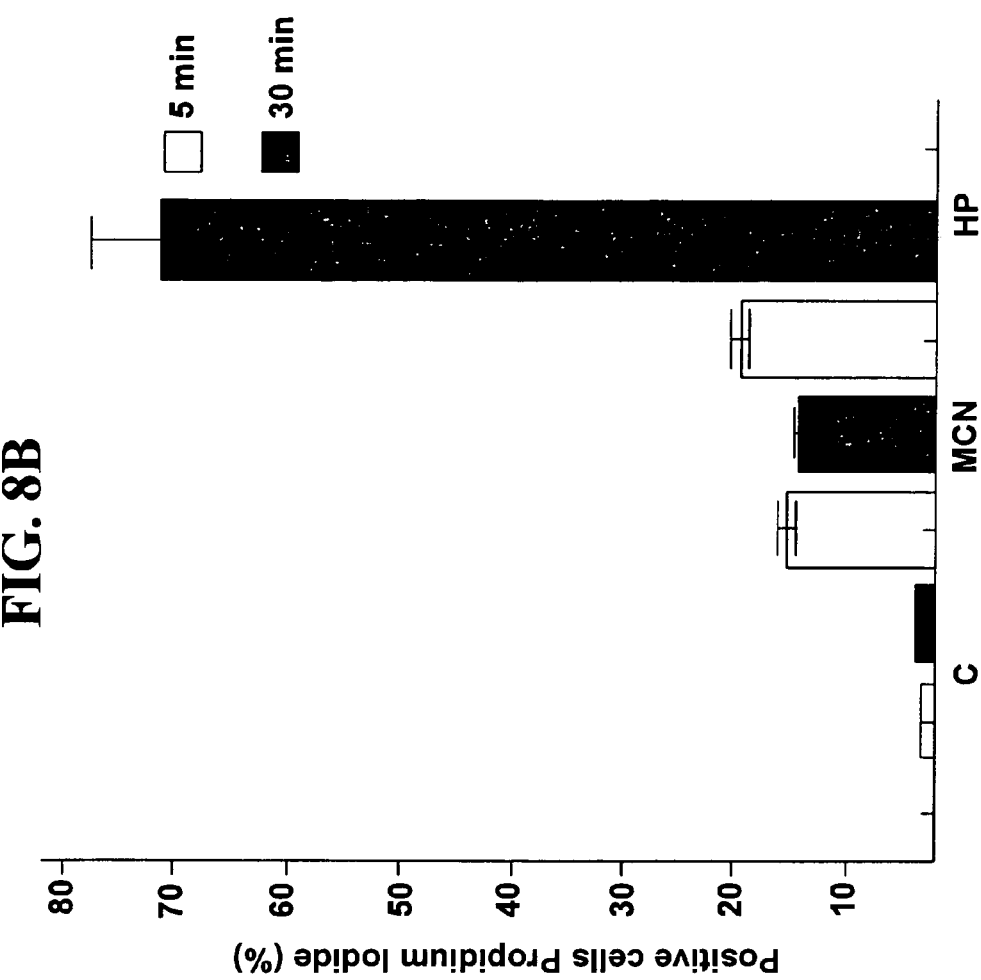
Figure 8C:
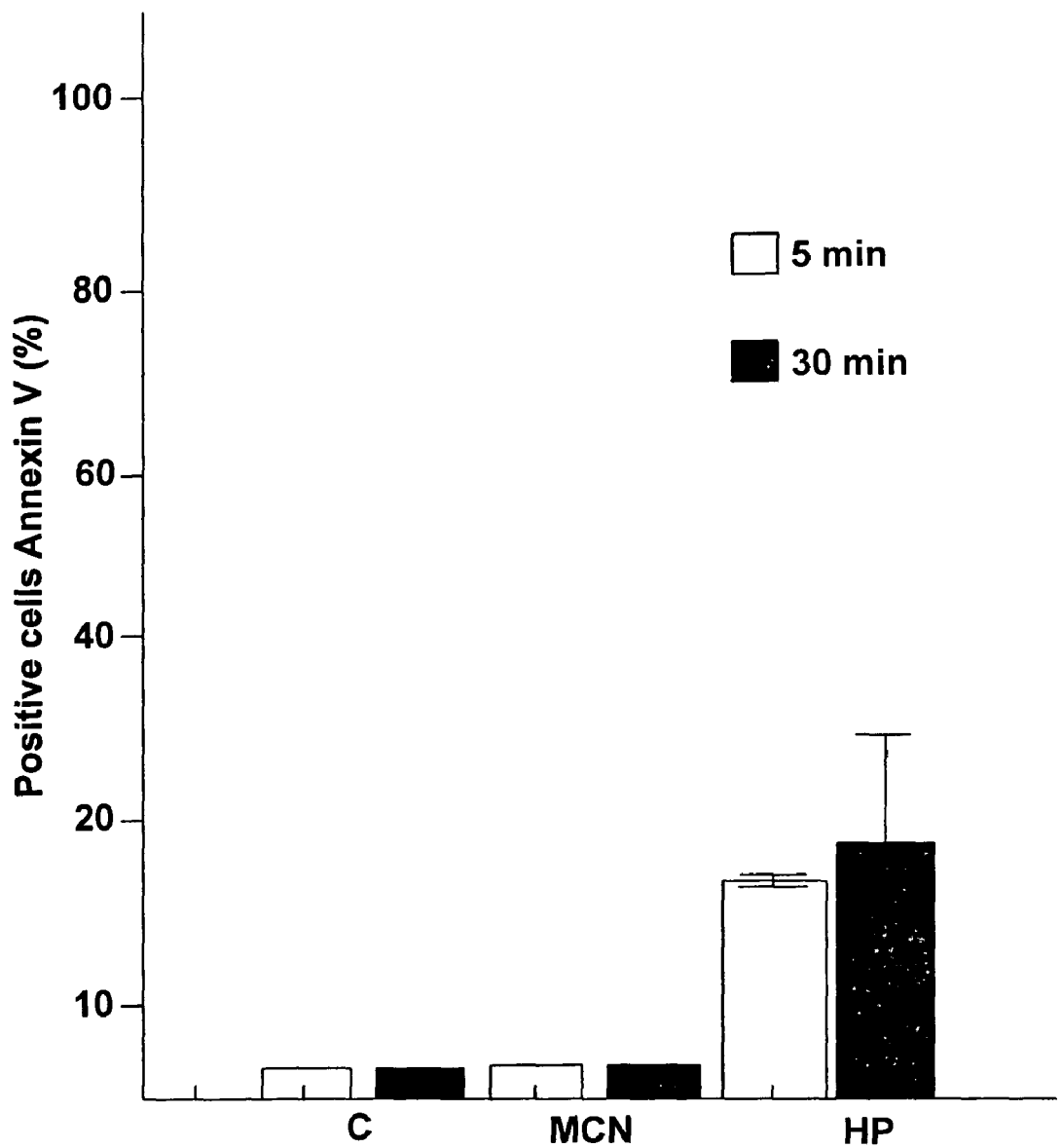

HDF cultures were obtained from three different foreskins, which were pooled and cryopreserved together for the purpose of this study. Only diploid cells were used for all experiments. On cell cycle analysis, DNA diploidy was defined as the presence of a single G0-G1 peak with a CV<7% and a corresponding G2/M peak collected from at least 20,000 total events. FIGS. 8A-8C discloses the results with exposure times of 5 and 30 minutes are depicted in white and black bars, respectively. Simultaneous analyses of these parameters were performed in the same cell populations by flow cytometry using: A) 7-aminoactinomycin D (7AAD); B) Annexin V-FITC and C) Propidium iodide. FIGS. 8A-8C disclose percentage values expressed as mean±SD (n=3).

Cell viability was 75% and 55% after a 5 minute exposure to ORP water solution and HP, respectively (FIG. 8A). If the exposure was prolonged to 30 min, cell viability further decreased to 60% and 5%, respectively. Apparently, the ORP water solution induced cell death through necrosis because 15% of the cells incorporated propidium iodide in the flow cytometry analysis at both times (FIG. 8C). While not wanting to be bound by any particular theory, this result could be due to an osmotic effect induced by the hypotonicity of Microcyn (13mOsm) since the cells were kept in the ORP water solution only, without added growth factors or ions. Apoptosis does not seem to be the mechanism by which the ORP water solution induces cell death because only 3% of ORP water solution-treated cells exposed Annexin-V in the cellular surface (a marker of apoptosis) (FIG. 8B). This percentage was actually similar to the one measured in the control group. On the contrary, HP induced necrosis in 20% and 75% of treated cells and apoptosis in 15% and 20% after 5 and 30 min of exposure, respectively. Altogether these results show that the (undiluted) ORP water solution is far less toxic for HDFs than an antiseptic concentration of HP.

Example 24

This example demonstrates the effect of an exemplary ORP water solution relative to hydrogen peroxide (HP) on oxidative DNA damage and formation of the DNA adduct 8-hydroxy-2'-deoxiguanosine (8-OHdG) in HDFs. It is known that the production of 8-OHdG adducts in a cell is a marker of oxidative damage at specific residues of DNA. In addition, high cellular levels of this adduct correlate with mutagenesis, carcinogenesis and cellular aging.

Figure 9:
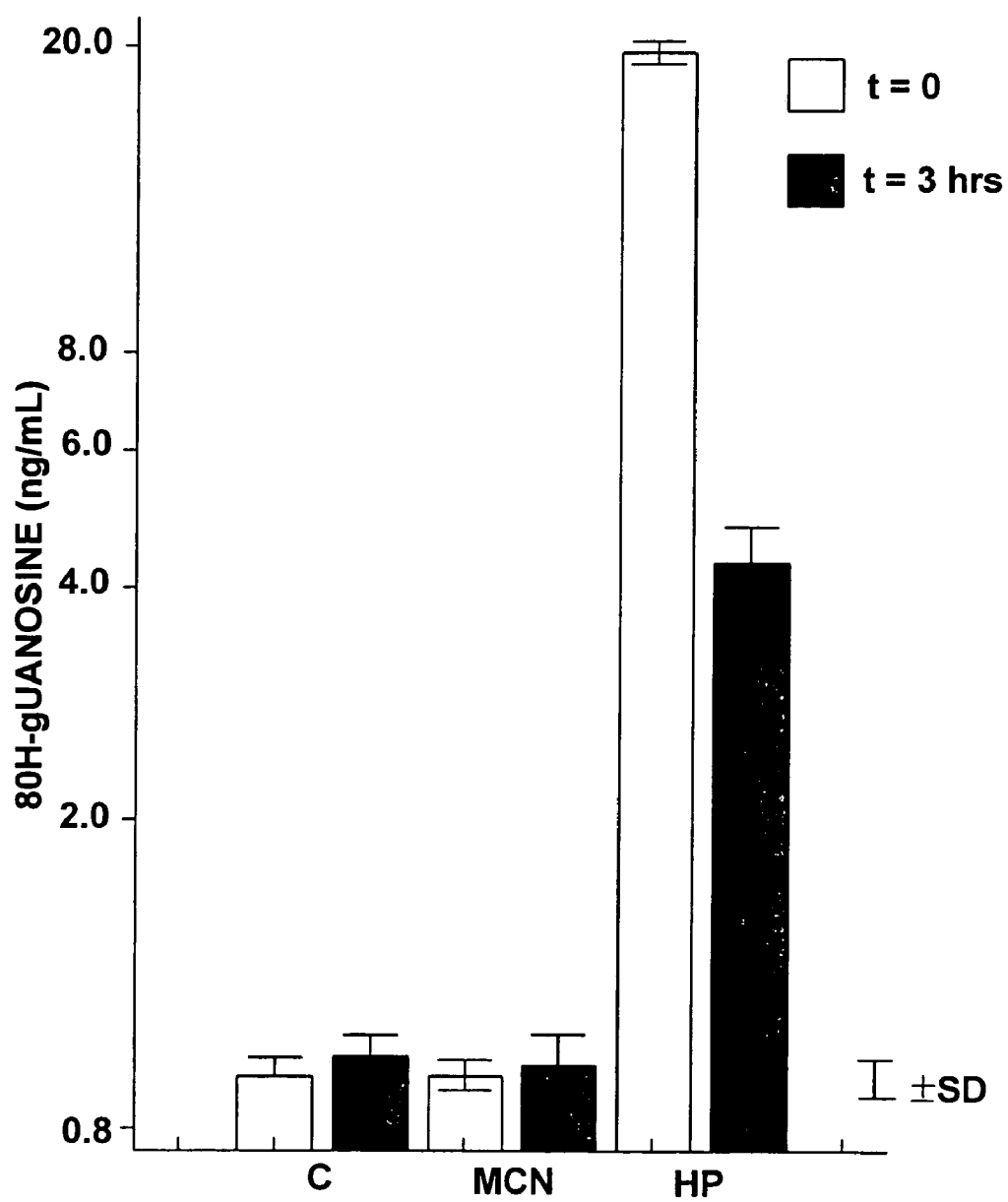
FIG. 9 is a graphical comparison of the levels of 8-hydroxy-2'-deoxiguanosine (8-OHdG) adducts in HDFs treated with an exemplary ORP water solution (MCN) versus 500 µM hydrogen peroxide (HP).

FIG. 9 shows the levels of 8-OHdG adducts present in DNA samples from HDFs after control treatments, ORP water solution treatments and HP-treatments for 30 minutes. DNA was extracted right after the exposure (T0, white bars) or three hours after the challenge period (T3, black bars). DNA was digested and the 8-OHdG adducts were measured by ELISA kit as per the manufacturer's instructions. Values are shown (ng/mL) as mean±SD (n=3). The exposure to ORP water solution for 30 minutes did not increase the formation of adducts in the treated cells in comparison to control cells after incubation for 30 minutes. In contrast, the treatment with highly diluted HP—down to sublethal and nontherapeutic HP concentrations (500 μM HP)—the treatment with 500 μM HP for 30 minutes increased the number of 8-OHdG adducts by about 25 fold relative to the control-treated or ORP water solution-treated cells.

The ORP water solution-treated cells were able to decrease the levels of 8-OHdG adducts if left in supplemented DMEM for 3 hours after exposure to the ORP water solution. Despite being allowed the same 3 hour recovery period, HP-treated cells still presented about 5 times more adducts than control-treated or ORP water solution treated cells. Altogether, these results demonstrate that acute exposure to the ORP water solution does not induce significant DNA oxidative damage. These results also indicate that the ORP water solution will not likely induce mutagenesis or carcinogenesis in vitro or in vivo.

Example 25

Figure 10A:
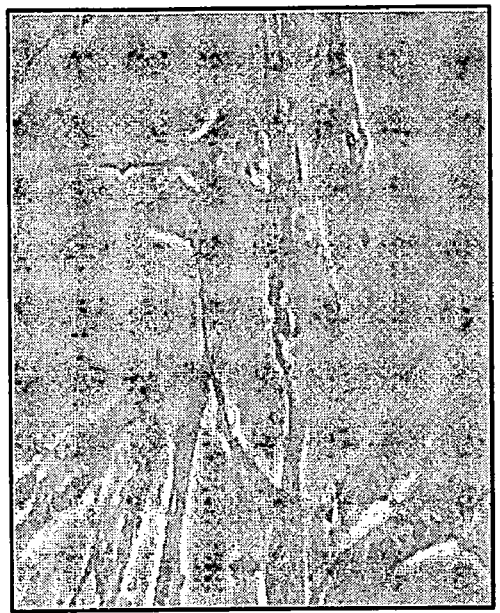
FIG. 10 illustrates the expression of a senescence associated with β-galactosidase in HDFs after chronic exposure to low concentrations of an exemplary ORP water solution (MCN) versus hydrogen peroxide (HP).
Figure 10A:
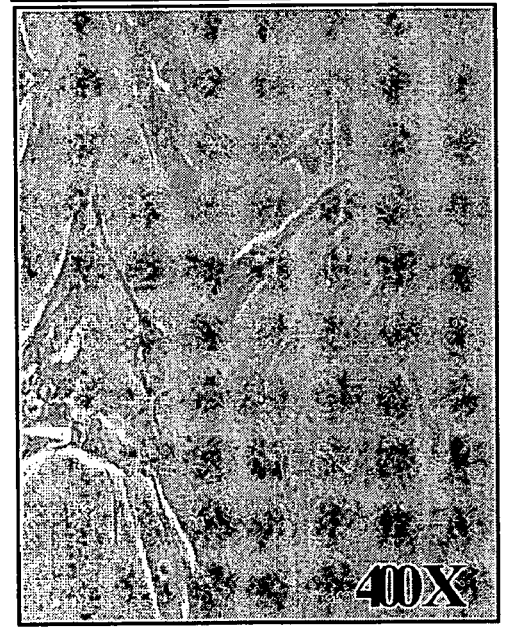
Figure 10B:
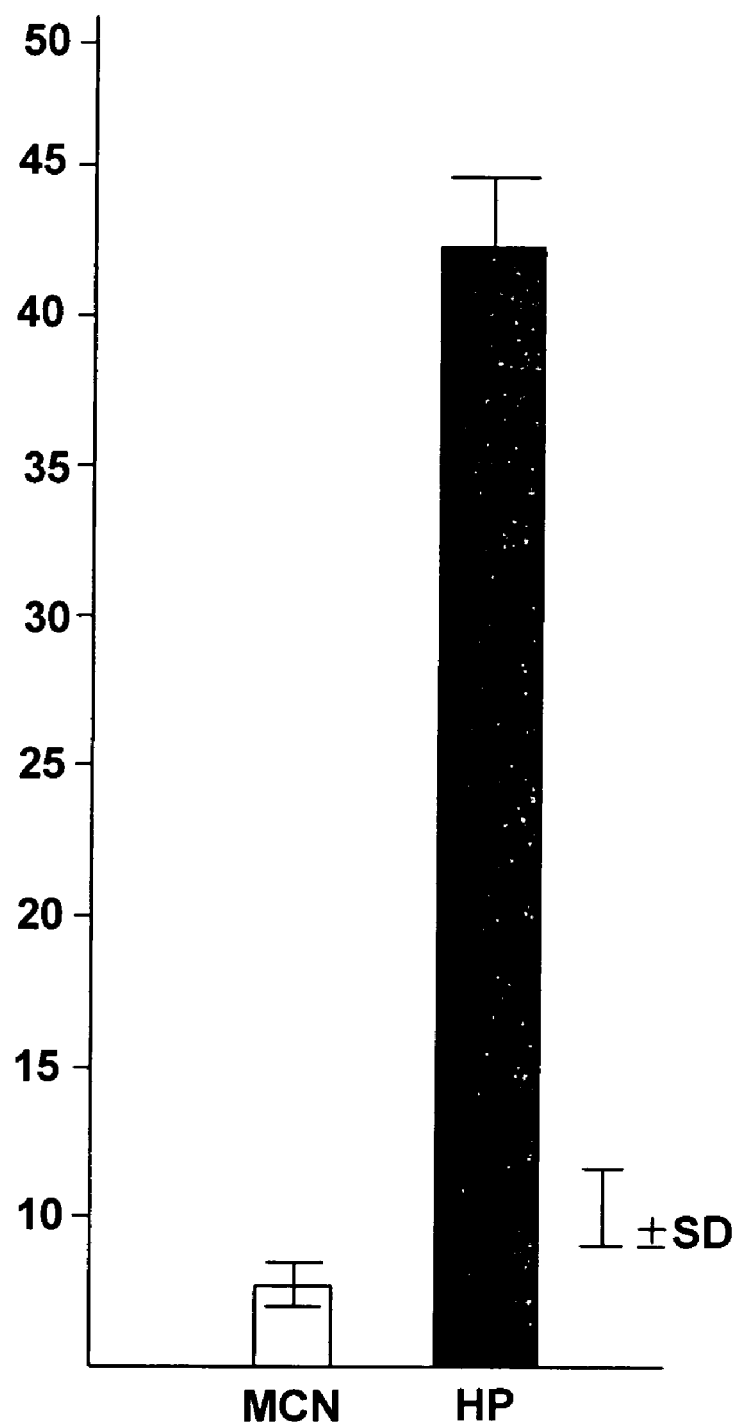

This example demonstrates the effects on HDFs of chronic exposure to low concentrations of an exemplary ORP water solution versus HP. It is known that chronic oxidative stress induces premature aging of cells. In order to mimic a prolonged oxidative stress, primary HDF cultures were chronically exposed to a low concentration of the ORP water solution (10%) or a non lethal-HP concentration (5 μM) during 20 population doublings. The expression and activity of the SA-β-galactosidase enzyme has previously been associated with the senescence process in vivo and in vitro. In this example the expression of the SA-β-galactosidase enzyme was analyzed after one month of continuous exposure of HDF to the ORP water solution or HP. The results are depicted in FIG. 10. The expression of the enzyme SA-p-galactosidase was analyzed by counting the number of blue cells in 20 microscopic fields. (For an example staining pattern, see Panel A.) Panel B shows that only HP treatment accelerated the aging of cells as indicated by the number of cells over-expressing SA-β-galactosidase (n=3). Chronic treatment with a low dose of HP increased the SA-β-Gal expression in 86% of cells while the treatment with the ORP water solution did not induce the overexpression of this protein. It can be concluded from this example that ORP water solution is not an inducer of premature cellular aging.

Example 26

This example demonstrates the results of a toxicity study using an exemplary ORP water solution.

An acute systemic toxicity study was performed in mice to determine the potential systemic toxicity of Microcyn 60, an exemplary ORP water solution. A single dose (50 mL/kg) of Microcyn 60 was injected intraperitoneally in five mice. Five control mice were injected with a single dose (50 mL/kg) of saline (0.9% sodium chloride). All animals were observed for mortality and adverse reactions immediately following the injection, at 4 hours after injection, and then once daily for 7 days. All animals were also weighed prior to the injection and again on Day 7. There was no mortality during the study. All animals appeared clinically normal throughout the study. All animals gained weight. The estimated Microcyn 60 acute intraperitoneal LD50 from this study is greater than 50 mL/kg. This example demonstrates that Microcyn 60 lacks significant toxicity and should be safe for therapeutic use accordance with the invention.

Example 27

This example illustrates a study conducted to determine the potential cytogenetic toxicity of an exemplary ORP water solution.

A micronucleus test was performed using an exemplary ORP water solution (Microcyn 10%) to evaluate the mutagenic potential of intraperitoneal injection of an ORP water solution into mice. The mammalian in vivo micronucleus test is used for the identification of substances which cause damage to chromosomes or the mitotic apparatus of murine polychromatic erythrocytes. This damage results in the formation of "micronuclei," intracellular structures containing lagging chromosome fragments or isolated whole chromosomes. The ORP water solution study included 3 groups of 10 mice each (5 males/5 females): a test group, dosed with the ORP water solution; a negative control group, dosed with a 0.9% NaCl solution; and a positive control group, dosed with a mutagenic cyclophosphamide solution. The test and the negative control groups received an intraperitoneal injection (12.5 ml/kg) of the ORP water solution or 0.9% NaCl solution, respectively, for two consecutive days (days 1 and 2). The positive control mice received a single intraperitoneal injection of cyclophosphamide (8 mg/mL, 12.5 ml/kg) on day 2. All mice were observed immediately after injection for any adverse reactions. All animals appeared clinically normal throughout the study and no sign of toxicity was noted in any group. On day 3, all mice were weighed and terminated.

The femurs were excised from the terminated mice, the bone marrow was extracted, and duplicate smear preparations were performed for each mouse. The bone marrow slides for each animal were read at 40× magnification. The ratio of polychromatic erythrocytes (PCE) to normochromatic erythrocytes (NCE), an index of bone marrow toxicity, was determined for each mouse by counting a total of at least 200 erythrocytes. Then a minimum of 2000 scoreable PCE per mouse were evaluated for the incidence of micronucleated polychromatic erythrocytes. Statistical analysis of the data were done using the Mann and Whitney test (at 5% risk threshold) from a statistical software package (Statview 5.0, SAS Institute Inc., USA).

The positive control mice had statistically significant lower PCE/NCE ratios when compared to their respective negative controls (males: 0.77 vs. 0.90 and females: 0.73 vs. 1.02), showing the toxicity of the cyclophosphamide on treated bone marrow. However, there was no statistically significant difference between the PCE/NCE ratios for the ORP water solution-treated mice and negative controls. Similarly, positive control mice had a statistically significant higher number of polychromatic erythrocytes bearing micronuclei as compared to both the ORP water solution-treated mice (males: 11.0 vs. 1.4/females: 12.6 vs. 0.8) and the negative controls (males: 11.0 vs. 0.6/females: 12.6 vs. 1.0). There was no statistically significant difference between the number of polychromatic erythrocytes bearing micronculei in ORP water solution-treated and negative control mice.

This example demonstrates that Microcyn 10% did not induce toxicity or mutagenic effects after intraperitoneal injections into mice.

Example 28

This study demonstrates the lack of toxicity of an exemplary ORP water solution, Dermacyn.

This study was done in accordance with ISO 10993-5:1999 standard to determine the potential of an exemplary ORP water solution, Dermacyn, to cause cytotoxicity. A filter disc with 0.1 mL of Dermacyn was placed onto an agarose surface, directly overlaying a monolayer of mouse fibroblast cells (L-929). The prepared samples were observed for cytotoxic damage after 24 hours of incubation at 37° C. in the presence of 5% CO2. Observations were compared to positive and negative control samples. The Dermacyn containing samples did not reveal any evidence of cell lysis or toxicity, while positive and negative control performed as anticipated.

Based on this study Dermacyn was concluded not to generate cytotoxic effects on murine fibroblasts.

Example 29

This study was conducted with 16 rats to evaluate the local tolerability of an exemplary ORP water solution, Dermacyn, and its effects on the histopathology of wound beds in a model of full-thickness dermal wound healing. Wounds were made on both sides of the subject rat. During the healing process skin sections were taken on either the left or the right sides (e.g., Dermacyn-treated and saline-treated, respectively).

Masson's trichrome-stained sections and Collagen Type II stained sections of the Dermacyn and saline-treated surgical wound sites were evaluated by a board-certified veterinary pathologist. The sections were assessed for the amount of Collogen Type 2 expression as a manifestiation of connective tissue proliferation, fibroblast morphology and collagen formation, presence of neoepidermis in cross section, inflammation and extent of dermal ulceration.

The findings indicate that Dermacyn was well tolerated in rats. There were no treatment-related histopathologic lesions in the skin sections from either sides' wounds (Dermacyn-treated and saline-treated, respectively). There were no relevant histopathologic differences between the saline-treated and the Dermacyn-treated wound sites, indicating that the Dermacyn-treatement was well tolerated. There were no significant differences between Collagen Type 2 expression between the saline-treated and the Dermacyn-treated wound sites indicating that the Dermacyn does not have an adverse effect on fibroblasts or on collagen elaboration during wound healing.

Example 30

This example demonstrates the effectiveness of an exemplary ORP water solution (Mycrocyn) in inhibiting mast cell degranulation. Mast cells have been recognized as principal players in type I hypersensitivity disorders. Multiple clinical symptoms observed in atopic dermatitis, allergic rhinitis, and atopic asthma are produced by IgE-antigen stimulation of mast cells located in distinct affected tissues. The currently accepted view of the pathogenesis of atopic asthma is that allergens initiate the process by triggering IgE-bearing pulmonary mast cells (MCs) to release mediators such as histamine, leukotrienes, prostaglandins, kininis, platelet activating factor (PAF), etc. in the so-called early phase of the reaction. In turn, these mediators induce bronchoconstriction and enhance vascular permeability and mucus production.

Figure 11:
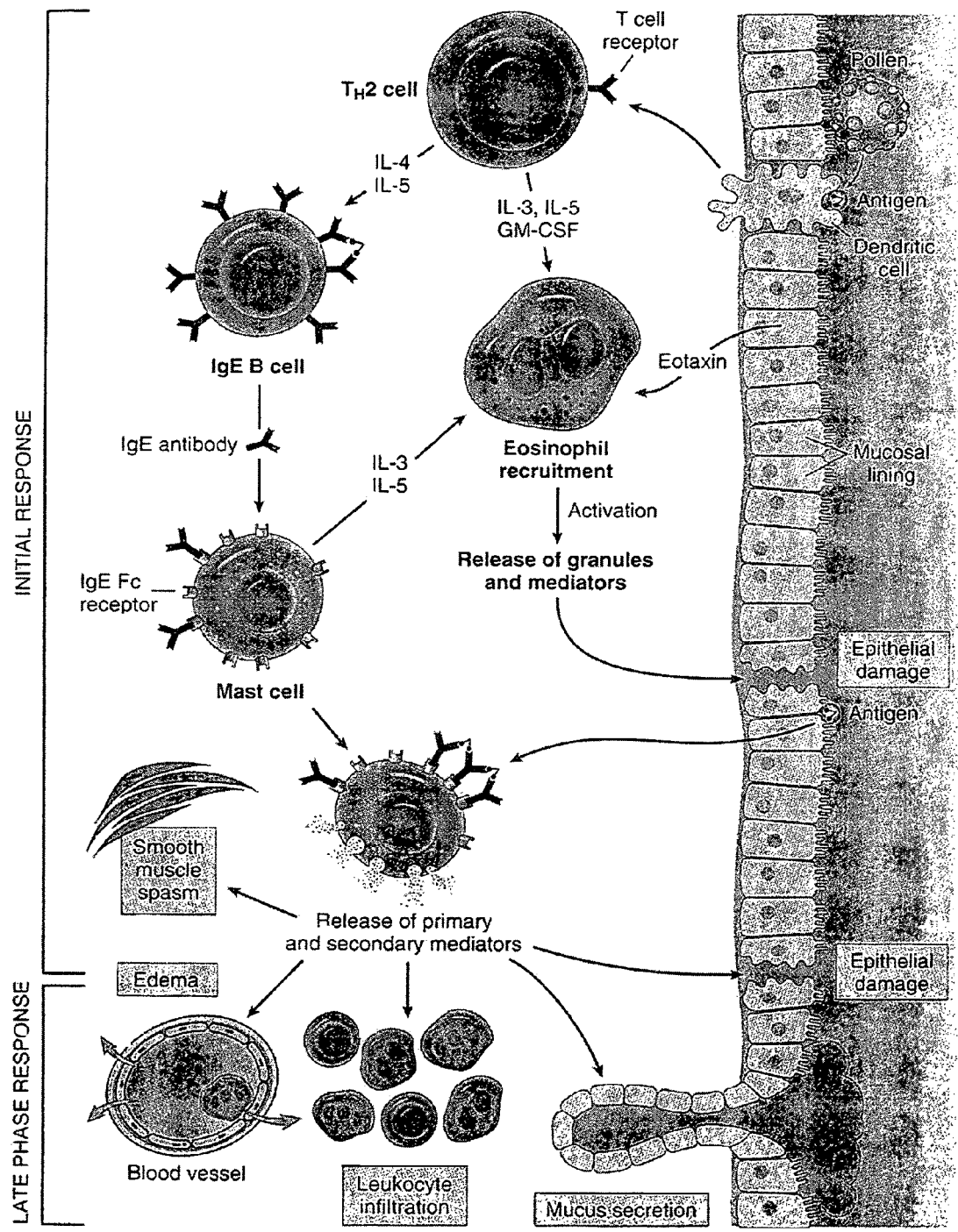
FIG. 11 depicts the biological events associated with mast cell activation.

According to this model, following mast cell activation, those cells secrete various pro-inflammatory cytokines, including tumor necrosis factor alpha (TNF-α), IL-4, IL-5 and IL-6, which participate in the local recruitment and activation of other inflammatory cells such as eosinophils, basophils, T lymphocytes, platelets and mononuclear phagocytes. These recruited cells, in turn, contribute to the development of an inflammatory response that may then become autonomous and aggravate the asthmatic symptoms. This late phase response constitutes a long term inflammation process which can induce plastic changes in surrounding tissues (see FIG. 11). Accordingly, MCs offer model for cytokine release by antigen-stimulated inflammatory/immune system cells.

Antigenic stimulation of mast cells occurs via the activation of the high affinity receptor for IgE (the FcεRI receptor), which is a multimeric protein that binds IgE and subsequently can be aggregated by the interaction of the receptor-bound IgE with a specific antigen. Its structure comprises four polypeptides, an IgE binding α chain, a β chain that serves to amplify its signaling capacity, and two disulfide-linked γ chains, which are the principal signal transducers via the encoded immunoreceptor tyrosine-based (ITAM) activation motif. Signaling pathways activated by the cross-linking of this receptor have been characterized using bone marrow-derived mast cells (BMMC), the rat leukemia cell line RBL 2H3, mouse and rat peritoneal mast cells, and other mast cell lines, such as MC-9, In all of them, the presence of antigen bound to IgE causes mast cell degranulation, calcium mobilization, cytoskeletal re-arrangements and activation of different transcription factors (NFAT, NFκB, AP-1, PU.1, SP1, Ets, etc.) which activate cytokine gene transcription that culminate with cytokine production.

Figure 12:
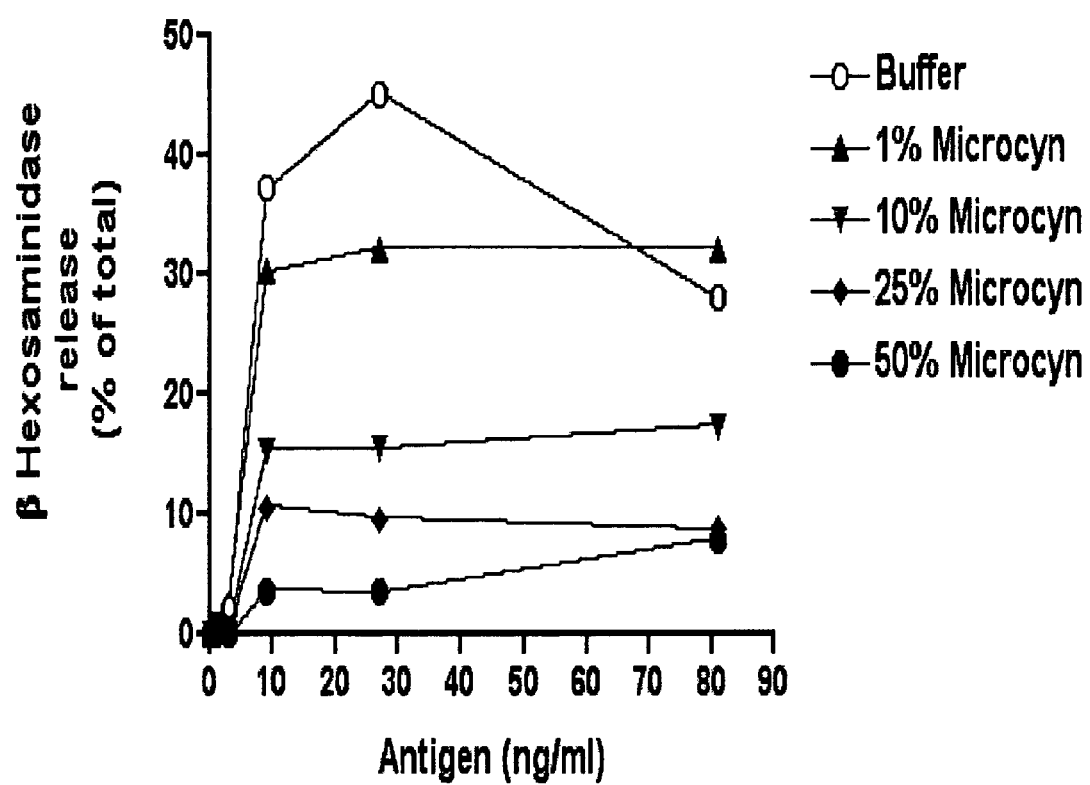
FIG. 12 illustrates the effect on degranulation of antigen-activated mast cells treated with various concentrations of an exemplary ORP water solution (MCN).

Mature murine BMMC were loaded with a monoclonal anti-Dinitrophenol IgE (300 ng/million cell) during 4 hours at 37° C. Culture media was removed and cells were resuspended in physiological buffer (Tyrode's Buffer/BSA). Cells were then treated 15 minutes at 37° C. with distinct concentrations of the ORP water solution (Microcyn). Buffer was removed and cells were resuspended in fresh Tyrode's/BSA and stimulated with different concentrations of antigen (Human Albumin coupled to Dinitrophenol) during a 30 minute incubation at 37° C. Degranulation was measured by β-hexosamimidase activity determination in supernatants and pellets of the stimulated cells, using a colorimetric reaction based on the capacity of this enzyme to hydrolize distinct carbohydrates. (β-hexosamimidase has been shown to be located in the same granules that contain histamine in mast cells.) The results (FIG. 12) demonstrate that degranulation is significantly reduced with increasing concentrations of the ORP water solution.

Figure 13:
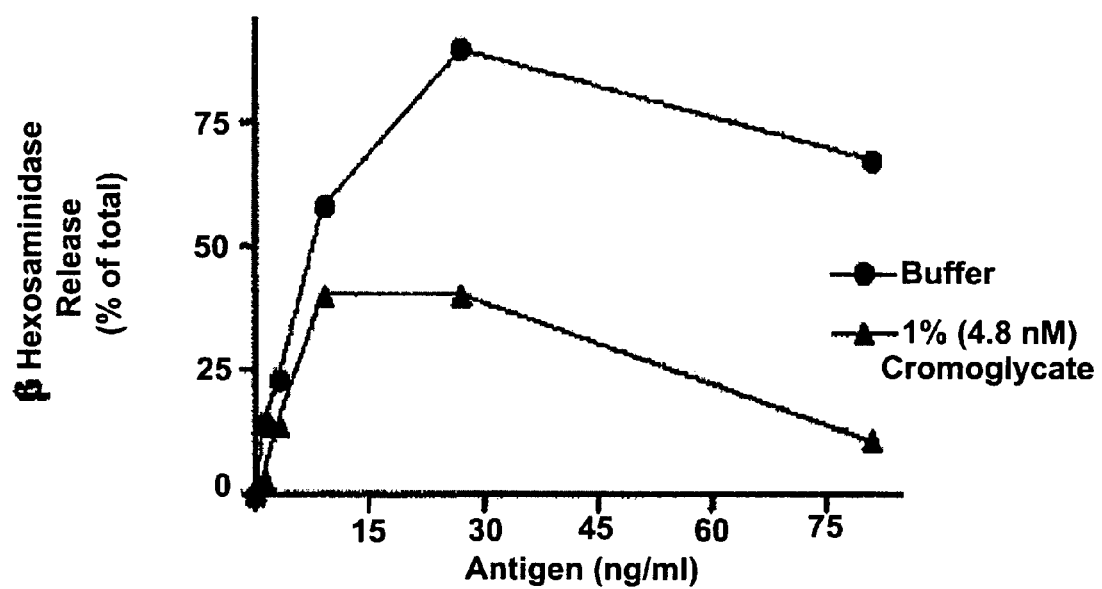
FIG. 13 comparatively illustrates the effect of an exemplary ORP water solution (MCN) on degranulation of antigen-activated mast cells treated with cromoglycate.

Surprisingly, the inhibitory effect of the ORP water solution (Microcyn) on mast cell degranulation is at least similar to that observed with the clinically effective "mast cell stabilizer" and established anti-allergic compound sodium cromoglycate (Intel™) (FIG. 13). Degranulation was again measured by β-hexosamimidase enzymatic activity in the pellet and supernatant of stimulated cells, using a colorimetric reaction based on the capacity of this enzyme to hydrolize distinct carbohydrates. Cells loaded with anti-DNP monoclonal IgE were stimulated with or without a 15 minute pre-incubation with sodium cromoglycate (Intel™). Cromoglycate was no more effective than the ORP water solution in reducing degranulations (Compare FIG. 12 with FIG. 13; both achieving at least about 50% reduction in degranulation.)

Example 31

This example demonstrates the inhibitory activity of an exemplary ORP water solution on mast cell activation by a calcium ionophore.

Mast cells can be stimulated via the activation of calcium fluxes induced by a calcium ionophore. Signaling pathways activated by calcium ionophores have been characterized using bone marrow-derived mast cells (BMMC), the rat leukemia cell line RBL 2H3, mouse and rat peritoneal mast cells, and other mast cell lines, such as MC-9. In all of these systems the calcium mobilization causes mast cell degranulation (e.g. histamine release), cytoskeletal re-arrangements, and activation of different transcription factors (e.g., NFAT, NFκB, AP-1, PU.1, SP1, Ets.) which activate cytokine gene transcription that culminate with cytokine production and secretion.

Figure 14:
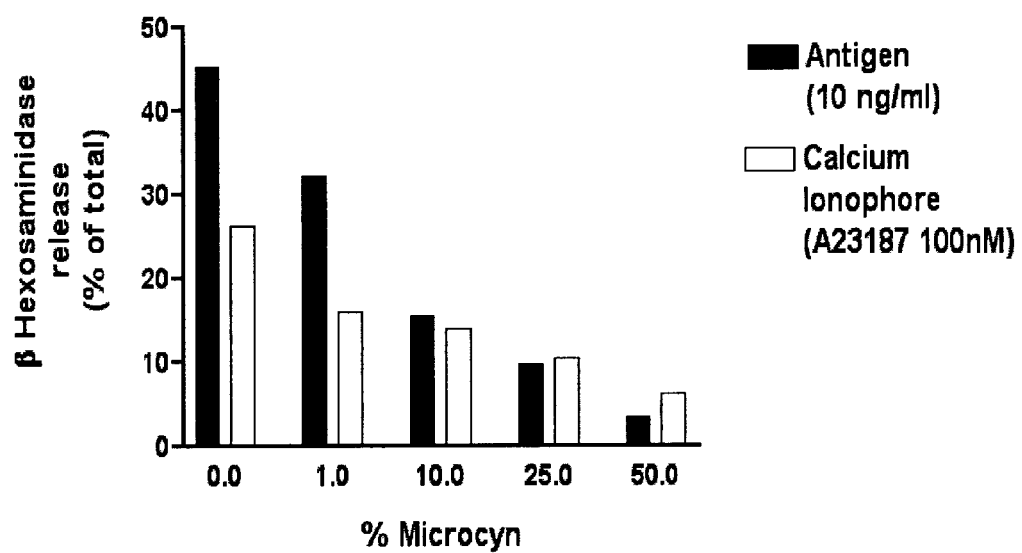
FIG. 14 illustrates the effect on degranulation of antigen-activated and calcium ionophore (A23187)-activated mast cells treated with various concentrations of an exemplary ORP water solution (MCN).

Mature murine bone marrow-derived mast cells (BMMC) were loaded with a monoclonal anti-Dinitrophenol IgE (300 ng/million cell) during 4 hours at 37° C. Culture media was removed and cells were resuspended in physiological buffer (Tyrode's Buffer/BSA). Cells were then treated for 15 minutes at 37° C. with distinct concentrations of the ORP water solution (Microcyn). Buffer was removed and cells were resuspended in fresh Tyrode's/BSA and stimulated with calcium ionophore (100 mM A23187) during a 30 minute incubation at 37° C. Degranulation was measured by β-hexosamimidase activity determination in supernatants and pellets of the stimulated cells, using a colorimetric reaction based on the capacity of this enzyme to hydrolyze distinct carbohydrates. (β-hexosamimidase has been shown to be located in the same granules that contain histamine in mast cells.) The results (FIG. 14) demonstrate that degranulation is significantly reduced with increasing concentrations of the ORP water solution.

These results suggest that ORP water solution is a non-specific inhibitor of histamine release. Thus, ORP water solution—even at different concentrations—will inhibit the degranulation of mast cells independently of the stimulus (e.g. antigen or ionophore). While not desiring to be bound by any theory, ORP water solution probably modifies the secretory pathway system at the level of the plasma membrane and/or cytoskeleton. Because the mechanism of action of ORP water solution is believed to be non-specific, it is believed that ORP water solution can have broad potential clinical applications.

Example 32

This example demonstrates the effect of an exemplary ORP water solution on the activation of mast cell cytokine gene transcription.

Figure 15A:
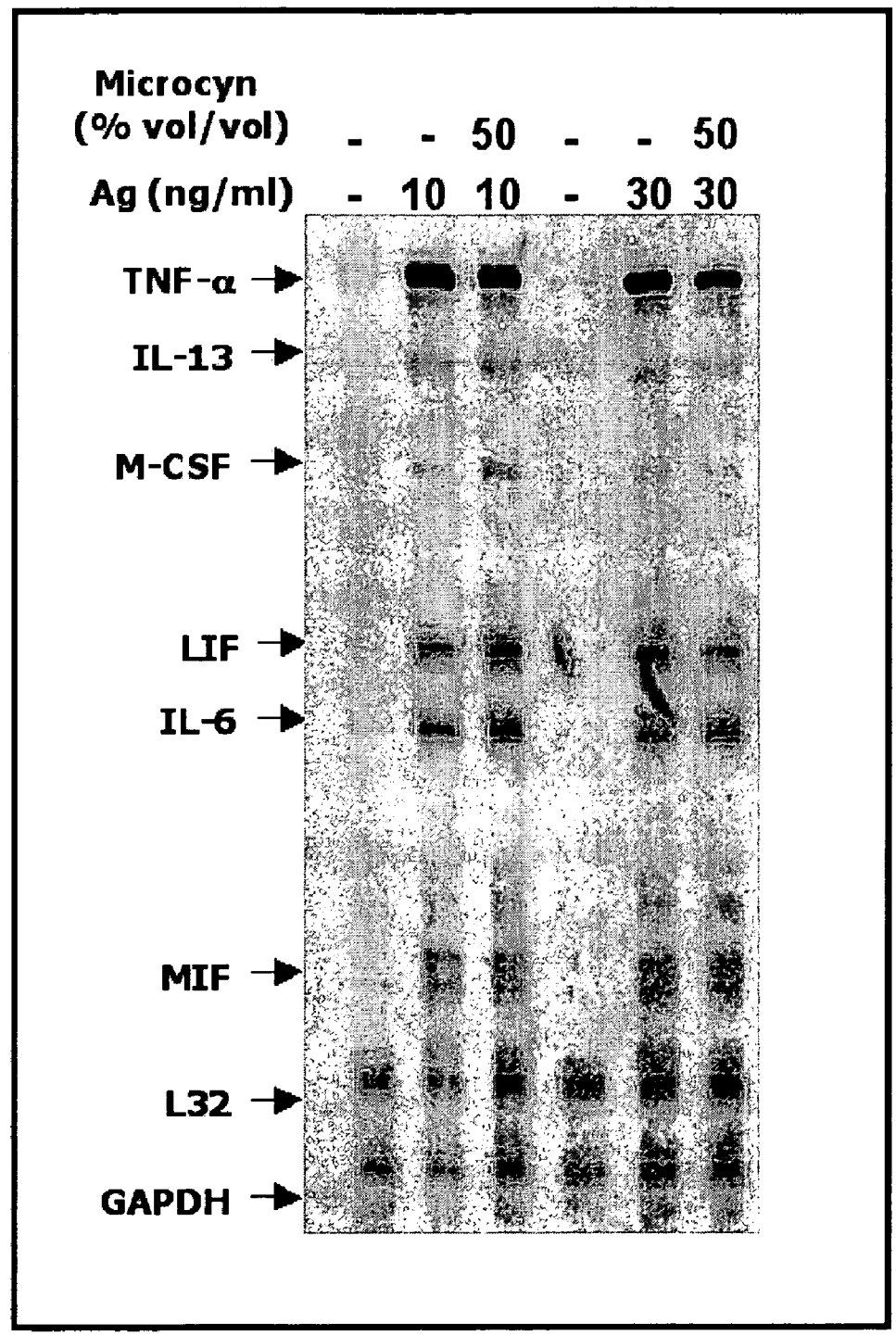
FIG. 15A-15B are RNAse protection assays illustrating cytokine mRNA levels after antigen challenge in control versus ORP water solution-treated mast cells.
Figure 15B:
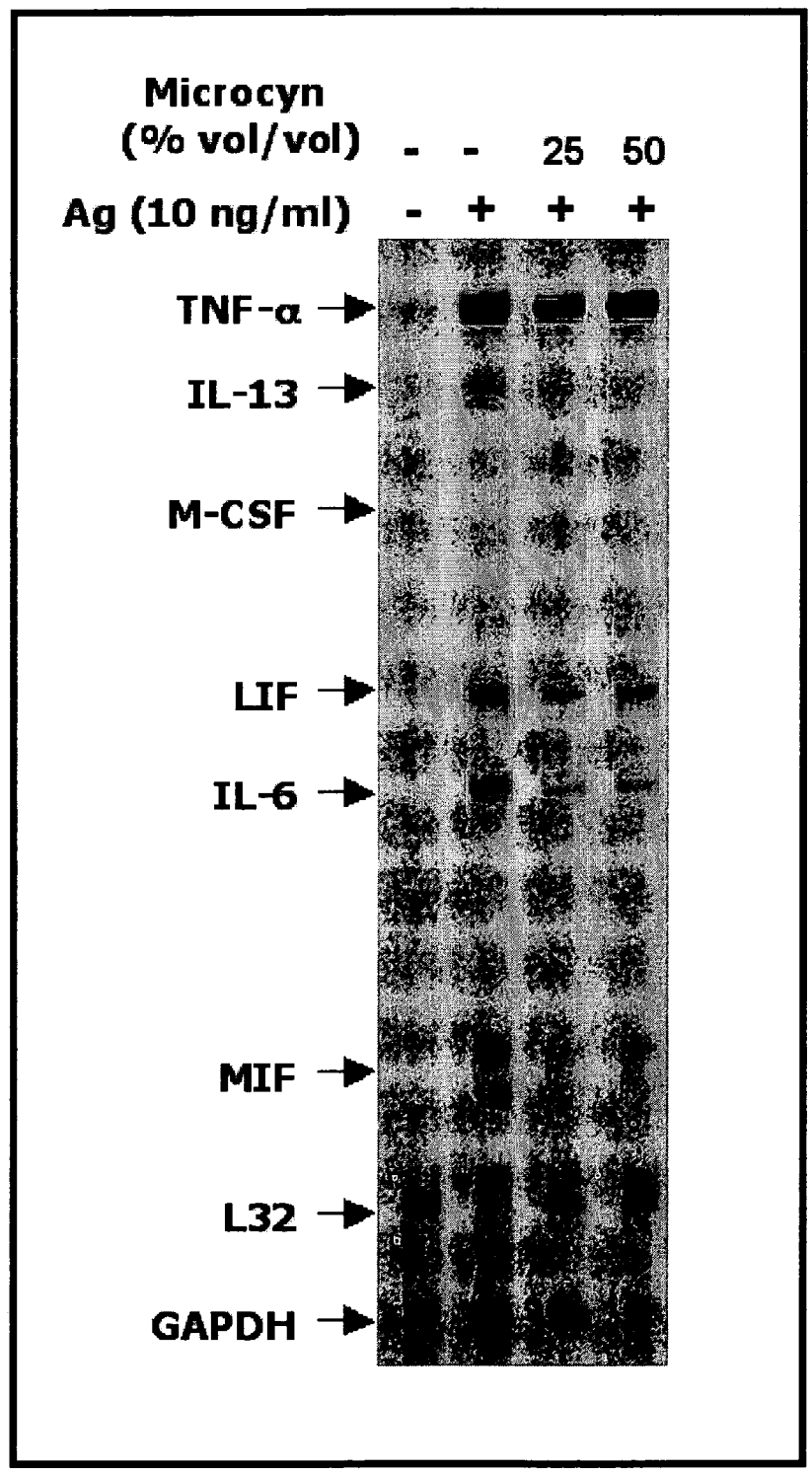

FIGS. 15A and 15B are RNAase protection assays from mast cells treated with ORP water solution at different concentrations for 15 minutes and further stimulated by antigen as described in Example 30. After stimulation, mRNA was extracted using affinity chromatography columns (RNAeasy kit, Qiagene) and the RNAse Protection Assay was performed using standard kit conditions (Clontech, Becton & Dickinson) in order to detect mRNA production of distinct cytokines after antigen challenge. The cytokines included TNF-α, LIF, IL13, M-CSF, IL6, MIF and L32.

FIGS. 15A and 15B show that the ORP solution water (Microcyn) did not modify cytokine mRNA levels after antigen challenge in mast cells irrespective of the concentrations of ORP water solution or antigen used for the experiment.

In this study, the level of transcripts (i.e., the RNA content of stimulated mast cells) of proinflammatory genes was not changed in ORP water solution-treated mast cells after being stimulated with various concentrations of antigen. Thus, the ORP water solution inhibited the secretory pathway of these cytokines without affecting their transcription.

Example 33

This example demonstrates the inhibitory activity of an exemplary ORP water solution on mast cell secretion of TNF-α.

Mast cells were treated with different concentrations of ORP water solution for 15 minutes and further stimulated by antigen as described in Example 30. Thereafter, the tissue culture medium was replaced and samples of the fresh medium were collected at various periods of time (2-8 hours) for measuring TNF-α levels. Samples were frozen and further analyzed with a commercial ELISA kit (Biosource) according to the manufacturer's instructions.

Figure 16:
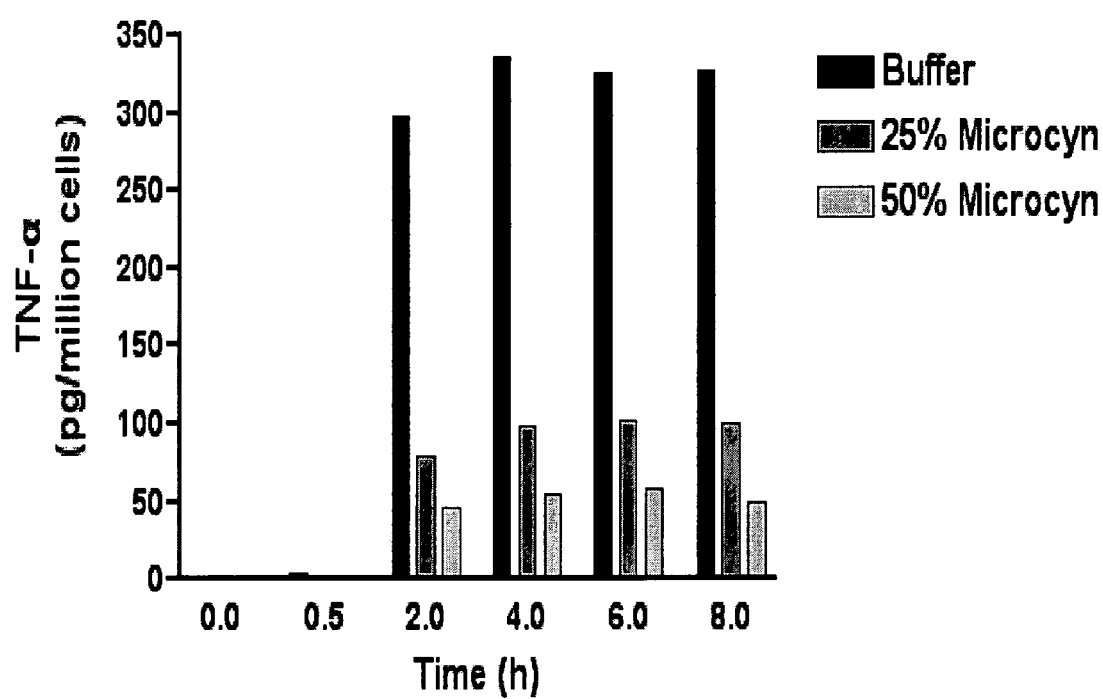
FIG. 16 is a graphical comparison of TNF-α secretion by antigen-activated mast cells treated with various concentrations of an exemplary ORP water solution (MCN).

FIG. 16 shows that the level of secreted TNF-α to the medium from ORP water solution-treated cells after antigen stimulation is significantly decreased in comparison to the untreated cells.

Thus, the ORP water solution inhibited TNF-α secretion of antigen-stimulated mast cells. These results are in agreement with clinical observations that the use of ORP water solutions can decrease the inflammatory reaction in various wounds after surgical procedures.

Example 34

This example demonstrates the inhibitory activity of an exemplary ORP water solution on mast cell secretion of MIP 1-α.

Mast cells were treated with different concentrations of an exemplary ORP water solution (Microcyn) for 15 minutes and further stimulated by antigen as described in Example 30. Thereafter, the tissue culture medium was replaced and samples of the fresh medium were collected at various periods of time (2-8 hours) for measuring MIP 1-α levels. Samples were frozen and further analyzed with a commercial ELISA kit (Biosource) according to the manufacturer's instructions.

Figure 17:
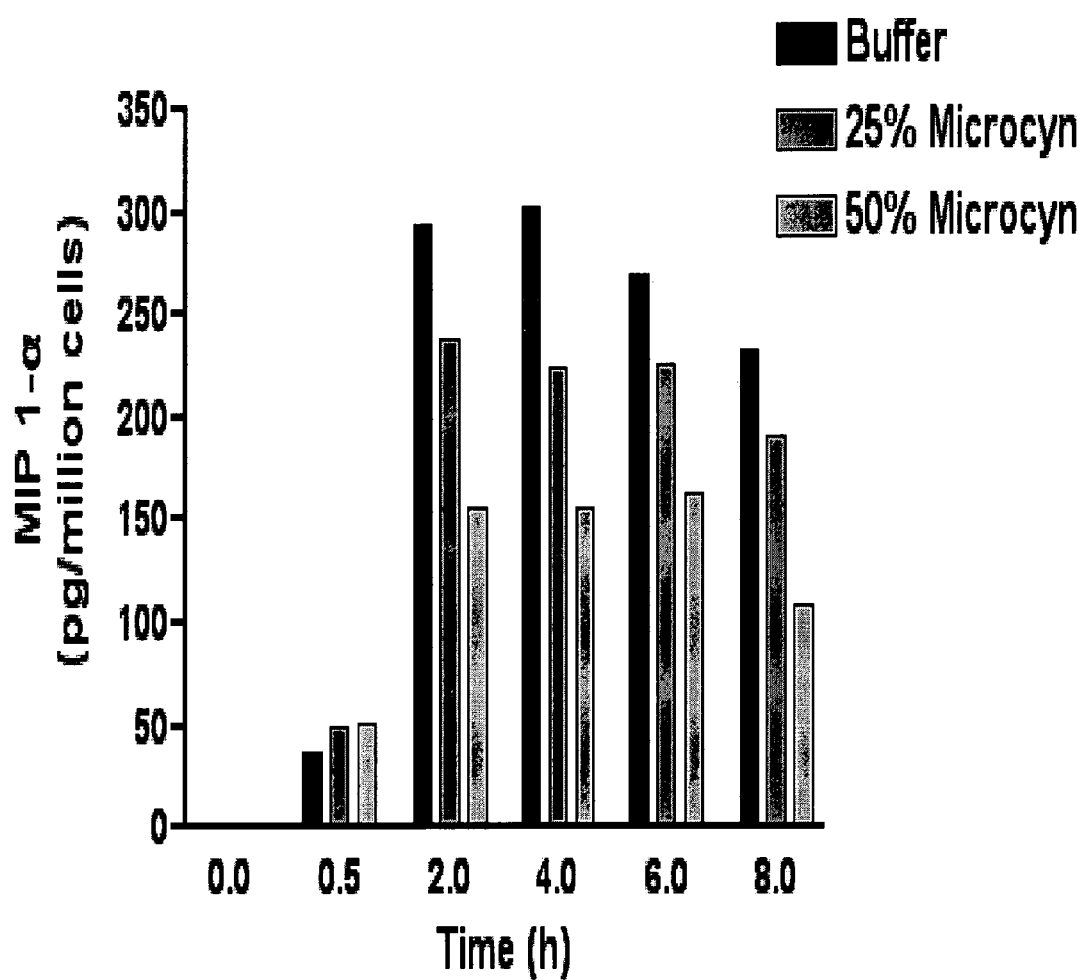
FIG. 17 is a graphical comparison of MIP 1-α secretion by antigen-activated mast cells treated with various concentrations of an exemplary ORP water solution (MCN).

FIG. 17 shows that the level of secreted MIP 1-α to the medium from ORP water solution-treated cells after antigen stimulation was significantly decreased in comparison to the untreated cells.

Thus, the ORP water solution inhibited MIP 1-α secretion of antigen-stimulated mast cells. These results are in agreement with clinical observations that the use of ORP water solutions can decrease the inflammatory reaction in various wounds after surgical procedures.

Examples 30-33 and this example further demonstrate that the ORP water solution is able to inhibit early and late phase allergic responses initiated by IgE receptor crosslinking.

Example 35

This example demonstrates the antimicrobial activity, reduction of hospital stay and improved cosmetic results of an exemplary ORP water solution, Microcyn, on first, second, and third degree—pediatric burns.

The study was designed on the basis of the clinical results with the ORP water solution and knowing the safety and efficacy of ORP water solution to eliminate *Pseudomonas* in burns in an animal model.

The primary end point of this pilot trial was the local control of the infection.

Figure 18:
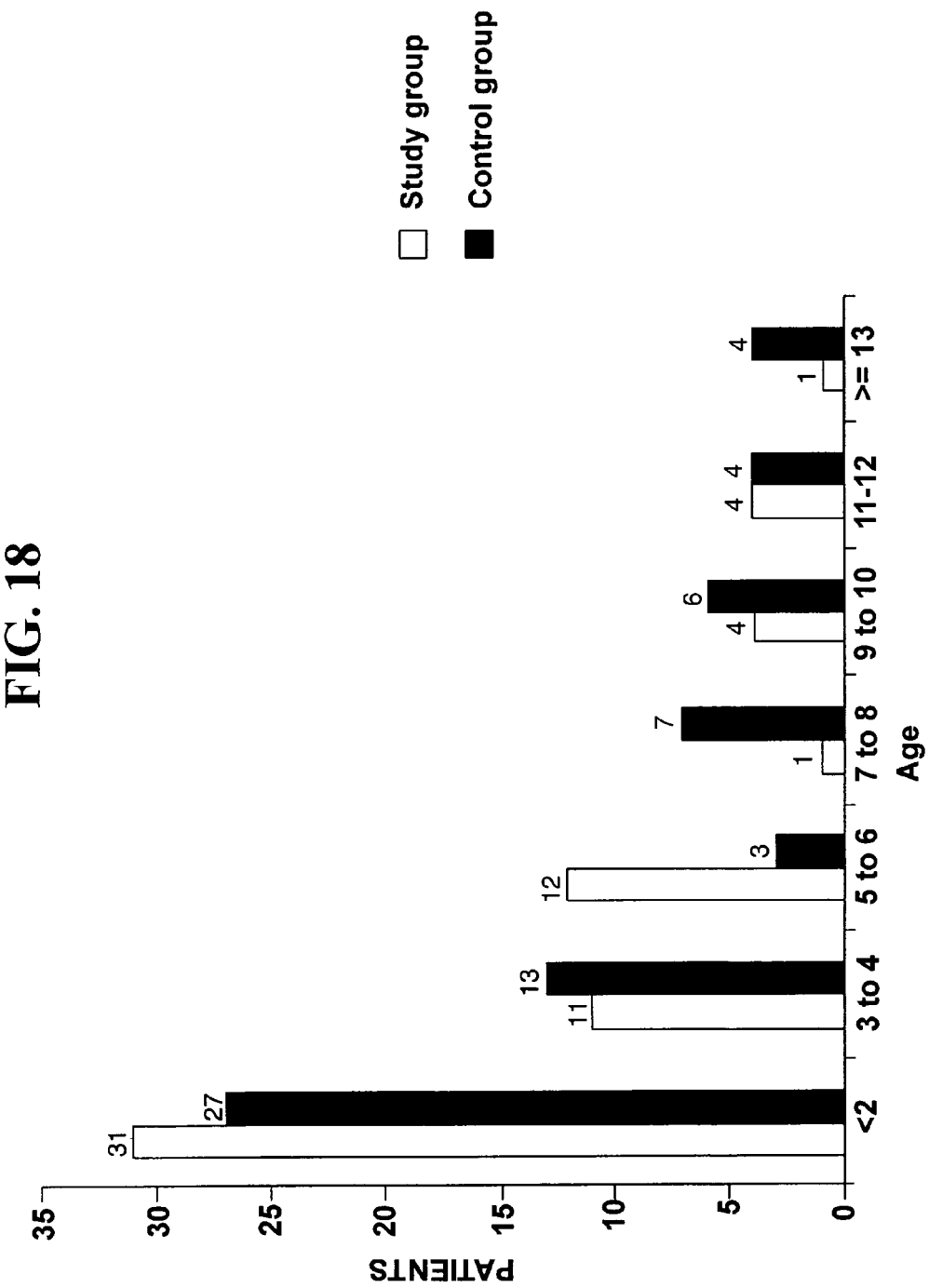
FIG. 18 is a graphical representation of the age distribution in pediatric burn patients treated with an exemplary ORP water solution (Study group) or standard therapy (Control group).

Sixty four consecutive patients admitted to the Hospital Civil de Guadalajara in Mexico from March 2004 to March 2005 with a diagnosis of superficial-partial, deep-partial and full-thickness thermal injuries to the skin were entered the study group (i.e. ORP water solution) (35 males, 29 females). Retrospective analysis of paired-cases presenting similar burns at that Institution during 2003 was undertaken for the control group (40 males, 24 females). The control group had been treated with silver solution/ointments. The age distribution of the two groups was similar (FIG. 18). The causes of the burns were also similar in the two groups and included fire, boiling water, and electricity. The extent of the burns is show in Table 23.

TABLE 23

Extension of the Burn

| EXTENSION OF | NO. OF PATIENTS | |
|---|---|---|
| THE BURN | Study Group | Control Group |
| 0 to 9% | 10 | 20 |
| 10 to 19% | 27 | 28 |
| 20 to 29% | 11 | 6 |
| 30 to 39% | 8 | 4 |
| 40 to 49% | 4 | 3 |
| 50 to 59% | 1 | 0 |
| 60 to 69% | 3 | 3 |

At entry, all patients in the study group underwent surgical debridement and high pressure-irrigation of ORP water solution using the Jetox system. Only third degree, full-thickness burns with profuse secretions were covered with gauzes soaked in ORP water solution. Most of the patients, however, were treated in an open modality. In doing so, the majority of the children could take a bath every day and receive ORP water solution t.i.d. (in spray form) without the use of gels or dressings on top of the lesions. Tissue biopsies were obtained from the wound bed for qualitative bacteriology at entry and after one week of treatment. Skin grafts were used as necessary in full thickness burns. Patients in the control group were treated in a similar way but using silver solutions instead of ORP water solution. As part of the hospital protocol, patients were kept on antibiotics in the case of a positive culture for *Staph aureus* or if they were transferred from another Institution.

In this trial, only 6 patients received antibiotics in the ORP water solution group versus 46 in the control group (Table 24). Despite this, positive cultures were obtained in 6 and 22 patients after therapy, respectively (See Table 25). However none of the patients in the ORP water solution group showed signs of overt infections neither during their stay at the hospital nor after discharge.

TABLE 24

Antibiotic Usage

| Group | Number of patients on antibiotics | Number of patients with antibiotics and positive culture | Average stay of patients on antibiotics. |
|---|---|---|---|
| Control group | 46 | 22 | 28.6 |
| Study group | 6 | 6 | 17.5 |

TABLE 25

Microbiology Results

| CONTROL GROUP (n = 22) | % | STUDY GROUP (n = 6) | % |
|---|---|---|---|
| Staph. aureus | 56.0 | Staph. aureus | 57.1 |
| Pseudomonas aeruginosa | 19.0 | Enterobacter cloacae | 28.6 |
| Candida albicans | 12.0 | Staph haemolyticus | 14.2 |
| Enterobacter cloacae | 8.0 | | |
| Klebsiella sp. | 5.0 | | |
| TOTAL | 100.0 | TOTAL | 100.0 |

ORP water solution-treated children also appeared to complain of less pain.

The hospital stay was reduced in almost 50% in the ORP water solution group versus the control group (14.8 days vs 28.6 days, respectively). Hospital stay was also reduced in ORP water solution-treated patients versus control patients when first, second, and third degree burns were analyzed separately (Table 26.)

TABLE 26

Hospital Stay by Burn Severity.

| BURN GRADE | STUDY GROUP | AVG. HOSPITAL DAYS | CONTROL GROUP | AVG. HOSPITAL DAYS |
|---|---|---|---|---|
| 1° | 6 | 4.6 | 45 | 19.2 |
| 2° | 44 | 10.6 | 9 | 26.9 |
| 3° | 14 | 29.5 | 10 | 39.8 |

However, analysis of the results based on the size of the burn failed to demonstrate which therapy was superior (FIG. 19.)

Since the daily hospital cost at this facility is around $1,800 per patient, ORP water solution saved an average of $24,660 per patient to the hospital. It was also suggested that third degree burns up to 10 cm in diameter healed completely without requiring skin grafts, with better cosmetic results and less chelation in ORP water treated patients than using previous standard burn treatment.

Thus, an exemplary ORP water solution reduces the microbial load and length of hospital stay of patients with partial and full-thickness thermal injuries. Other benefits such as reduction of pain and improve scarring were suggested by this study.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating an infected diabetic foot ulcer in a patient comprising administering an oxidative reductive potential (ORP) water solution to the patient in an amount effective to treat the skin ulcer, wherein the solution has a pH of about 6.4 to about 7.8 and is stable for at least two months, wherein the ORP water solution comprises anode water and cathode water, and wherein the ORP water solution comprises free chlorine species at a level of from about 30 ppm to about 100 ppm, and wherein the free chlorine species comprises at least one of: hypochlorous acid present in an amount of from about 15 μm to about 35 μm and sodium hypochlorite present in an amount from about 25 μm to about 50 ppm.

2. The method of claim 1, wherein the solution is stable for at least one year.

3. The method of claim 1, wherein the pH is from about 7.4 to about 7.6.

4. The method of claim 1, wherein the cathode water is present in an amount of from about 10% by volume to about 50% by volume of the solution.

5. The method of claim 1, wherein the cathode water is present in an amount of from about 20% by volume to about 40% by volume of the solution.

6. The method of claim 1, wherein the anode water is present in an amount of from about 50% by volume to about 90% by volume of the solution.

7. The method of claim 1, wherein the solution comprises hypochlorous acid in an amount of from about 15 ppm to about 35 ppm and sodium hypochlorite in an amount of from about 25 ppm to about 50 ppm.

8. The method of claim 1, wherein the solution is administered to the patient by washing or irrigating the ulcer with the solution.

9. The method of claim 1, wherein the solution is administered to the patient by soaking the ulcer in the solution.

10. The method of claim 9, wherein the ulcer is soaked in the solution for at least one minute.

11. The method of claim 9, wherein the ulcer is soaked in the solution for at least two minutes.

12. The method of claim 1, wherein the solution is administered to the patient by dressing the ulcer with a wound dressing saturated with the solution.

13. The method of claim 1, further comprising debriding the ulcer.

14. A method of reducing the microbial load of an infected diabetic foot ulcer in a patient comprising treating the ulcer in accordance with the method of claim 1.

15. A method of decreasing the recurrence rate of an infected diabetic foot ulcer in a patient comprising treating the ulcer in accordance with the method of claim 1.

16. A method of decreasing the likelihood of dehiscence of an infected diabetic foot ulcer in a patient comprising treating the ulcer in accordance with the method of claim 1.

17. A method of decreasing the likelihood of amputation resulting from an infected diabetic foot ulcer in a patient comprising treating the ulcer in accordance with the method of claim 1.

18. A method of decreasing the likelihood of systemic inflammatory response syndrome resulting from an infected diabetic foot ulcer in a patient comprising treating the ulcer in accordance with the method of claim 1.

19. A method of decreasing the likelihood of sepsis resulting from an infected diabetic foot ulcer in a patient comprising treating the ulcer in accordance with the method of claim 1.

20. A method of treating an infected diabetic foot ulcer in a patient:
   (1) washing or irrigating the ulcer with an oxidative reductive potential (ORP) water solution;
   (2) soaking the ulcer in the ORP water solution;
   (3) dressing the ulcer with a wound dressing saturated with the ORP water solution, and,
   (4) optionally repeating steps (1)-(3),
   wherein the solution has a pH of about 6.4 to about 7.8 and is stable for at least two months, wherein the ORP water solution comprises anode water and cathode water, wherein the ORP water solution comprises free chlorine species at a level of from about 30 ppm to about 100 ppm, and wherein the free chlorine species comprises at least one of: hypochlorous acid present in an amount of from about 15 ppm to about 35 ppm and sodium hypochlorite present in an amount from about 25 ppm to about 50 ppm.

21. A method of treating an infected diabetic foot ulcer in a patient:
   (1) debriding the ulcer;
   (2) washing or irrigating the ulcer with an oxidative reductive potential (ORP) water solution;
   (3) soaking the ulcer in the solution for at least two minutes;
   (4) drying the ulcer for at least two minutes;
   (5) dressing the ulcer with a wound dressing saturated with the solution; and
   (6) optionally repeating steps (1)-(5),
   wherein the ulcer is an infected Grade 2 or Grade 3 foot ulcer, said ulcer having a surface area of at least 2.0 cm$^2$, wherein the solution has a pH of about 6.4 to about 7.8 and is stable for at least two months, wherein the ORP water solution comprises anode water and cathode water, wherein the ORP water solution comprises free chlorine species at a level of from about 30 ppm to about 100 ppm, and wherein the free chlorine species comprises at least one of: hypochlorous acid present in an amount of from about 15 ppm to about 35 ppm and sodium hypochlorite present in an amount from about 25 ppm to about 50 ppm.

22. The method of claim 21, further comprising repeating steps (1)-(5) at least one time.

23. The method of claim 21, further comprising repeating steps (1)-(5) until the ulcer is substantially healed.

* * * * *